(12) United States Patent
Nishimura et al.

(10) Patent No.: US 9,115,367 B2
(45) Date of Patent: Aug. 25, 2015

(54) STOMATA-INCREASING AGENT, POLYPEPTIDE, METHOD FOR INCREASING NUMBER AND/OR DENSITY OF STOMATA IN PLANT, AND METHOD FOR INCREASING YIELD OF PLANT

(75) Inventors: Ikuko Nishimura, Kyoto (JP); Shigeo Sugano, Kyoto (JP); Tomoo Shimada, Kyoto (JP)

(73) Assignee: KYOTO UNIVERSITY, Kyoto-shi (JP)

( * ) Notice: Subject to any disclaimer, the term of this patent is extended or adjusted under 35 U.S.C. 154(b) by 577 days.

(21) Appl. No.: 13/514,215

(22) PCT Filed: Dec. 7, 2010

(86) PCT No.: PCT/JP2010/071934
§ 371 (c)(1),
(2), (4) Date: Aug. 29, 2012

(87) PCT Pub. No.: WO2011/071050
PCT Pub. Date: Jun. 16, 2011

(65) Prior Publication Data
US 2013/0007920 A1 Jan. 3, 2013

(30) Foreign Application Priority Data
Dec. 7, 2009 (JP) ................................ 2009-278065

(51) Int. Cl.
*C12N 15/82* (2006.01)
*C07K 14/415* (2006.01)
*A01G 7/00* (2006.01)

(52) U.S. Cl.
CPC ............. *C12N 15/8261* (2013.01); *A01G 7/00* (2013.01); *C07K 14/415* (2013.01)

(58) Field of Classification Search
None
See application file for complete search history.

(56) References Cited

FOREIGN PATENT DOCUMENTS

| JP | 2002 512035 | 4/2002 |
|---|---|---|
| JP | 2002 527070 | 8/2002 |
| WO | WO 99/54471 A1 | 10/1999 |

OTHER PUBLICATIONS

Hunt et al. 2010. New Phytologist 186 pp. 609-614.*
Hara et al. Plant Cell Physiol. 50(6): 1019-1031 (2009).*
Guo et al (2004, Proc. Natl. Acad. Sci. USA 101: 9205-9210).*
Sugano, S., et al., "Kiko Bunka o Sokushin suru Shinki no Bunpitsusei Peptide," Proceedings of the 50th Annual Meeting of the Japanese Society of Plant Physiologists, p. 202, 3aB02 (361), (Mar. 16, 2009).
Sugano, S.S., et al., "Stomagen positively regulates stomatal density in *Arabidopsis*," Nature, vol. 463, No. 7278, pp. 241-244, (Jan. 14, 2010).
Shimada, T., et al., "Shinki Paptide Hormone 'Stomagen' wa Kiko Mitsudo o Seigyo suru," Cell Technology, vol. 29, No. 5, pp. 478-479, (Apr. 22, 2010).
Kondo, T., et al., "Stomatal Density is Controlled by a Mesophyll-Derived Signaling Molecule," Plant Cell Physiology, vol. 51, No. 1, pp. 1-8, (Jan. 2010).
International Search Report Issued Jan. 11, 2011 in PCT/JP10/71934 Filed Dec. 7, 2010.
Jeanette A. Nadeau, et al., "Control of Stomatal Distribution on the *Arabidopsis* Leaf Surface", Science, vol. 296, May 31, 2002, pp. 1697-1700.
Elena D. Shpak, et al., "Stomatal Patterning and Differentiation by Synergistic Interactions of Receptor Kinases", Science, vol. 309, Jul. 8, 2005, pp. 290-293 (with Supporting Online Material).
Kenta Hara, et al., "The secretory peptide gene *EPF1* enforces the stomatal one-cell-spacing rule", Genes & Development, vol. 21, 2007, pp. 1720-1725.
Lee Hunt, et al., "The Signaling Peptide EPF2 Controls Asymmetric Cell Divisions during Stomatal Development", Current Biology, vol. 19, No. 10, May 26, 2009, pp. 864-869.
Kenta Hara, et al., "Epidermal Cell Density is Autoregulated via a Secretory Peptide, Epidermal Patterning Factor 2 in *Arabidopsis* Leaves", Plant Cell Physiol., vol. 50, No. 6, 2009, pp. 1019-1031.
Dieter Berger, et al., "A subtilisin-like serine protease involved in the regulation of stomatal density and distribution in *Arabidopsis thaliana*", Genes & Development, vol. 14, 2000, pp. 1119-1131.
Extended European Search Report issued Mar. 28, 2013, in European Patent Application No. 10835970.4.
Database Uniprot [Online], "Subname: Full=Predicted protein;", Database Accession No. B9GQQ4, XP-002694061, Mar. 24, 2009, 2 pages.
Database Uniprot [Online], "RecName: Full=Epidermal Patterning Factor-like protein 9; Short=EPF-like protein 9; Flags: Precursor;", Database Accession No. Q9SV72, XP-002694062, May 1, 2000, 3 pages.

* cited by examiner

*Primary Examiner* — Anne Kubelik
*Assistant Examiner* — Charles Logsdon
(74) *Attorney, Agent, or Firm* — Oblon, McClelland, Maier & Neustadt, L.L.P.

(57) ABSTRACT

A stomata-increasing agent containing a compound capable of increasing the number and/or density of stomata in a plant, a polypeptide containing the amino acid sequence shown in SEQ ID NO: 6 or a variant thereof, a method for increasing the number and/or density of stomata in a plant and a method for increasing the yield of a plant are provided.

12 Claims, 42 Drawing Sheets

FIG. 6
(a) 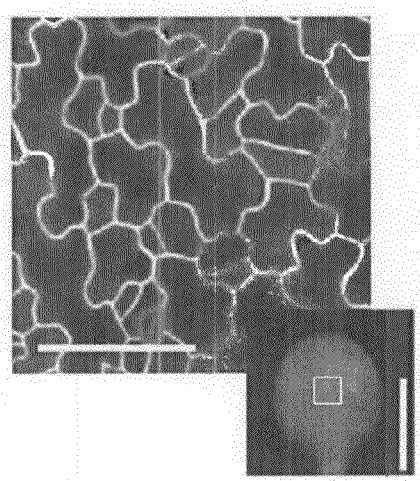
(b) 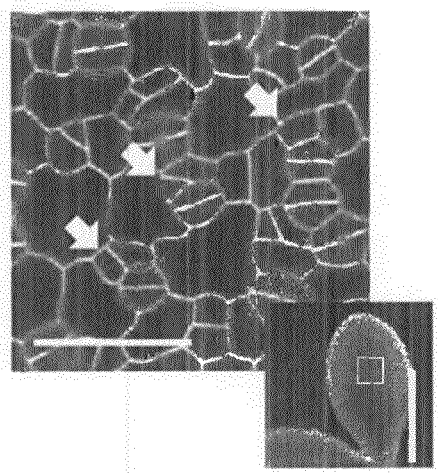

FIG. 7
(a)
(b)
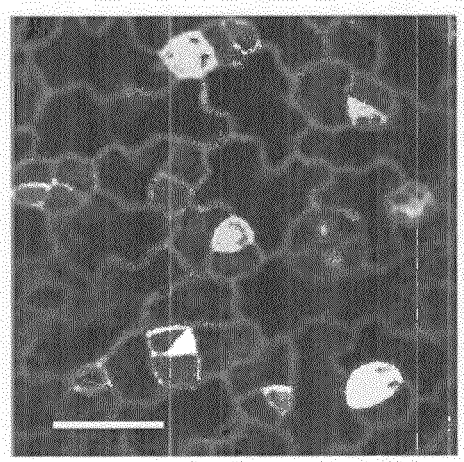
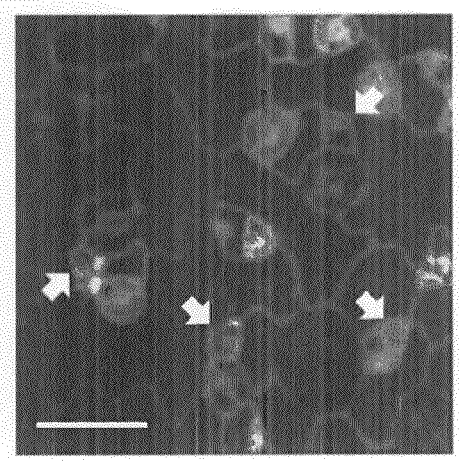

FIG. 9
(a)
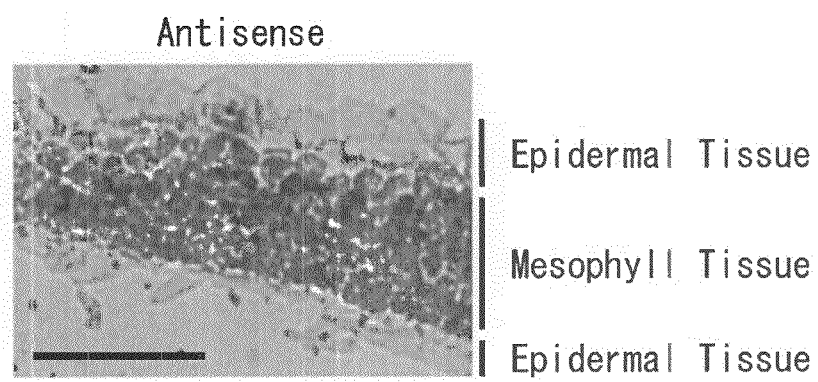
(b)
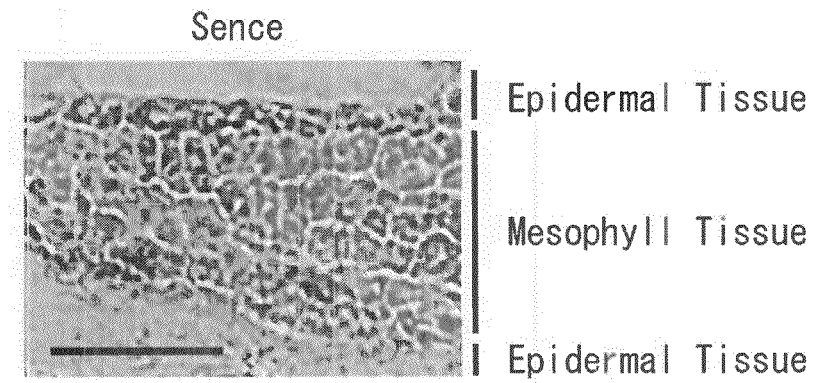

*FIG. 16*
(A)
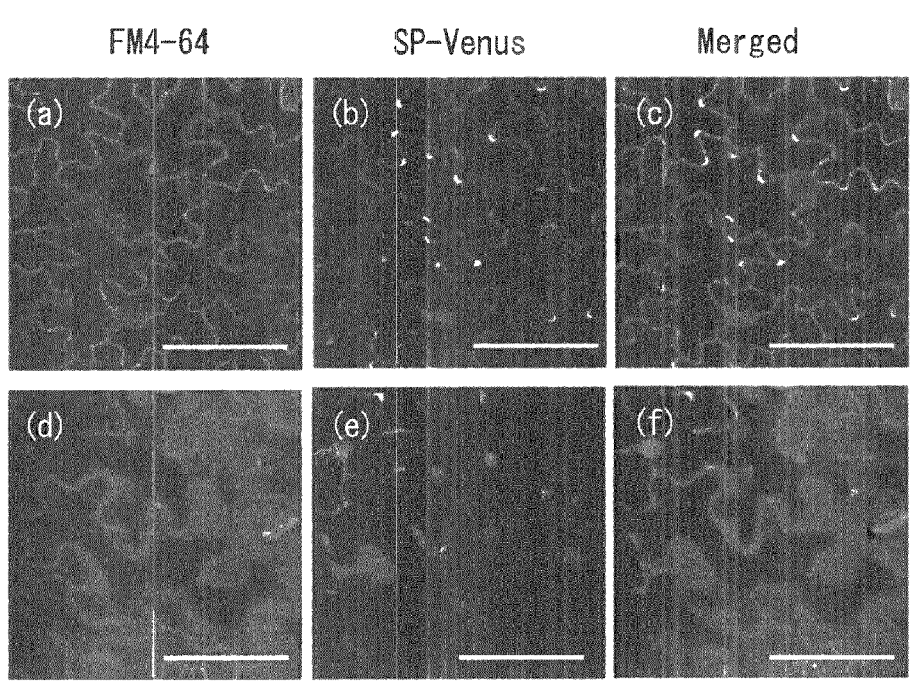
(B)
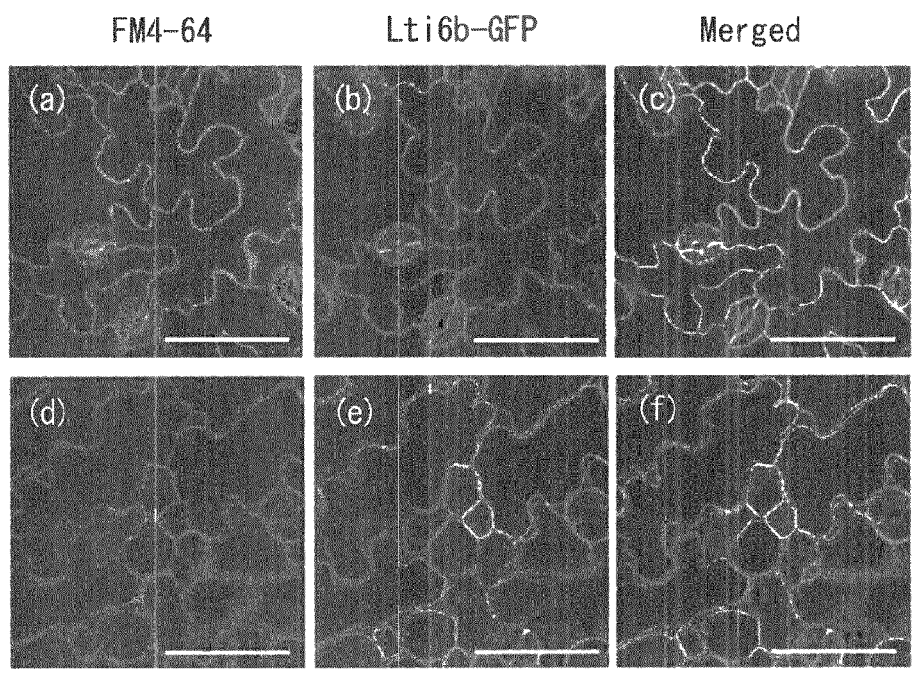

FIG. 19
(a)
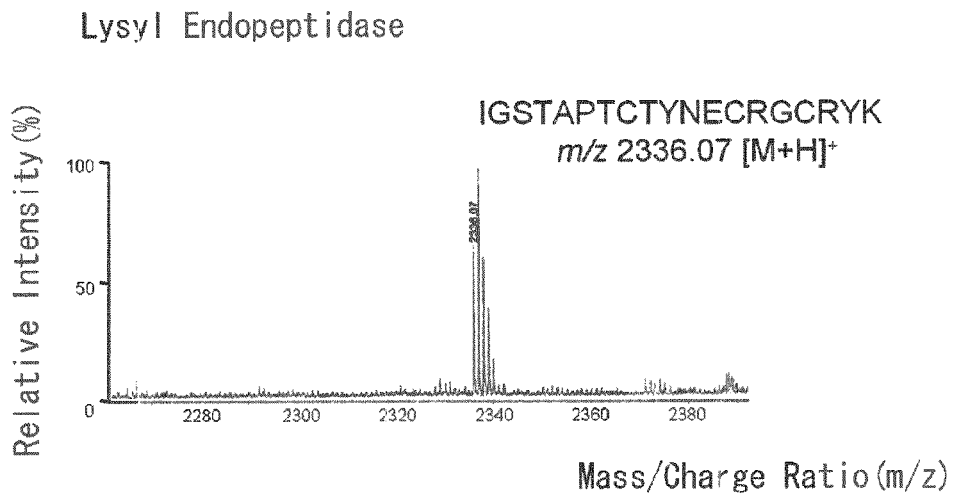
(b)
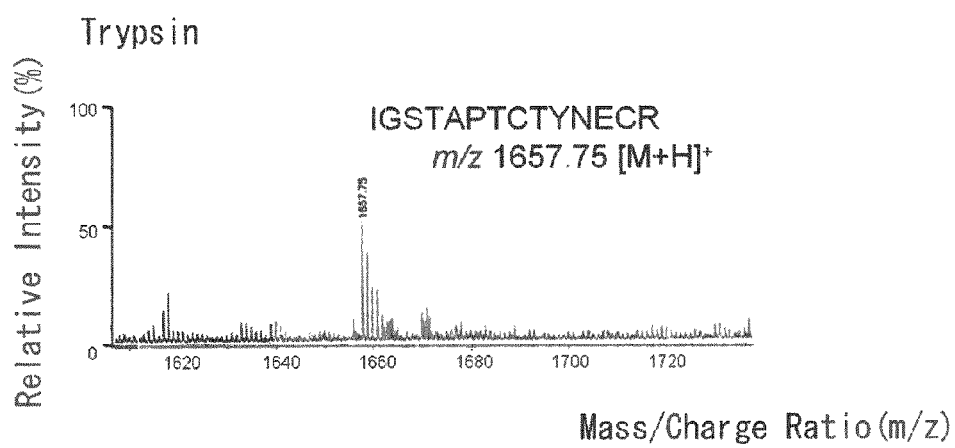

FIG. 20

| | | |
|---|---|---|
| Arabidopsis thaliana | ----------MKHEMMNIKPRCITIFFLLFALLLGNYVVQASRPRSI-----ENTVSLLP | 45 |
| Oryza sativa | MANACPTSTTSSLPLFLFCFLLFSHARCNQGHHGSISGTDYGEQYPHQTLPEEHIHLQE | 60 |
| Vitis vinifera | ----------MLISKQPNL-FLVLLFTLLFAAYFTQGSKSQVVPPYHQREIVHLQS | 45 |
| Populus trichocarpa | ----------MANTRLCY-LLSLLFTLLAAFVIQGSRNQELLPYHQSISTPSQE | 44 |
| Selaginella moellendorffii | | 0 |
| | | |
| Arabidopsis thaliana | QVHLL-----NSRHHIGSTABTCTYNECRGCRYRCRAEQVFTENDPINSAYHYRCW | 99 |
| Oryza sativa | NIKVLNKERLPKYARMLIGSTAPITYNECRGCRFKCTEQVPVDANDPMNSAYHYKCV | 120 |
| Vitis vinifera | SGEQW--MNRNSRELMIGSTRPTCTYNECRGCKYKCRAEQVPVENDPINSAYHYRCV | 101 |
| Populus trichocarpa | DSQALGGNEEQMSSKLMIGSTAPTCTYDECRGCKYKCRAEQVPVENDPIHSAYHYKCI | 104 |
| Selaginella moellendorffii | ----MINEWQYPSDFRAMVESTAPSCTYMECRDCKTERAEQVFLNSRNEKESAIRLW | 56 |
| | | |
| Arabidopsis thaliana | CHR-- | 102 (SEQ ID NO:1) |
| Oryza sativa | CHT-- | 123 (SEQ ID NO:2) |
| Vitis vinifera | CHR-- | 104 (SEQ ID NO:3) |
| Populus trichocarpa | HR--- | 107 (SEQ ID NO:4) |
| Selaginella moellendorffii | CRKRH | 61 (SEQ ID NO:5) |

FIG. 29
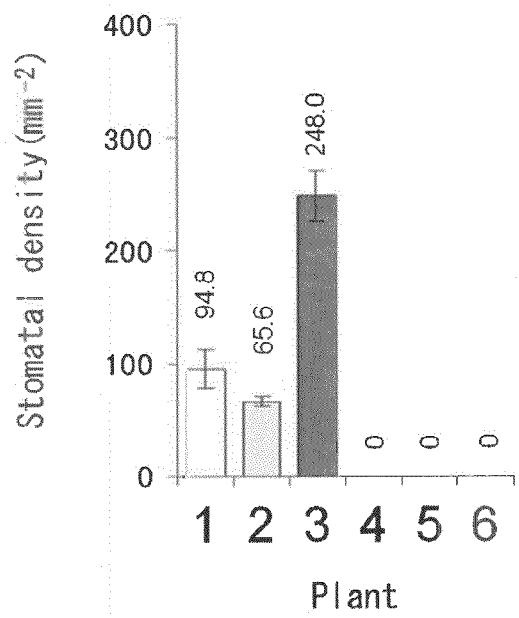
(a) Stem
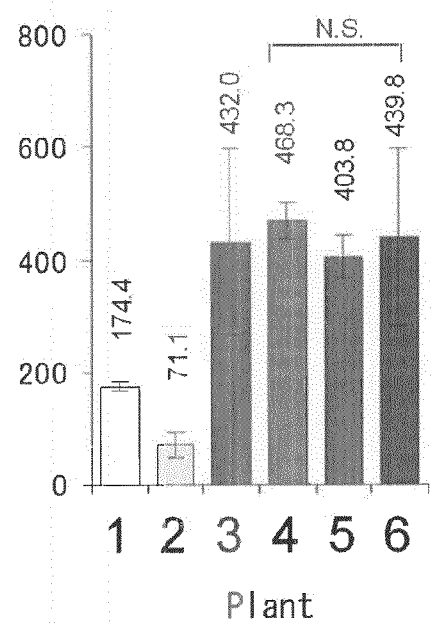
(b) Leaf

FIG. 30
(A)
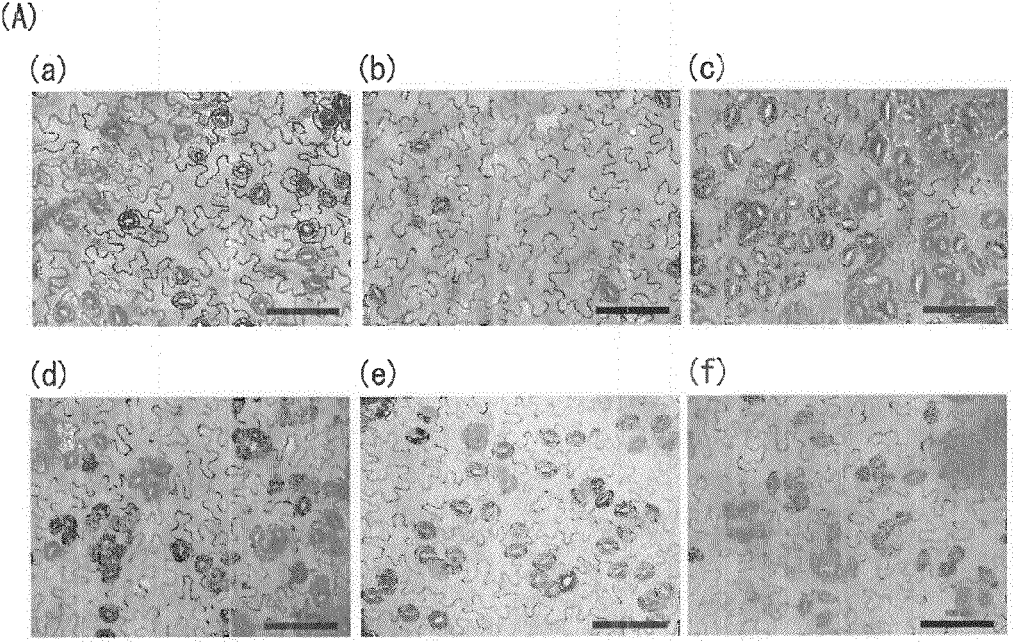
(B)
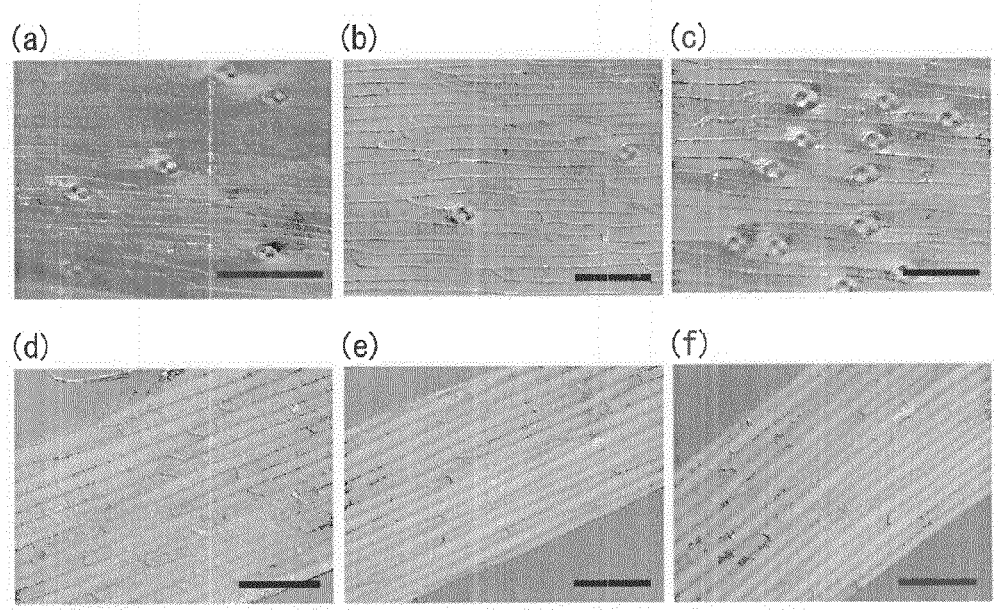

FIG. 39
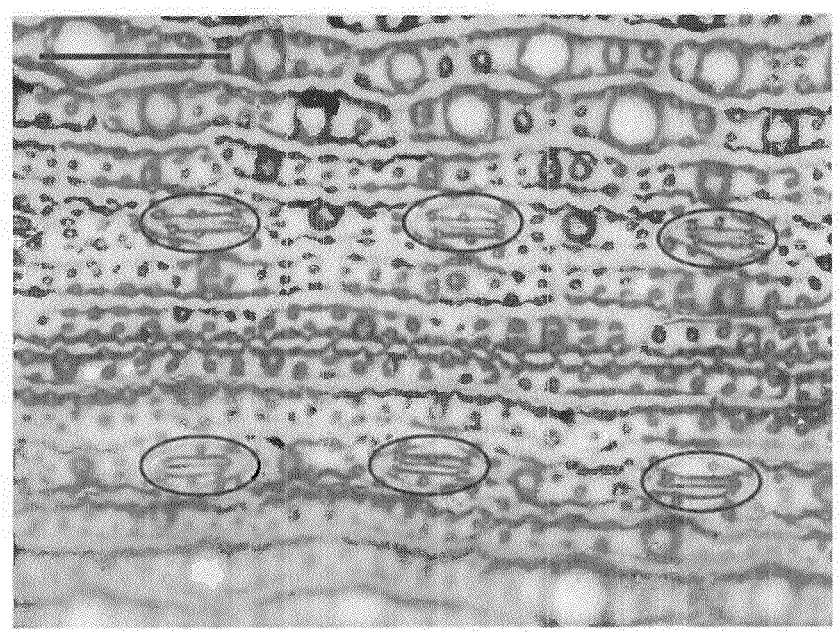
(b)
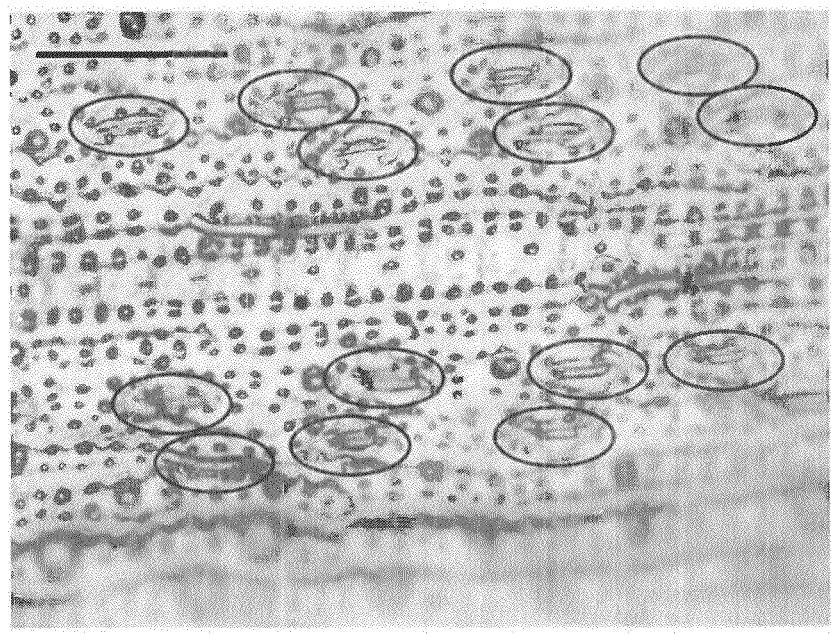
(a)

FIG. 41
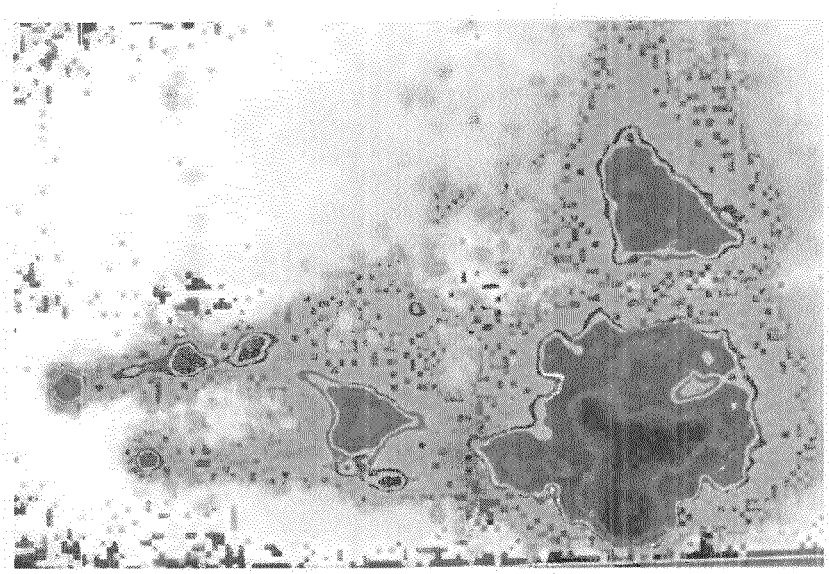
(a)
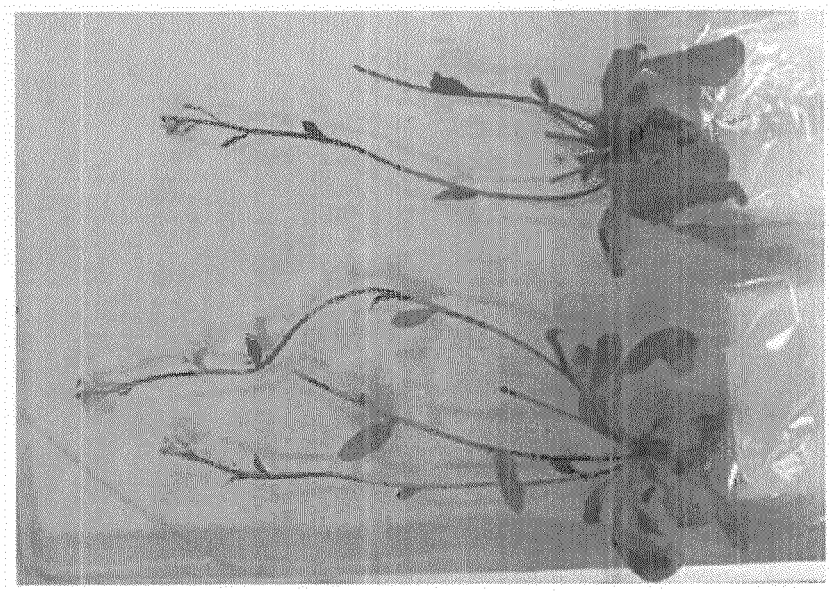
(b)

STOMATA-INCREASING AGENT, POLYPEPTIDE, METHOD FOR INCREASING NUMBER AND/OR DENSITY OF STOMATA IN PLANT, AND METHOD FOR INCREASING YIELD OF PLANT

This application is a National Stage of PCT/JP10/071934 filed Dec. 7, 2010 and claims the benefit of JP 2009-278065 filed Dec. 7, 2009.

TECHNICAL FIELD

The present invention relates to a stomata-increasing agent, a polypeptide, a method for increasing the number and/or density of stomata in a plant and a method for increasing the yield of a plant. More specifically, the present invention relates to a stomata-increasing agent, a polypeptide, and a method for increasing the number and/or density of stomata in a plant, which are useful for an increase in the amount of carbon dioxide absorption by a plant, and a method for increasing the yield of a plant, which is useful for an increase in the production amount of a plant.

BACKGROUND ART

Stomatal development in leaves is negatively regulated by receptor-like proteins {TOO MANY MOUTHS; hereinafter, referred to as "TMM"} and ERECTA family receptor-like kinases (ER, ERL1 and ERL2) (for example, see Non Patent Literatures 1 and 2).

Two possible ligands which bind to these receptors, EPIDERMAL PATTERNING FACTOR (hereinafter, referred to as "EPF") 1 and EPF2, act as negative signaling factors at distinct steps during stomatal development (for example, see Non Patent Literatures 3 to 5). In addition, another negative regulator (STOMATAL DENSITY AND DISTRIBUTION 1; hereinafter, referred to as "SDD1"), which is a subtilisin-type proteinase, is reported to be dependent on TMM to function (for example, see Non Patent Literature 6).

CITATION LIST

Non Patent Literature

{Non Patent Literature 1} Nadeau, J. A. & Sack, F. D. Control of stomatal distribution on the *Arabidopsis* leaf surface. Science 296, 1697-1700 (2002)

{Non Patent Literature 2} Shpak, E. D., McAbee, J. M., Pillitteri, L. J. & Torii, K. U. Stomatal patterning and differentiation by synergistic interactions of receptor kinases. Science 309, 290-293 (2005)

{Non Patent Literature 3} Hara, K., Kajita, R., Torii, K. U., Bergmann, D. C. & Kakimoto, T. The secretory peptide gene EPF1 enforces the stomatal one-cell-spacing rules. Genes Dev. 21, 1720-1725 (2007)

{Non Patent Literature 4} Hunt, L. & Gray, J. E. The signaling peptide EPF2 controls asymmetric cell divisions during stomatal development. Curr. Biol. 19, 864-869 (2009)

{Non Patent Literature 5} Hara, K. et al. Epidermal cell density is autoregulated via a secretory peptide, EPIDERMAL PATTERNING FACTOR 2 in *Arabidopsis* leaves. Plant Cell Physiol. 50, 1019-1031 (2009)

{Non Patent Literature 6} Berger, D. & Altmann, T. Asubtilisin-like serine protease involved in the regulation of stomatal density and distribution in *Arabidopsis thaliana*. Genes Dev. 14, 1119-1131 (2000)

SUMMARY OF THE INVENTION

However, the present inventors have not found at present a literature specifically describing a signaling factor that can positively regulate stomatal development in a plant and increase the number and/or density of stomata in a plant.

The present invention has been made in view of the above prior art, and an object of the present invention is to provide a stomata-increasing agent, a polypeptide, and a method for increasing the number and/or density of stomata in a plant, which can increase the number and/or density of stomata in a plant. In addition, an object of the present invention is to provide a method for increasing the yield of a plant, which can easily increase the yield of a plant.

Specifically, the gist of the present invention is:

(1) a stomata-increasing agent comprising a compound capable of increasing the number and/or density of stomata in a plant, (2) the stomata-increasing agent according to the above item (1), wherein the compound is a polypeptide comprising an amino acid sequence selected from the group consisting of:

(I) the amino acid sequence shown in SEQ ID NO: 6, (II) an amino acid sequence having substitution, deletion, addition or insertion of one or several amino acid residues in SEQ ID NO: 6, wherein the amino acid sequence constitutes a polypeptide having at least a property of positively regulating stomatal development in a plant, (III) an amino acid sequence of which sequence identity is 64% or more, the sequence identity being obtained by aligning the amino acid sequence with the amino acid sequence shown in SEQ ID NO: 6 with the use of BLAST algorithm under conditions of Cost to open gap 11, Cost to extend gap 1, expect value 10 and wordsize 3 for calculation, wherein a polypeptide encoded thereby has at least a property of positively regulating stomatal development in a plant, and (IV) an amino acid sequence which is encoded by a nucleic acid capable of hybridizing to a complementary nucleic acid of a nucleic acid encoding the amino acid sequence shown in SEQ ID NO: 6 under stringent conditions, wherein a polypeptide encoded thereby has at least a property of positively regulating stomatal development in a plant, (3) a polypeptide comprising an amino acid sequence selected from the group consisting of:

(I) the amino acid sequence shown in SEQ ID NO: 6, (II) an amino acid sequence having substitution, deletion, addition or insertion of one or several amino acid residues in SEQ ID NO: 6, wherein the amino acid sequence constitutes a polypeptide having at least a property of positively regulating stomatal development in a plant, (III) an amino acid sequence of which sequence identity is 64% or more, the sequence identity being obtained by aligning the amino acid sequence with the amino acid sequence shown in SEQ ID NO: 6 with the use of BLAST algorithm under conditions of Cost to open gap 11, Cost to extend gap 1, expect value 10 and wordsize 3 for calculation, wherein a polypeptide encoded thereby has at least a property of positively regulating stomatal development in a plant, and (IV) an amino acid sequence which is encoded by a nucleic acid capable of hybridizing to a complementary nucleic acid of a nucleic acid encoding the amino acid sequence shown in SEQ ID NO: 6 under stringent conditions, wherein a polypeptide encoded thereby has at least a property of positively regulating stomatal development in a plant, (4) a method for increasing the number and/or density of stomata in a plant characterized in that the method comprises contacting the stomata-increasing agent of the above item (1) to a plant or overexpressing the polypeptide of the above item (3) in a plant, (5) the method for increasing the number and/or density of stomata in a plant according to the above item (4), wherein the plant is a vascular plant, (6) a plant which is obtained by the method for increasing the number and/or density of stomata in a plant of the above item (4) or (5), and (7) a method for increasing the yield of a plant, characterized in that the method comprises contacting the stomata-increasing agent of the above item (1) to a plant or overexpressing the polypeptide of the above item (3) in a plant.

The stomata-increasing agent, the polypeptide and the method for increasing the number and/or density of stomata in a plant of the present invention exhibit an excellent effect that the number and/or density of stomata in a plant can be increased. Therefore, according to the present invention, since an increase in the amount of carbon dioxide absorption by a plant can be achieved, the present invention is useful for reduction in the amount of carbon dioxide in the atmosphere. In addition, according to the present invention, since the amount of carbon fixation in a plant can be increased by the increase in the amount of carbon dioxide absorption, an increase in the yield of a plant or the like can be achieved. Furthermore, the method for increasing the yield of a plant of the present invention exhibits an excellent effect that the yield of a plant can be easily increased.

BRIEF DESCRIPTION OF DRAWINGS

FIG. 6 (a) is a photograph substituted for drawing of a confocal microscopic image showing the result of observing the abaxial epidermis of a cotyledon in a wild-type strain in Test Example 1, and (b) is a photograph substituted for drawing of a confocal microscopic image showing the result of observing the abaxial epidermis of a cotyledon in a stomagen-overexpressing line 10 in Test Example 1.

FIG. 7 (a) is a photograph substituted for drawing of a confocal microscopic image showing the result of observing the epidermis of the first leaf in a wild-type strain in Test Example 1, and (b) is a photograph substituted for drawing of a confocal microscopic image showing the result of observing the epidermis of the first leaf in a stomagen-overexpressing pTMM::GFP line in Test Example 1.

FIG. 9 (a) is a photograph substituted for drawing of a microscopic image showing the result of performing in situ hybridization analysis of leaf primordia using antisense probes of a stomagen gene in Test Example 2, and (b) is a photograph substituted for drawing of a microscopic image showing the result of performing in situ hybridization analysis using sense probes of a stomagen gene in leaf primordia in Test Example 2.

FIG. 16 (A) shows photographs substituted for drawings of confocal microscopic images showing the result of observing abaxial epidermis of cotyledons at 3 days after germination of a SP-Venus-expressing line stained with FM4-64 in Test Example 8, and (B) is a photograph substituted for drawing of confocal microscopic image showing the result of observing abaxial epidermis of cotyledons at 3 days after germination of an Lti6b-GFP line stained with FM4-64 in Test Example 8.

FIG. 18 includes sequences IGSTAPTXTY (SEQ ID NO: 42) and VKFNFXSFXG (SEQ ID NO: 43).

FIG. 19 (a) is a graph showing the result of analyzing the N-terminal amino acid sequence of stomagen-Venus by mass spectrometry using lysyl endopeptidase in Example 2, and (b) is a graph showing the result of analyzing the N-terminal amino acid sequence of stomagen-Venus by mass spectrometry using trypsin in Example 2. FIG. 19 includes sequences IGSTAPTCTYNECRGCRYK (residues 58-76 of SEQ ID NO: 1) and IGSTAPTCTYNECR (residues 58-71 of SEQ ID NO: 1.

FIG. 20 is a drawing showing the result of multiple alignment of orthologs in each of *Oryza sativa* (Os01g0914400), *Vitis vinifera* (AM444732), *Populus trichocarpa* (Pt02g2557), and *Selaginella moellendorffii* (Sm084711) of stomagen conducted by Clustal W in Example 2.

FIG. 24 includes the sequence RRRHMIGSTAPTCTYNECR (residues 53-71 of SEQ ID NO: 1).

FIG. 29 (a) is a graph showing the result of examining the relationship between the types of plants and stomatal density in a stem in Test Example 10, and (b) is a graph showing the result of examining the relationship between the types of plants and stomatal density in a leaf in Test Example 10.

FIG. 30 (A) shows photographs substituted for drawings of differential interference images showing the result of observing abaxial epidermis of first leaves of each of a wild-type strain, a stomagen-silenced line, a stomagen-overexpressing line, a tmm mutant, a stomagen-silenced tmm mutant and a stomagen-overexpressing tmm mutant in Test Example 10, and (B) shows photographs substituted for drawings of differential interference images showing the result of observing stems of each of a wild-type strain, a stomagen-silenced line, a stomagen-overexpressing line, a tmm mutant, a stomagen-silenced tmm mutant and a stomagen-overexpressing tmm mutant in Test Example 10.

FIG. 39 (a) is a photograph substituted for drawing of a differential interference image of abaxial epidermis of a second leaf of a rice to which synthesized stomagen was administered in Test Example 14, and (b) is a photograph substituted for drawing of a differential interference image of abaxial epidermis of a second leaf of rice to which synthesized stomagen was not administered in Test Example 14.

FIG. 41 shows photographs substituted for drawings of the result of determining $^{11}CO_2$ taken in a wild-type strain or a stomagen-silenced line in Test Example 15.

DESCRIPTION OF EMBODIMENTS

Figure 1:
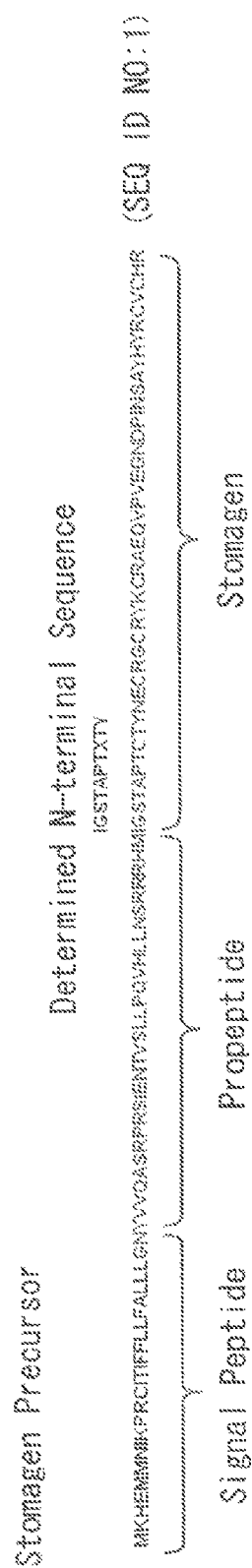
FIG. 1 is a drawing showing structures of the polypeptide (stomagen) of the present invention and a precursor thereof (stomagen precursor).

1. Stomata-Increasing Agent of Present Invention and Polypeptide of Present Invention The stomata-increasing agent of the present invention is characterized by containing a compound capable of increasing the number and/or density of stomata in a plant. According to the stomata-increasing agent, since undifferentiated epidermal cells can be differentiated to guard cells which constitute a stoma, the number and/or density of stomata in a plant can be increased. Here, the phrase "increase in the number of stomata in a plant" refers to that the number of stomata is larger than at least the number in a wild-type plant, and the phrase "increase in the density of stomata in a plant" refers to that the density of stomata is higher than the density in a wild-type plant. The number and density of stomata can be determined, for example, by observation with a microscope and the like.

The present inventors have found that the stomata in a plant are increased by overexpressing a polypeptide comprising the amino acid sequence shown in SEQ ID NO: 6 or administrating the polypeptide to the plant, whereby the polypeptide acts as a positive intercellular signaling factor in stomatal development in epidermal cells in a plant. In addition, the present inventors have found that a precursor of the polypeptide is expressed more in internal mesophyll cells than in epidermal cells where stomata develop, and a signal peptide sequence and a propeptide sequence are cleaved and bind to a receptor TMM on undifferential epidermal cells competitively with a negative regulator EPF2, whereby the undifferential epidermal cells can be differentiated to guard cells, to form a stoma. The present invention is based on these findings.

The compound includes, for example, a polypeptide comprising an amino acid sequence selected from the group consisting of:

(I) the amino acid sequence shown in SEQ ID NO: 6,
(II) an amino acid sequence having substitution, deletion, addition or insertion of one or several amino acid residues in SEQ ID NO: 6, wherein the amino acid sequence constitutes a polypeptide having at least a property of positively regulating stomatal development in a plant,
(III) an amino acid sequence of which sequence identity is 64% or more, the sequence identity being calculated by aligning the amino acid sequence with the amino acid sequence shown in SEQ ID NO: 6 and conducting BLAST algorithm under conditions of Cost to open gap 11, Cost to extend gap 1, expect value 10 and wordsize 3, wherein a polypeptide encoded thereby has at least a property of positively regulating stomatal development in a plant, and
(IV) an amino acid sequence which is encoded by a nucleic acid capable of hybridizing to a complementary nucleic acid of a nucleic acid encoding the amino acid sequence shown in SEQ ID NO: 6 under stringent conditions, wherein a polypeptide encoded thereby has at least a property of positively regulating stomatal development in a plant;

a pseudo-compound based on the polypeptides; a substance positively regulating a promoter corresponding to a nucleic acid encoding the polypeptides; a substance contributing to stabilization of stomagen (for example, an inhibitor on a protease which cleavages stomagen, and the like) and the like.

Whether the compound has the property of positively regulating stomatal development in a plant can be evaluated by, for example, contacting a compound to be subjected with a young plant, growing the plant for several days, determining the density and number of stomata in the obtained plant (also referred to as a "treated plant"), and comparing the density and number of stomata in the treated plant with the density and number of stomata in a plant not contacted with the compound. In this time, when the density and number of stomata in the treated plant is larger than the density and number of stomata in a plant not contacted with the compound, the compound to be subjected can be evaluated to have the property of positively regulating stomatal development in a plant.

Incidentally, stomatal development in a plant can be positively regulated by overexpressing the polypeptide in a plant. Therefore, the present invention also encompasses the polypeptide.

Since the polypeptide has the amino acid sequence, the polypeptide can act on a receptor TMM on undifferentiated epidermal cells and promotes differentiation from the undifferentiated epidermal cells into guard cells which constitute a stoma in a plant, thereby increasing the density of stomata in the plant.

The present invention also encompasses a variant of a polypeptide comprising the amino acid sequence shown in SEQ ID NO: 6 of the above (I), as long as the variant shows the property of positively regulating stomatal development in a plant. The variant herein refers to a polypeptide comprising any of the amino acid sequences of the above (II) to (IV).

In the amino acid sequence of the above (II), "substitution, deletion, addition or insertion of one or several amino acid residues" exist in at least one of the inside, C-terminus and N-terminus of the amino acid sequence shown in SEQ ID NO: 6. Here, "one or several" refers to the number in the range that a polypeptide showing the property of positively regulating stomatal development in a plant is constituted, and refers to 1 to 30, preferably 1 to 20, further preferably 1 to 10, and more preferably 1 to 3.

Incidentally, the substitution is preferably a conservative substitution, from the viewpoint of sufficiently ensuring the property of positively regulating stomatal development in a plant. The conservative substitution includes, for example, a substitution of a specific amino acid residue with an amino acid residue exhibiting similar functions therewith, the functions including, for example, hydrophobicity, charge, pK, conformational characteristics and the like (hereinafter also referred to as a similar amino acid residue). More specifically, the conservative substitution includes, for example, a substitution between a glycine residue and an alanine residue, a substitution between a valine residue, an isoleucine residue and a leucine residue, a substitution between an aspartic acid residue, a glutamic acid residue, an asparagine residue and a glutamine residue, a substitution between a serine residue and a threonine residue, a substitution between a lysine residue and an arginine residue, a substitution between a phenylalanine residue and a tyrosine residue, and the like.

In the amino acid sequence of the above (III), the sequence identity is 64% or more, preferably 80% or more, further preferably 95% or more, and particularly preferably 100%, as the value aligned and calculated with BLAST algorithm under the conditions of Cost to open gap 11, Cost to extend gap 1, expect value 10, and wordsize 3, from the viewpoint of sufficiently ensuring the property of positively regulating stomatal development in a plant.

In the above (IV), the "stringent conditions" include, for example, conditions for incubating the complementary nucleic acid and a nucleic acid to be hybridized corresponding to the complementary nucleic acid for 10 hours in a hybridization solution {composition: 6×SSC (composition: 0.9 M sodium chloride, 0.09M sodium citrate, adjusted to pH 7.0), 0.5% by mass sodium dodecyl sulfate, 5× Denhardt's solution, 100 μg/ml denatured salmon sperm DNA, and 50% by volume formamide} at a temperature of room temperature, 42° C. or more as more stringent conditions, or 60° C. or more as further stringent conditions, followed by, for example, washing under the condition of an ionic strength of 2×SSC and 0.1×SSC as more stringent conditions at a temperature of room temperature, 42° C. or more as more stringent conditions, or 60° C. or more as further stringent conditions. In addition, the "complementary nucleic acid" refers to a nucleic acid completely complementary to a nucleic acid encoding the amino acid sequence shown in SEQ ID NO: 6.

In the present invention, the polypeptide can be a polypeptide comprising a part of the amino acid sequences of the above (I) to (IV), as long as the polypeptide shows the property of positively regulating stomatal development in a plant.

The polypeptide can be produced, for example, by a chemical synthesis method such as a solid-phase peptide synthesis method or a biological method using a cell or a bacterium, the cell or bacterium harboring a nucleic acid encoding the polypeptide. Among them, the biological method is preferable, from the viewpoint of being capable of producing the polypeptide in large amounts at low cost.

The cell used in the biological method includes, for example, a recombinant cell obtained by introducing a nucleic acid encoding the polypeptide of the present invention into a suitable host cell such as a plant cell (for example, a tobacco-cultured cell including BY-2 cell and the like), a yeast cell, *E. coli* and an insect cell in an expressible manner. In the biological method, the polypeptide of the present invention can be produced by culturing the cell in a suitable medium.

The nucleic acid encoding the polypeptide includes, for example, a nucleic acid encoding the amino acid sequence shown in SEQ ID NO: 6, a mutant nucleic acid thereof and the like. The mutant nucleic acid includes a nucleic acid encoding the amino acid sequence of any of the above items (II) to (IV), and the like. In addition, the mutant nucleic acid can be a nucleic acid hybridizing to a nucleic acid comprising a nucleotide sequence completely complementary to a nucleotide sequence corresponding to the amino acid sequence shown in SEQ ID NO: 6 under the stringent conditions, as long as the polypeptide encoded thereby shows the property of positively regulating stomatal development in a plant. The nucleic acid can be introduced into the host cell by an electroporation method, a lipofection method, a transfection method, a particle gun method, or the like.

The pseudo-compound based on a polypeptide includes, for example, a pseudo-compound based on the polypeptide, wherein the compound acts on a receptor TMM on undifferentiated epidermal cells to increase the number and/or density of stomata in a plant. Herein, the concept of "pseudo-compound based on the polypeptide" encompasses, for example, a peptide compound or a nonpeptide compound designed based on the conformation of a part contributing to bioactivity in the polypeptide, a peptide comprising a part of the polypeptide and the like.

In addition, the concept of "a substance for positively regulating a promoter corresponding to a nucleic acid encoding the polypeptide" encompasses a substance for increasing the activity of the promoter.

The stomata-increasing agent of the present invention can be an agent consisting of the compound or an agent comprising the compound and a suitable auxiliary agent.

When the stomata-increasing agent of the present invention comprises the compound and the suitable auxiliary agent, the content of the compound in the stomata-increasing agent can be appropriately controlled depending on a plant to be applied and the use of the stomata-increasing agent.

The auxiliary agent includes, for example, a buffer suitable for stably maintaining the properties and conformation of the compound and/or maintaining a plant, an absorption promoter which facilitates the uptake of the compound into a subject plant of the stomata-increasing agent, a medium for growing a plant and the like.

When the stomata-increasing agent is provided to a plant by diffusion, spraying or the like, the pH of the buffer may be in a range that is suitable for stably maintaining the properties and conformation of the compound. The pH of the buffer is, for example, preferably a pH of 5.5 to 8.5, further preferably a pH of 6 to 8, and more preferably a pH around 7.5. In addition, when the stomata-increasing agent is provided by immersing a young plant in the stomata-increasing agent, the pH of the buffer is, for example, a pH of 5 to 7, and more preferably a pH around 5.7.

The absorption promoter includes, for example, a solvent having the viscosity that can extend the time to contact of a leaf with the compound by attaching the compound to the leaf (for example, an aqueous solution of a polysaccharide and the like), a solvent promoting penetration of the compound into the inside of the leaf and the like.

The medium can be a medium suitable for growth of a plant.

2. Method for Increasing Number and/or Density of Stomata in Plant

The method for increasing the number and/or density of stomata in a plant of the present invention is characterized by contacting the above-described stomata-increasing agent with a plant, or overexpressing the above-described polypeptide in a plant.

In one aspect, the method for increasing the number and/or density of stomata in a plant of the present invention is a method characterized by contacting the above-described stomata-increasing agent with a plant (hereinafter, referred to as "Method 1"). In Method 1, since the stomata-increasing agent is used, undifferentiated epidermal cells can be differentiated into guard cells which constitute a stoma, thereby increasing the number and/or density of stomata in a plant.

In Method 1, the contact of a plant with the stomata-increasing agent is performed by immersion of a plant in a solution containing the stomata-increasing agent (for example, a stomata-developing agent containing at least the stomata-increasing agent, a medium as an auxiliary agent and the like) or operations such as direct application, diffusion and spraying of the stomata-increasing agent to a leaf, a stem, a calyx, an anther, and the like of a plant. In Method 1, the contact of a plant with the stomata-increasing agent can be performed by easy operations as described above.

The amount of the stomata-increasing agent contacted to a plant can be appropriately controlled depending on the amount of stomata to be developed in a plant. In addition, the contact time of a plant with the stomata-increasing agent can be appropriately controlled depending on the types of the plants, and the like.

The plant to which Method 1 is applied can be a plant having stomata and having a receptor to which the compound contained in the stomata-increasing agent binds. The plant is preferably a vascular plant, since the effect of developing stomata is large. The vascular plant is not particularly limited, and includes, for example, Fabaceae plant represented by soybean and the like, Gramineae plant represented by rice and the like, Brasscaceae plant represented by *Arabidopsis thaliana* and the like, Salicaceae plant represented by black cottonwood and the like, and Selaginellaceae plant represented by *Selaginella moellendorffii* and the like. In addition, the plant preferably has young leaves and young leaf buds, since the effect of developing stomata is large. Particularly, when the plant is immersed in a solution containing the stomata-increasing agent (for example, a stomata-developing agent containing at least the stomata-increasing agent and a medium as an auxiliary agent), a young plant (for example, a plant at 2 to 16 days of age) is preferable, since the effect of developing stomata is large.

Furthermore, in another aspect, the method for increasing the number and/or density of stomata in a plant of the present invention is, a method characterized by overexpressing the above-described polypeptide in a plant (hereinafter, referred to as "Method 2"). In Method 2, since the polypeptide is overexpressed, undifferentiated epidermal cells can be differentiated into guard cells that constitute a stoma, to increase the number and/or density of stomata in a plant.

The method for overexpressing the above-described polypeptide (polypeptide overexpression method) in a plant includes, for example, a method of introducing a nucleic acid encoding the polypeptide of the present invention into protoplast, callus or leaf disc of a plant to which Method 2 is applied by an electroporation method, a particle gun method, a transfection method, or the like, to redifferentiate the plant into a leaf, a root or the like and regenerate a plant. Redifferentiation into a leaf can be performed, for example, in the case of protoplast, by culturing the protoplast in a solid nutrient medium, to synthesize a cell wall, subsequently culturing in a liquid medium while vigorously stirring to give callus, and culturing the obtained callus in the presence of auxin and cytokinin. In addition, redifferentiation from callus into leaf can be performed, for example, by culturing the callus in the presence of auxin at low concentration and cytokinin at high concentration. Redifferentiation from leaf disc into a leaf can be performed, for example, by culturing the leaf disc in the presence of auxin at low concentration and cytokinin at high concentration. The medium used in the redifferentiation into the leaf can be appropriately selected depending on the types of the plants and the like. The medium includes, for example, a callus induction medium (MS medium containing 1 mg/L indoleacetic acid and 1 mg/L benzylaminopurine), a shoot induction medium (MS medium containing 0.1 mg/L indoleacetic acid and 1 mg/L benzylaminopurine) and the like. Incidentally, "overexpression" herein refers to production of the polypeptide of the present invention at a level at least higher than the expression level of the polypeptide in a wild-type plant.

The plant to which Method 2 is applied is the same as the plant to which Method 1 is applied.

As described above, according to the stomata-increasing agent, the polypeptide, and the method for increasing the number and/or density of stomata in a plant of the present invention, in a plant, for example, in the leaf, the stem, the calyx, the anther and the like of a plant, the number and/or density of stomata can be increased by positively regulating stomatal development and differentiating an undifferentiated epidermal cell to a guard cell. Therefore, since an increase in the amount of carbon dioxide absorption by a plant can be attempted according to the present invention, the present invention is useful for the reduction in the amount of carbon dioxide in the atmosphere. In addition, since the amount of carbon fixation in a plant can be increased by the increase in the amount of carbon dioxide absorption according to the present invention, an increase in the yield as a plant or the like can be attempted.

3. Plant Obtained by Method for Increasing Number and/or Density of Stomata in Plant In a plant obtained by the method for increasing the number and/or density of stomata in a plant as mentioned in the above, the number and/or density of stomata is large as compared to a wild-type plant. Therefore, according to the plant of the present invention, since the amount of carbon dioxide absorption is increased, the amount of carbon dioxide in the atmosphere can be reduced. In addition, according to the present invention, since the amount of carbon fixation is increased by the increase in the amount of carbon dioxide absorption in the plant of the present invention, an increase in the yield or the like can be attempted.

The plant is preferably a vascular plant, since large effect is exhibited by the increase in the number and/or density of stomata. The vascular plant is not particularly limited, and includes, for example, *Fabaceae* plant represented by soybean and the like, Gramineae plant represented by rice and the like, *Brasscaceae* plant represented by *Arabidopsis thaliana* and the like, Salicaceae plant represented by black cottonwood and the like, and *Selaginellaceae* plant represented by *Selaginella moellendorffii* and the like.

4. Method for Increasing Yield of Plant

The method for increasing the yield of a plant of the present invention is characterized by contacting the above-described stomata-increasing agent to a plant or overexpressing the above-described polypeptide in a plant.

In one aspect, the method for increasing the yield of a plant of the present invention is a method characterized by contacting the stomata-increasing agent to a plant (hereinafter, referred to as "Method 3"). In Method 3, since the stomata-increasing agent is used, the number and/or density of stomata in a plant can be increased, and the amount of carbon fixation in a plant can be increased to increase the yield of the plant, as compared to a wild-type plant (wild-type strain). In addition, in Method 3, the yield of the plant can be easily increased by, for example, easy operations such as direct application, diffusion or spraying of the stomata-increasing agent to a plant.

The contact of the stomata-increasing agent with a plant can be performed in the same way as the contact of a plant with the stomata-increasing agent with a plant in Method 1. In addition, the amount of the stomata-increasing agent to be contacted to a plant and time for contacting a plant with the stomata-increasing agent are similar to the amount of the stomata-increasing agent to be contacted to a plant and the time for contacting a plant with the stomata-increasing agent in Method 1. Further, the plant to which Method 3 is applied is similar to the plant to which Method 1 is applied.

In another aspect, the method for increasing the yield of a plant of the present invention is, a method characterized by overexpressing the polypeptide in a plant (hereinafter, referred to as "Method 4"). In Method 4, since the polypeptide is overexpressed in a plant, the number and/or density of stomata in a plant can be increased, and the amount of carbon fixation in a plant can be increased, thereby increasing the yield of the plant, as compared to a wild-type plant (wild-type strain) which does not overexpress the polypeptide.

The overexpression of the polypeptide in a plant can be performed by the method similar to the polypeptide overexpression method in Method 2. The plant to which Method 4 is applied is similar to the plant to which Method 2 is applied.

As described above, according to the method for increasing the yield of a plant of the present invention, the amount of carbon fixation in a plant can be increased to increase the yield of the plant. Therefore, the method for increasing the yield of a plant of the present invention is useful for increase in the food production, increase in the production of a useful material by a plant, and the like.

5. Method for Evaluating Stomata-Increasing Agent

In a plant, the stomata-increasing agent can be evaluated using the expression level of the polypeptide of the present invention or the amount of a nucleic acid encoding the polypeptide as an index. Specifically, a substance to be tested is brought into contact with a cell expressing the polypeptide of the present invention or a plant at least having the cell, to determine at least one of the change occurring between the expression level of the polypeptide when the substance to be tested is contacted and the expression level of the polypeptide when the substance to be tested is not contacted, and the change occurring between the amount of a nucleic acid encoding the polypeptide when the substance to be tested is contacted and the amount of a nucleic acid encoding the polypeptide when the substance to be tested is not contacted.

Here, the substance to be tested is not particularly limited, and includes an inorganic compound, an organic compound, an extract of a plant or a microorganism, an animal metabolite, a microorganism culture and the like. The substance to be tested can be used as it is or after dissolving in a solvent as necessary. The solvent is preferably a solvent having no effect on the determination of the physiological events. The solvent includes, for example, a physiological saline, water and the like.

The contact of the substance to be tested with the cell can be performed, for example, by culturing the cell in the medium containing the substance to be tested. In addition, the contact of a substance to be tested with the plant is performed by immersion of the plant in a solution containing the substance to be tested, by direct application, diffusion, spraying or the like of the substance to be tested to the leaf, the stem, the calyx, the anther and the like of the plant, and the like.

The medium can be a medium containing a component suitable for growing the cell or plant (for example, glucose, amino acid, peptone, vitamin and the like). The medium can be a medium obtained by supplementing the component to the conventional basal medium or a commercially available medium. The culture medium can be appropriately selected depending on the types of cells and plants.

In addition, the solvent which constitutes the solution includes a buffer suitable for maintaining the cell or a plant, and the like.

The amount of the substance to be tested contacted to a plant can be appropriately selected depending on the types of the substance to be tested.

The expression level of the polypeptide can be determined, for example, by performing western blotting, ELISA and the like, using an antibody binding to the polypeptide. In addition, the amount of the nucleic acid can be determined by southern blotting or northern blotting using a probe prepared based on the nucleic acid, by real-time PCR using a primer pair prepared based on the nucleic acid, and the like.

In the method for evaluating the stomata-increasing agent, the substance to be tested can be evaluated as a stomata-increasing agent in each of cases where the expression level of the polypeptide when the substance to be tested is contacted is higher than the expression level of the polypeptide when the substance to be tested is not contacted, and where the amount of a nucleic acid encoding the polypeptide when the substance to be tested is contacted is larger than the amount of a nucleic acid encoding the polypeptide when the substance to be tested is not contacted.

EXAMPLES

Hereinafter, the present invention will be more specifically on the basis of examples, but the present invention is not intended to be restricted by the examples.

Incidentally, in the following examples, a polypeptide comprising the amino acid sequence shown in SEQ ID NO: 6 is also described as "stomagen". In addition, a gene encoding the stomagen is also described as a "stomagen gene". Furthermore, a polypeptide which is a precursor of the polypeptide comprising the amino acid sequence shown in SEQ ID NO: 6 (SEQ ID NO: 1) may be described as "stomagen" for convenience.

Example 1

Gene Search by Computer (in Silico Screening)

Gene search was performed by computer using transcriptome database of *Arabidopsis thaliana*, ATTED-II (web page address: http://atted.jp/) and "NetworkDrawer" in Tool of ATTED-II as a program, to study genes co-expressed with each of TMM gene, SDD1 gene and EPF1 gene. Gene search was conducted by performing the steps of selecting {Execute}, {MR-rank method} and {top 300 genes in 22,263 genes} in Function 3, inputting three genes of At1g80080 (TMM gene), At1g04110 (SDD1 gene) and At2g20875 (EPF1 gene), and performing analysis in "submit".

Based on the analysis result, a gene of which function was unknown, EPFL9 gene (At4g12970) belonging to the EPF family (stomagen gene), was focused.

Preparation Example 1

Primer Design

Primers used in the following examples and nucleotide sequences thereof are shown in Table 1.

TABLE 1

| Purpose | Primer Name | Nucleotide Sequence (Direction from 5' end to 3' end) | SEQ ID NO |
|---|---|---|---|
| Stomagen Promoter Cloning | P10_prom_F P10_prom_R | CACCTAGAAAAGATTTGCTTCCTAAAC TCTCTACTTCTTCTTCTTCTTGCTC | 7 8 |
| Stomagen Coding Region Cloning | P10_F P10_R | CACCGAATGAAGCATGAAATGATGAACATC ACAACTATTATCTATGACAAACACATCTA | 9 10 |
| EPF1 Coding Region Cloning | EPF1_F EPF1_R | CACCATGAAGTCTC TTCTTCTCCT TGCCTT TCAAGGGACAGGGTAGGACTTATTGTT | 11 12 |

TABLE 1-continued

| Purpose | Primer Name | Nucleotide Sequence (Direction from 5' end to 3' end) | SEQ ID NO |
|---|---|---|---|
| GFP Amplification | GFP-CfusF Bst | ATAGGTCACCTGGTGGTGGTGGTATTGAAGGTAGAAGTAAAGGAGAAGAACTTTTC | 13 |
|  | GFP-CfusR Bst | TATGGTTACCTTAATGGTGATGGTGATGGTGATGGTGTTTGTATAGTTCATCCATGC | 14 |
| Venus-g4 Tag Fusion To C-Terminal Of Stomagen | P-V_F | TGTGTTTGTCATAGAATGGTGAGCAAGGGC | 15 |
|  | P-V_R | GCCCTTGCTCACCATTCTATGACAAACACA | 16 |
|  | Venus_R | TTACCCCCCCCCCCCTTGTACAGC | 17 |
| Secretory Venus-g4 | 2Ssp_F | CACCatggccagactcacaagcatcattgccctct | 18 |
|  | 2Ssp<--p10m | ATCATATGGGTGCGGTAGGCGTACGCATCT | 19 |
|  | 2Ssp-->p10m | ACCGCACCCATATGATAGGGTCGACAGCAC | 20 |
| Reconbinant Stomagen Production By E.coli | P10m_F | caccCATATGATAGGGTCGACAGCACCAAC | 21 |
| Stomagen Silencing By Artificial MacroRNA | CACC_amiA | CACCCTGCAAGGCGATTAAGTTGGGTAAC | 22 |
| For amiA | P10ami1_I miR-s | gaTACATCTAaAATGATAAGCGCtctctcttttgtattcc | 23 |
|  | P10ami1_II miR-a | gaGCGCTTATCATTATAGATGTAtcaaagagaatcaatga | 24 |
|  | P10ami1_III miR*s | gaGCACTTATCATTAAAGATGTTtcacaggtcgtgatatg | 25 |
|  | P10ami1_IV miR*a | gaAACATCTTTAATGATAAGTGCtctacatatatattcct | 26 |
| For amiB | P10ami2_ImiR-s | gaTACATCTATAATGATAAGCGCtctctcttttgtattcc | 27 |
|  | P10ami2_IImiR-a | gaGCGCTTATCATTATAGATGTAtcaaagagaatcaatga | 28 |
|  | P10ami2_IIImiR*s | gaGCACTTATCATTAAAGATGTTtcacaggtcgtgatatg | 29 |
|  | P10ami2_IVmiR*a | gaAACATCTTTAATGATAAGTGCtctacatatatattcct | 30 |
|  | amiB | GCGGATAACAATTTCACACAGGAAACAG | 31 |
| Stomagen Silencing By dsRNA | P10_RNAi_F | CACCGATAGGGTCGACAGCACCAA | 32 |
|  | P10_RNAi_R | TCATATCTATGACAAACACATCTATAA | 33 |
| Genotyping Primer | tmm SALK_011958-LP | ATGGCACGATATGAATTCTTCCGCCAA | 34 |
|  | SALK_011958-RP | ACTAGATATTAGCATAAAAATGAAATTAGG | 35 |
|  | epf1SALK_137549-LP | TTTTTCATTATTCGCTTAAAGTGTAG | 36 |
|  | SALK_137549-RP | AGCAAAAGGAAAACAAAACGG | 37 |
|  | epf2SALK_047918-LP | TAAAACCTCTGCCTCAACCAG | 38 |
|  | SALK_047918-RP | TTACCGGTATGATGGAGATGG | 39 |
|  | sph SAIL_36_B6 LP | GAAAAACCTAGATCCTCCCCC | 40 |
|  | SAIL_36_B6_RP | TCCTATGATCGATGCTTGGTC | 41 |

Here, primer CACC_amiA, primer P10ami1_I miR-s, primer P10ami1_II miR-a, primer P10ami1_III miR*s, primer P10ami1_IV miR*a, primer P10ami2_ImiR-s, primer P10ami2_IImiR-a, primer P10ami2_IIImiR*s, primer P10ami2_IVmiR*a and primer amiB are primers for preparing a sequence forming a hairpin structure containing artificial micro RNA for silencing the expression of a stomagen gene (gene number At4g12970). The artificial micro RNA targets the coding region at the 3' terminus of a stomagen gene. For designing of the artificial micro RNA, micro RNA designing program WMD2 {web address: http://wmd2.weigelworld.org/cgi-bin/mirnatools.pl} was used.

Preparation Example 2

Preparation of Antibody Against Stomagen

Using a genomic DNA of *Arabidopsis thaliana* Col-0 line (CS60000) {wild-type strain} as a template, the primer P10_F and primer P10_R shown in Table 1, a region encoding stomagen was amplified by PCR. Thereafter, the resulting PCR product was inserted into a vector {vector derived from pET32 (manufactured by Novagen) (see Literature 23)}. The resulting construct was introduced into *Escherichia coli* BL21 line, to express stomagen.

The expression product of the *E. coli* was subjected to affinity chromatography using an affinity column {manufactured by GE Healthcare, trade name: Hi-Trap chelating column}, and thereafter subjected to chromatography using an anion-exchange column {manufactured by GE Healthcare, trade name: H-SP}, thereby purifying a recombinant protein (stomagen).

Next, a rabbit was injected with the resulting purified product according to Literature 26. Thereafter, serum of the rabbit was collected. From the resulting serum, an antibody against stomagen (hereinafter, referred to as an "anti-stomagen antibody") was obtained.

Preparation Example 3

Expression of Recombinant Protein Using Tobacco-Cultured BY-2 Cells

A fusion protein of stomagen and green fluorescent protein (hereinafter, referred to as "GFP") (hereinafter, referred to as "stomagen-GFP") and a fusion protein of EPF1 and GFP (hereinafter, referred to as "EPF1-GFP") were prepared using a tobacco-cultured cell system with the Tomato mosaic virus-based expression vector and the inducible virus infection system according to the method described in Literature 20.

First, a DNA encoding stomagen was obtained by performing PCR with the use of a genomic DNA of *Arabidopsis thaliana* Col-0 line (CS60000) {wild-type strain} as a template, the primer P10_F and primer P10_R shown in Table 1. In addition, a DNA encoding GFP was obtained by performing PCR using a cDNA of GFP as a template, the primer GFP-CfusF Bst and primer GFP-CfusR Bst shown in Table 1. The DNA encoding stomagen and the DNA encoding GFP were joined to obtain a DNA construct (hereinafter, referred to as "stomagen-GFP DNA"). Next, the region of HuIFNγ gene in the Tomato mosaic virus vector pBICER8-ToMV-C0.3-HuIFNγ-SRz22 was replaced by the stomagen-GFP DNA, to obtain a vector for expressing stomagen-GFP (hereinafter, referred to as "stomagen-GFP expression vector").

In addition, a DNA encoding EPF1 was obtained by performing PCR using a genomic DNA of *Arabidopsis thaliana* Col-0 line (CS60000) {wild-type strain} as a template, the primer EPF1_F and primer EPF1_R shown in Table 1. The DNA encoding EPF1 and the DNA encoding GFP were joined to obtain a DNA construct (hereinafter, referred to as "EPF1-GFP DNA"). Next, the region of HuIFNγ gene in the Tomato mosaic virus vector pBICER8-ToMV-C0.3-HuIFNγ-SRz22 is replaced by EPF1-GFP DNA, to obtain a vector for expressing EPF1-GFP (hereinafter, referred to as "EPF1-GFP expression vector").

The resulting stomagen-GFP expression vector or EPF1-GFP expression vector was introduced into BY-2 cells having an estrogen-inducible transcription factor XVE. Thereafter, induction by β-estrogen was performed according to the method described in Literature 20. Subsequently, cells were collected and homogenized. The resulting homogenate was subjected to centrifugation at 800 rpm for 3 minutes, to give a supernatant. A fraction containing stomagen-GFP or EPF1-GFP was obtained from the resulting supernatant.

Experimental Example 1

Evaluation of Specificity of Anti-Stomagen Antibody

Figure 2:
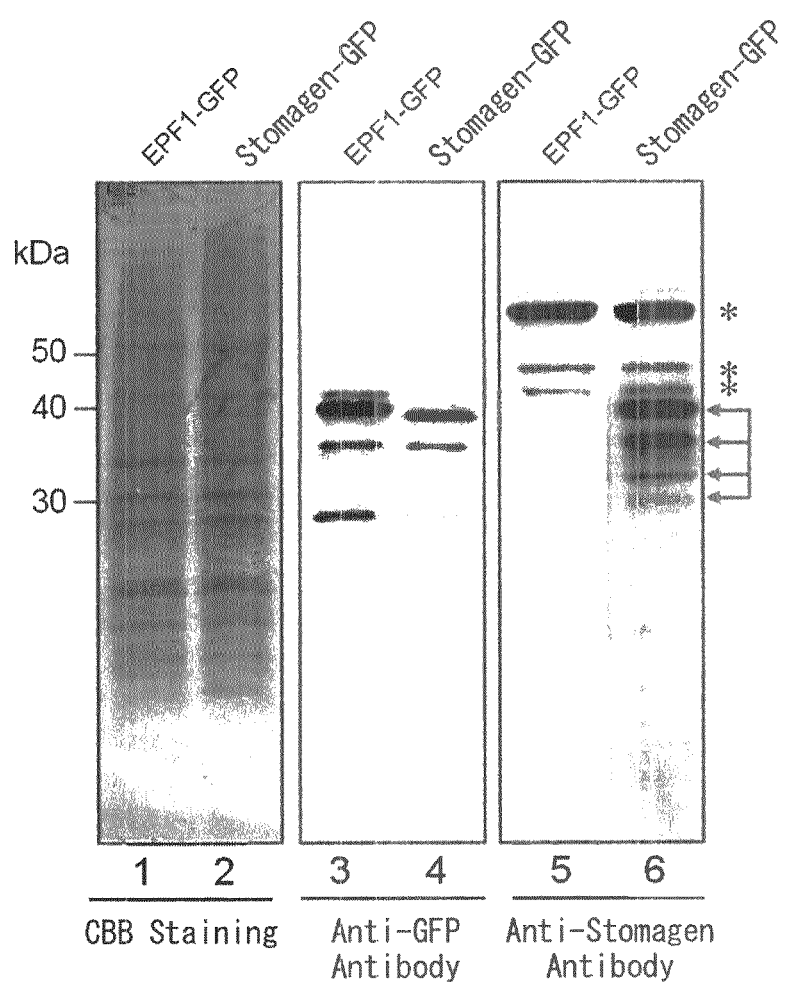
FIG. 2 is a photograph substituted for drawing showing the result of examining specificity of the anti-stomagen antibody obtained in Preparation Example 2 for stomagen.

The fraction containing stomagen-GFP and the fraction containing EPF1-GFP obtained in Preparation Example 3 were loaded on SDS-denatured polyacrylamide gel and subjected to SDS-PAGE. Using the gel after SDS-PAGE, and each of anti-stomagen antibody and anti-GFP antibody, western blotting analysis was performed according to the method described in Literature 24, to evaluate the specificity of the anti-stomagen antibody obtained in Preparation Example 2. Here, the anti-stomagen antibody was used in a concentration of 1/1000. As a secondary antibody, a horseradish peroxidase-conjugated anti-rabbit IgG-goat antibody {manufactured by GE Healthcare, trade name: NA934} was used in a concentration of 1/5000. In addition, the gel after SDS-PAGE was stained with Coomassie brilliant blue (CBB). The result of examining the specificity of the anti-stomagen antibody obtained in Preparation Example 2 is shown in FIG. 2. In the figure, an arrow represents the position of the band corresponding to stomagen-GFP, and an asterisk represents the position of the nonspecific band.

From the result shown in FIG. 2, it can be seen that the anti-stomagen antibody binds to stomagen-GFP (see lane 6 in FIG. 2) but does not bind to EPF1-GFP (see lane 5 in FIG. 2). In other words, it can be seen that the anti-stomagen antibody recognizes only stomagen-GFP and does not recognize EPF1-GFP. On the other hand, it can be seen that the anti-GFP antibody binds to both stomagen-GFP and EPF1-GFP (see lanes 3 and 4 in FIG. 2). In other words, the anti-GFP antibody recognizes both stomagen-GFP and EPF1-GFP.

Preparation Example 4

First, a vector for stomagen overexpression was prepared by carrying out the following operations with the use of a plant binary vector based on Gateway cloning technology (Invitrogen). A DNA encoding stomagen was obtained by performing PCR with the use of a genomic DNA of *Arabidopsis thaliana* Col-0 line (CS60000) as a template, the primer P10_F and primer P10_R shown in Table 1. The DNA was introduced into a vector {manufactured by Invitrogen, trade name: pENTR/D-TOPO} by using BP Clonase (manufactured by Invitrogen). Thereafter, using the resulting construct and LR Clonase, the DNA was transferred from the construct into a binary vector pB2GW7 {provided by Gent University VIB}. At this stage, a vector for stomagen overexpression was obtained.

Next, the vector for stomagen overexpression was introduced into *Agrobacterium* (strain GV3101). Subsequently, the DNA was introduced into the *Arabidopsis thaliana* Col-0 line by infecting *Arabidopsis thaliana* Col-0 line (stock number: CS60000) with the resulting *Agrobacterium*. Thereafter, the resulting *Arabidopsis thaliana* was grown, and seeds were collected. The collected seeds were seeded on a glufosinate ammonium-containing GM medium {50 μM glufosinate ammonium, 0.5% by mass MS salt, 1% by mass sucrose, 0.5% by mass MES-KOH buffer (pH 5.7), and 0.5% by mass gellan gum} and grown at 22° C. while maintaining a constant light intensity. At this stage, a glufosinate ammonium-resistant plant was selected.

The selected plants (T1) were individually grown to obtain next-generation seeds (T2). A seed obtained from 10th plant (T1) of the selected plants (T1) was used as stomagen-overexpressing line 10. A seed obtained from 2nd plant (T1) of the selected plants (T1) was used as stomagen-overexpressing line 2.

Preparation Example 5

A DNA comprising a sequence forming a hairpin structure containing an artificial micro RNA (amiRNA) was prepared by using a plasmid pRS300 for artificial micro RNA cloning {provided by Dr. Detlef Weigel} as a template, the primer CACC_amiA, primer P10ami_1 miR-s, primer P10ami1_II miR-a, primer P10ami1_III miR-*s, primer P10ami1_IV miR*a and primer amiB, and introduced into a vector {manufactured by Invitrogen, trade name: pENTR/D-TOPO}. Thereafter, the DNA was transferred from the construct into a binary vector pB2GW7 {provided by Gent University VIB} by using the resulting construct and LR Clonase. At this stage, a vector for stomagen silencing was obtained.

Next, the vector for stomagen silencing was introduced into *Agrobacterium* (strain GV3101). Subsequently, the DNA was introduced into the *Arabidopsis thaliana* Col-0 line by infecting *Arabidopsis thaliana* Col-0 line (stock number: CS60000) with the resulting *Agrobacterium*. Thereafter, the resulting *Arabidopsis thaliana* was grown, and seeds were collected. The collected seeds were seeded on a glufosinate ammonium-containing GM medium and grown at 22° C. while maintaining a constant light intensity. At this stage, a glufosinate ammonium-resistant plant was selected.

The selected plants (T1) were individually grown to obtain next-generation seeds (T2). A seed obtained from 10th plant (T1) of the selected plants (T1) was used as stomagen-silenced line 10 (STOMAGEN-RNAi). A seed obtained from 2nd plant (T1) of the selected plants (T1) was used as stomagen-silenced line 2.

Preparation Example 6

A stomagen-overexpressing pTMM::GFP line was obtained in the same operation as in Preparation Example 4, except that *Arabidopsis thaliana* pTMM::GFP line {provided by Dr. Tsuyoshi Nakagawa in Shimane University} was infected with *Agrobacterium* (strain GV3101) into which the vector for stomagen overexpression was introduced.

Test Example 1

Evaluation of Effect of Stomagen on Phenotype of Plant

Figure 3:
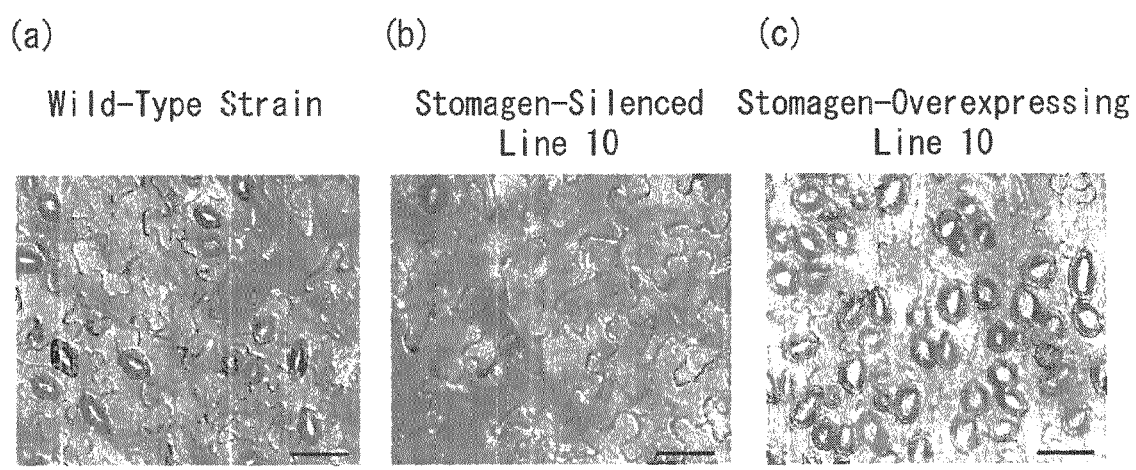
FIG. 3 (a) is a photograph substituted for drawing of a differential interference image showing the result of observing abaxial epidermis of a mature first leaf of a wild-type strain in Test Example 1, (b) is a photograph substituted for drawing of a differential interference image showing the result of observing abaxial epidermis of a mature first leaf of a stomagen-silenced line 10 in Test Example 1, and (c) is a photograph substituted for drawing of a differential interference image showing the result of observing abaxial epidermis of a mature first leaf of a stomagen-overexpressing line 10 in Test Example 1.

The mature first leaves of each of *Arabidopsis thaliana* Col-0 line (stock number: CS60000) {wild-type strain}, the stomagen-overexpressing line 10 obtained in Preparation Example 4 and the stomagen-silenced line 10 (STOMAGEN-RNAi) obtained in Preparation Example 5 were collected. Next, the first leaves were fixed in a fixing solution (ethanol: acetic acid (volume ratio)=9:1) for 7 hours or more and then made transparent in a chloral hydrate solution (chloral hydrate:water:glycerol (volume ratio)=8:2:1). After removal of chloral hydrate with water, stomata were stained with a 1 μg/mL aqueous Safranin solution {1 μg Safranin-O/ml water}. Thereafter, the abaxial epidermis of the first leaves was observed under a differential interference microscope {manufactured by Zeiss, trade name: Axioskop plus microscope}. A differential interference image showing the result of observing abaxial epidermis of the mature first leaf of the wild-type strain in Test Example 1 is shown in FIG. 3 (*a*), a differential interference image showing the result of observing abaxial epidermis of mature first leaf of the stomagen-silenced line 10 in Test Example 1 is shown in FIG. 3 (*b*), and a differential interference image showing the result of observing abaxial epidermis of the mature first leaf of the stomagen-overexpressing line 10 in Test Example 1 is shown in FIG. 3 (*c*). In the figures, a scale bar represents 50 μm.

Figure 4:
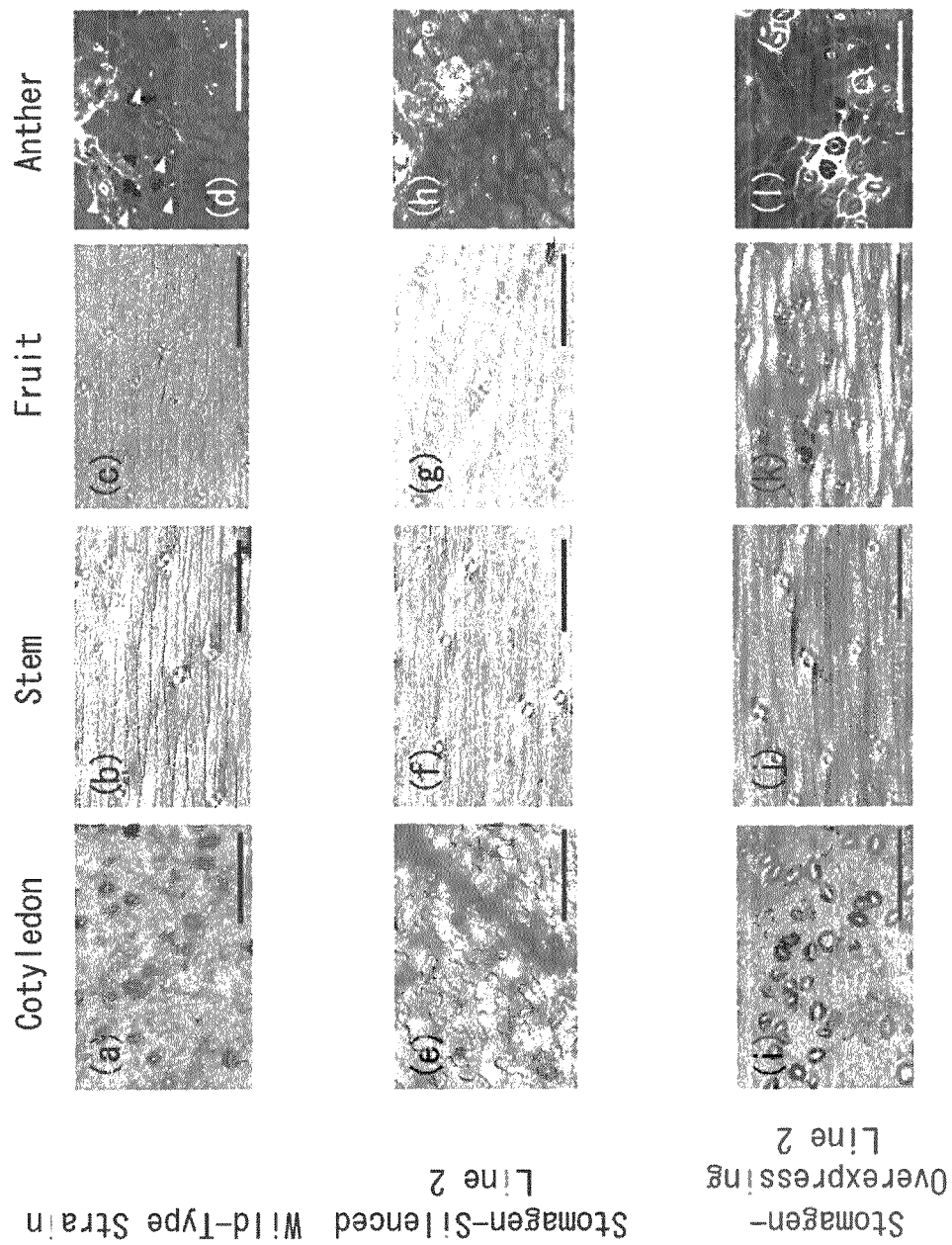
FIG. 4 shows photographs substituted for drawings of differential interference images showing the result of observing the epidermis of each of cotyledons, stems and fruits of a wild-type strain, a stomagen-silenced line 2 and a stomagen-overexpressing line 2 and confocal microscopic images showing the result of observing the epidermis of anthers thereof in Test Example 1.

In addition, the cotyledons at 23 days after germination, fully expanded second internodes, mature fruits and anthers of flower buds in the given size of each of the wild-type strain, the stomagen-overexpressing line 2 obtained in Preparation Example 4 and the stomagen-silenced line 2 obtained in Preparation Example 5 were respectively collected. Next, each of the cotyledons, stems and fruits was fixed and made transparent, and then stomata were stained, by carrying out the same operation as described above. Thereafter, the epidermis of each of the cotyledons, stems and fruits was observed under a differential interference microscope {manufactured by Zeiss, trade name: Axioskop plus microscope}. In addition, the epidermis of the anthers was observed under a confocal microscope {manufactured by Zeiss, trade name: LSM510 META microscope} and the 488-nm and 544-nm lines of a 40-mW Ar/Kr laser. Differential interference images showing the result of observing the epidermis of the cotyledons, stems and fruits of each of the wild-type strain, the stomagen-silenced line 2 and the stomagen-overexpressing line 2 in Test Example 1 and confocal microscopic images showing the result of observing the epidermis of anthers in Test Example 1 are shown in FIG. 4. In the figures, a scale bar represents 100 μm.

Figure 5:
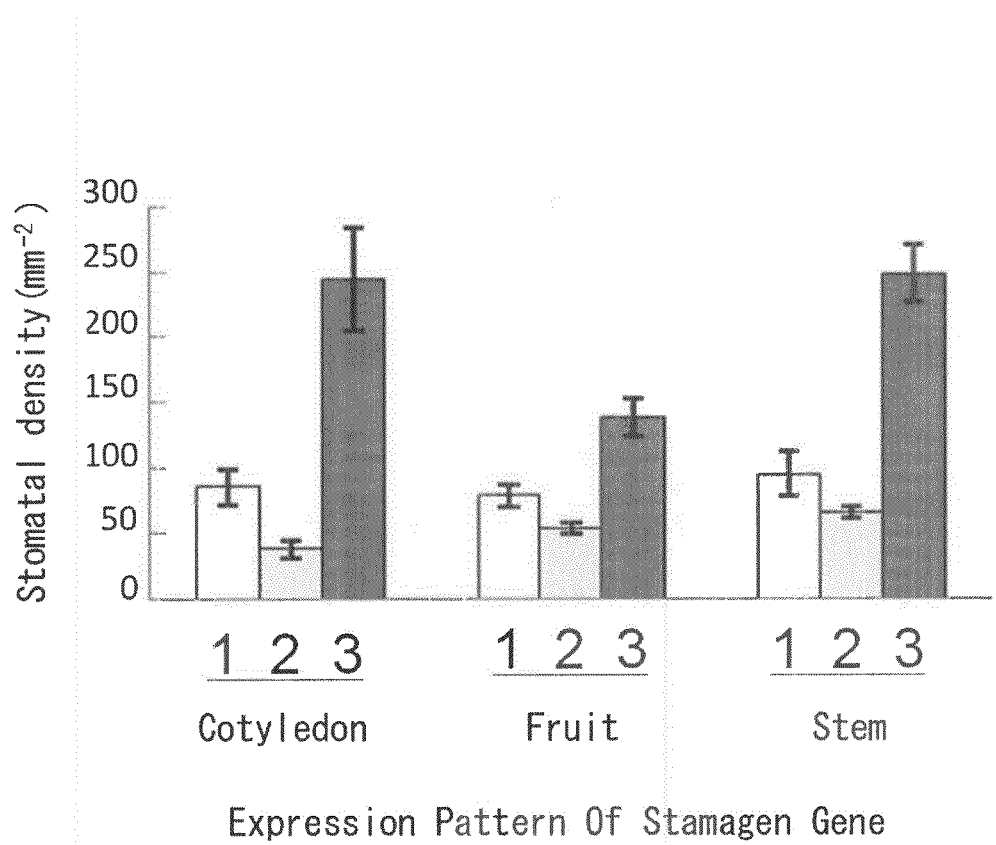
FIG. 5 is a graph showing the result of examining the relationship between an expression pattern of a stomagen gene and stomatal densities in each organ of cotyledons, fruits and stems in Test Example 1.

Moreover, the cotyledons at 23 days after germination, mature fruits or fully expanded second internodes of each of the *Arabidopsis thaliana* Col-0 line (stock number: CS60000) {wild-type strain}, the stomagen-overexpressing line 2 obtained in Preparation Example 4 and the stomagen-silenced line 2 obtained in Preparation Example 5 were each collected. Next, the surface of the cotyledons, fruits or stems was observed under a differential interference microscope {manufactured by Zeiss, trade name: Axioskop plus microscope}, to determine the number of stomata in a square area of 0.22 mm$^2$. Then, stomatal density was calculated. Here, statistical analysis was conducted using R statistical analysis software. The result of examining the relationship between an expression pattern of a stomagen gene and stomatal densities in each organ of cotyledons, fruits and stems in Test Example 1 is shown in FIG. 5. In the figures, lane 1 represents the wild-type strain, lane 2 represents the stomagen-silenced line 2, and lane 3 represents the stomagen-overexpressing line 2.

Furthermore, the cotyledons at 2.5 days after germination of each of the wild-type strain and the stomagen-overexpressing line 10 obtained in Preparation Example 4 were collected. Next, the cotyledons were stained with a fluorescent dye {manufactured by Invitrogen, trade name: FM4-64}. The epidermis of the cotyledons after staining was observed under a confocal microscope {manufactured by Zeiss, trade name: LSM510 META microscope} and the 488-nm and 544-nm lines of a 40-mW Ar/Kr laser. A confocal microscopic image showing the result of observing the abaxial epidermis of the cotyledon in the wild-type strain in Test Example 1 is shown in FIG. 6 (*a*), and a confocal microscopic image showing the result of observing the abaxial epidermis of the cotyledon in the stomagen-overexpressing line 10 in Test Example 1 is shown in FIG. 6 (*b*). In each of FIG. 6 (*a*) and FIG. 6 (*b*), the upper right figure shows the magnification of the part shown by the square in the bottom right figure. In the figures, a scale bar in a horizontal direction represents 50 μm, and a scale bar in a vertical direction represents 500 μm.

In addition, the first leaves at 5 days after germination of each of the wild-type strain and the stomagen-overexpressing pTMM::GFP line obtained in Preparation Example 6 were collected. Next, the epidermis of the first leaves was observed under a confocal microscope {manufactured by Zeiss, trade name: LSM510 META microscope} and the 488-nm and 544-nm lines of a 40-mWAr/Kr laser. Incidentally, upon observation with the confocal microscope, an excitation filter {manufactured by Zeiss, trade name: BP450-490}, a dichroic mirror {manufactured by Zeiss, trade name: FT510}, and an absorption filter {manufactured by Zeiss, trade name: BP515-565} were used. A confocal microscopic image showing the result of observing the epidermis on the first leaf in the wild-type strain in Test Example 1 is shown in FIG. 7 (*a*), and a confocal microscopic image showing the result of observing the epidermis on the first leave in the stomagen-overexpressing pTMM::GFP line in Test Example 1 is shown in FIG. 7 (*b*). In the figures, a scale bar represents 50 μm.

From the results shown in FIG. 3, FIG. 4 and FIG. 5, it can be seen that, when At4g12970 gene, i.e., the stomagen gene, is overexpressed (stomagen-overexpressing line), stomatal density increases in various organs where stomata are present (leaf, cotyledon, stem, fruit and anther) as compared to the wild-type strain and the stomagen-silenced line. Such a phenomenon was confirmed in 13 independently-established lines of T2 plants (each 7 plants). The phenotype of the stomagen-overexpressing line is a phenotype exactly opposite to the EPF1- and EPF2-overexpressing lines showing a phenotype of a decreased stomatal density (Literatures 4 to 6).

Incidentally, stomata in most dicotyledonous plants are separated by at least one "non-stomatal cell", and this pattern is thought to improve the efficiency of gas intake (Literature 12). From the results shown in FIG. 3, it can be seen that the stomagen gene-overexpressing lines are prone to exhibit many clustered stomata in the mature leaves. On the other hand, from the results shown in FIG. 6 and FIG. 7, it can be seen that satellite meristemoids (stomatal precursor cells) are adjacent to guard cells or their precursor cells in the immature cotyledons. It is considered based on these results that, since the orientation of cell division in the stomatal lineage cells is different from that of the wild-type strain, the stomagen-overexpressing line shows morphological characteristics different from those of the wild-type strain.

Test Example 2

(1) Localization of Stomagen Gene Expression

A DNA of a 2 kbp upstream region from the start codon (promoter region) for a stomagen gene (STOMAGEN) was obtained by performing PCR using a genomic DNA of *Arabidopsis thaliana* Col-0 line (CS60000) as a template, the primer P10prom_F and P10_prom_R shown in Table 1. The DNA was introduced into a vector {manufactured by Invitrogen, trade name: pENTR/D-TOPO} using BP Clonase {manufactured by Invitrogen}. Thereafter, using the resulting construct and LR Clonase, the DNA was transferred from the construct into a vector pBGWFS7 {provided by Gent University VIB}. The pBGWFS7 has a β-Glucuronidase (GUS) gene as a reporter gene for a promoter. At this stage, a vector for promoter expression was obtained.

Next, the vector for promoter expression was introduced into *Agrobacterium* (strain GV3101). Subsequently, the DNA was introduced into *Arabidopsis thaliana* Col-0 line (stock number: CS60000) by infecting the *Arabidopsis thaliana* Col-0 line with the resulting *Agrobacterium*. Thereafter, the resulting *Arabidopsis thaliana* was grown, and seeds were collected. The collected seeds were seeded on a glufosinate ammonium-containing GM medium and grown at 22° C. while maintaining a constant light intensity. At this stage, a glufosinate ammonium-resistant plant was selected.

The selected plants (T1) were individually grown to obtain next-generation seeds (T2). The resulting seeds (T2) were used as pSTOMAGEN::GUS lines. Moreover, the transverse section of the ninth leaves of a pSTOMAGEN::GUS line at 18 days after germination was prepared. Expression of GUS activity based on the promoter of a stomagen gene was examined by using the resulting transverse section. The expression of GUS activity was confirmed by performing the same operations as the GUS staining procedure described in Literature 26, except that the samples were fixed at 4° C. for 7 to 10 hours. A microscopic image showing the result of observing the transverse section of the ninth leaf of the pSTOMAGEN::GUS line at 18 days after germination in Test Example 2 is shown in FIG. 8.

Figure 8:
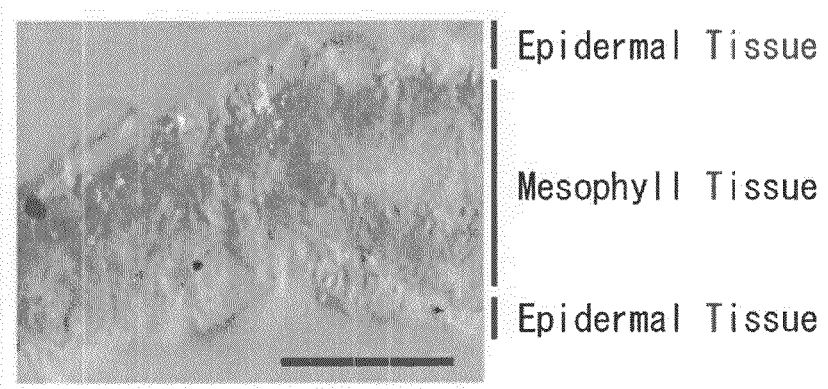
FIG. 8 is a photograph substituted for drawing of a microscopic image showing the result of observing the transverse section of the ninth leaf of a pSTOMAGEN::GUS line at 18 days after germination in Test Example 2.

From the result shown in FIG. 8, it can be seen that the expression of GUS activity based on the promoter of a stomagen gene is prone to be mainly observed in the mesophyll tissue. Therefore, this result suggests that a stomagen gene expresses in the mesophyll tissue.

(2) In Situ Hybridization

In situ hybridization was performed by using the leaves of *Arabidopsis thaliana* Col-0 line (stock number: CS60000) {wild-type strain} and a probe (sense probe) obtained by labeling cDNA (306 bp) of a stomagen gene (STOMAGEN) or probe (antisense probe) obtained by labeling an antisense strand corresponding to the cDNA. In situ hybridization was performed by the same operation as the method described in Literature 24. A microscopic image showing the result of performing in situ hybridization analysis of the leaf primordia using an antisense probe of a stomagen gene in Test Example 2 is shown in FIG. 9 (a), and a microscopic image showing the result of performing in situ hybridization analysis of the leaf primordia using a sense probe of a stomagen gene in Test Example 2 is shown in FIG. 9 (b).

From the results shown in FIG. 9 (a) and FIG. 9 (b), it can be seen that while a signal derived from a sense probe which is a control cannot be detected {see FIG. 9 (b)}, a signal derived from an antisense probe can be observed in the mesophyll tissue {see FIG. 9 (a)}.

From these results, it is considered that the morphological characteristics in a stomagen-overexpressing line observed in FIG. 6 and FIG. 7 are due to overexpression of a stomagen gene in an epidermal cell by using 35 S promoter contained in a vector used in overexpression of stomagen.

Preparation Example 7

Figure 10:
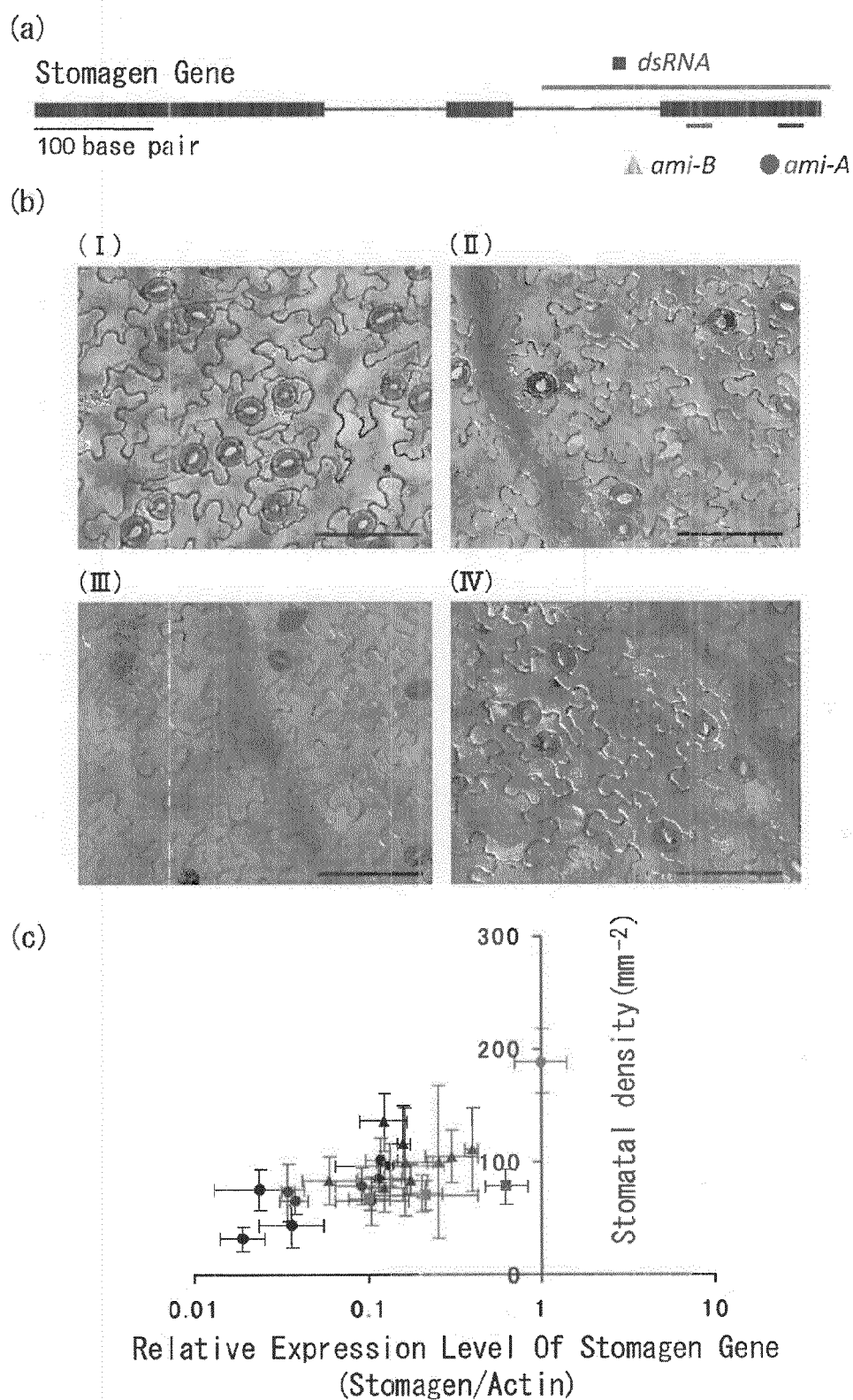
FIG. 10 (a) is a schematic view showing each location of target sequences of ami-A, ami-B and dsRNA in a nucleic acid containing a stomagen gene, (b) shows photographs substituted for drawings of differential interference images showing the result of observing the abaxial epidermis of each of mature first leaves of a wild-type strain, a stomagen-silenced line (ami-A), a stomagen-silenced line (ami-B) and a stomagen-silenced line (dsRNA) in Test Example 3, and (c) is a graph showing the result of examining the relationship between stomatal density and the relative expression level of a stomagen gene in Test Example 3.

A stomagen-silenced line (ami-B) was obtained by carrying out the same operation as in Preparation Example 5, except that the primer P10ami2_ImiR-s, primer P10ami2_IImiR-a, primer P10ami2_IIImiR*s and primer P10ami2_IVmiR*a shown in Table 1 were used in place of the primer P10ami1_I miR-s, primer P10ami1_II miR-a, primer P10ami1_III miR*s and primer P10ami1_IV miR*a shown in Table 1 in Preparation Example 5. Incidentally, in the stomagen-silenced line (ami-B), expression of stomagen is silenced by ami-B that is an artificial micro RNA. Position of the target sequence of ami-B in a nucleic acid containing a stomagen gene is as shown in FIG. 10 (a).

Preparation Example 8

A stomagen-silenced line (dsRNA) was obtained by carrying out the same operation as in Preparation Example 5, except that a genomic DNA of *Arabidopsis thaliana* Col-0 line (CS60000) was used as a template in place of the plasmid pRS300 for artificial micro RNA cloning, that the primer P10_RNAi_F and primer P10_RNAi_R shown in Table 1 were used in place of the primer CACC_amiA, primer P10ami_1 miR-s, primer P10ami1_II miR-a, primer P10ami1_III miR-*s, primer P10ami1_IV miR*a and primer amiB shown in Table 1, and that a vector pB2GWI (2)WG7 {provided by Gent University VIB} was used in place of the binary vector pB2GW7 {provided by Gent University VIB} in Preparation Example 5. Incidentally, in the stomagen-silenced line (dsRNA), expression of stomagen is silenced by dsRNA. Position of the target sequence of dsRNA in the nucleic acid containing a stomagen gene is as shown in FIG. 10 (a).

Test Example 3

The mature first leaves of each of *Arabidopsis thaliana* Col-0 line (stock number: CS60000) {wild-type strain}, the stomagen-silenced line (stomagen-silenced line 10, also referred to as "ami-A") obtained in Preparation Example 5, the stomagen-silenced line (ami-B) obtained in Preparation Example 7, and the stomagen-silenced line (dsRNA) obtained in Preparation Example 8 were collected. Subsequently, the first leaves were fixed and made transparent, and then stomata were stained, by carrying out the same operation as in Test Example 1. Thereafter, the abaxial epidermis of the first leaves was observed under a differential interference microscope {manufactured by Zeiss, trade name: Axioskop plus microscope}. Differential interference images showing the result of observing the abaxial epidermis of each of the mature first leaves of the wild-type strain, the stomagen-silenced line (ami-A), the stomagen-silenced line (ami-B) and the stomagen-silenced line (dsRNA) in Test Example 3 are shown in FIG. 10 (b). In FIG. 10 (b), (I) shows the wild-type strain, (II) shows the stomagen-silenced line (ami-A), (III) shows the stomagen-silenced line (ami-B) and (IV) shows the stomagen-silenced line (dsRNA). In FIG. 10 (b), a scale bar represents 50 µm.

The first leaves at 5 days after germination of each of *Arabidopsis thaliana* Col-0 line (stock number: CS60000) {wild-type strain}, the stomagen-silenced line (ami-A) obtained in Preparation Example 5, the stomagen-silenced line (ami-B) obtained in Preparation Example 7, and the stomagen-silenced line (dsRNA) obtained in Preparation Example 8 were collected. Next, the surface of the first leaves was observed under a differential interference microscope {manufactured by Zeiss, trade name: Axioskop plus microscope}, to determine the number of stomata in a square area of 0.22 mm$^2$. Then, stomatal density was calculated. Here, statistical analysis was conducted by using R statistical analysis software. Furthermore, the expression levels of a stomagen gene in the first leaves at 5 days after germination of each of *Arabidopsis thaliana* Col-0 line (stock number: CS60000) {wild-type strain}, 12 independent lines of the stomagen-silenced line (ami-A) obtained in Preparation Example 5, 12 independent lines of the stomagen-silenced line (ami-B) obtained in Preparation Example 7, and 4 independent lines of the stomagen-silenced line (dsRNA) obtained in Preparation Example 8 were determined. In addition, the expression level of an actin 8 gene in the first leaf was determined as a control. Determination of the expression level was performed by real-time PCR using a kit for real-time PCR {manufactured by Life Technologies, trade name: 7500 Fast Real-Time PCR system} and a kit for gene expression assay {manufactured by Life Technologies, trade name: TaqMan gene expression assay kit}. The number of used TaqMan probe was At02219575_g1 for determination of the expression level of a stomagen gene and At02270958_gH for determination of the expression level of an actin 8 gene. Moreover, the relative expression level of a stomagen gene for an actin 8 gene was calculated. The threshold cycle method was used for relative quantification (Literature 25). The result of examining the relationship between stomatal density and the relative expression level of a stomagen gene in Test Example 3 is shown in FIG. 10 (c). In FIG. 10 (c), a closed circle represents the stomagen-silenced lines (ami-A), a closed triangle represents the stomagen-silenced lines (ami-B) and a square represents the stomagen-silenced lines (dsRNA). In addition, in FIG. 10 (c), the wild-type strain shows a relative expression level of 1. An error bar represents standard deviation.

From the result shown in FIG. 10 (b), it can be seen that the mature first leaves of each of the stomagen-silenced line (ami-A), the stomagen-silenced line (ami-B) and the stomagen-silenced line (dsRNA) show the same phenotypes as the stomagen-silenced line 10 shown in FIG. 3. In addition, from the result shown in FIG. 10 (c), it can be seen that stomatal density is very low in the stomagen-silenced line (ami-A), the stomagen-silenced line (ami-B) and the stomagen-silenced line (dsRNA) having a relative expression level of a stomagen gene of less than 1, as compared to the wild-type strain having a relative expression level of a stomagen gene of 1. These results suggest that a stomagen gene is necessary for stomatal development.

Test Example 4

Figure 11:
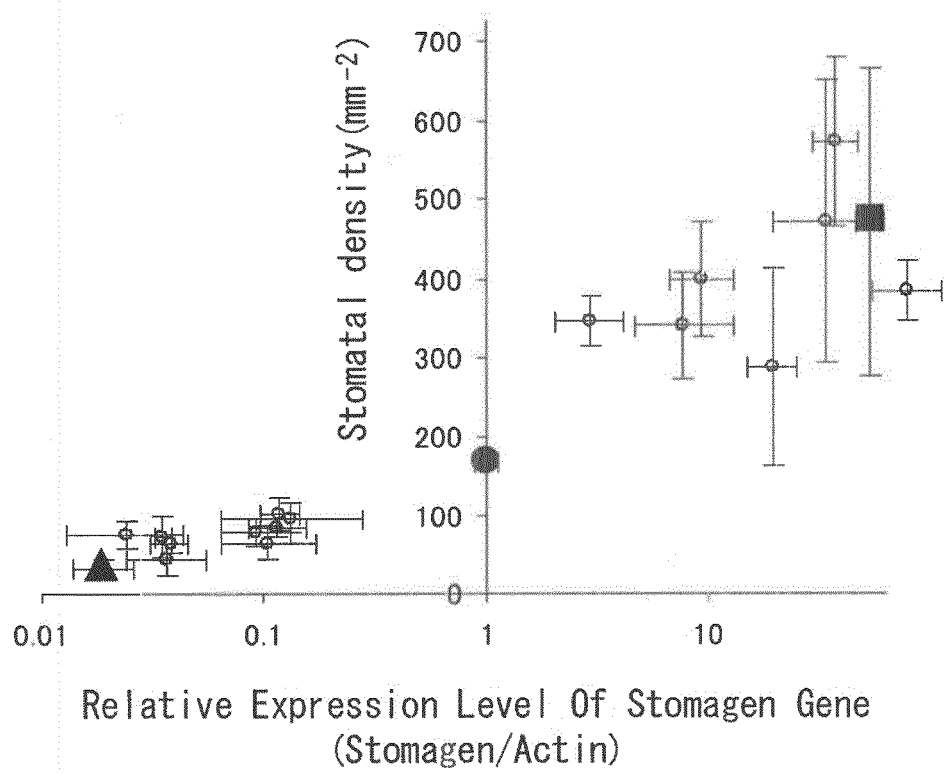
FIG. 11 is a graph showing the result of examining the relationship between stomatal density and the relative expression level of a stomagen gene in Test Example 4.

The mature first leaves at 23 days after germination of each of *Arabidopsis thaliana* Col-0 line (stock number: CS60000) {wild-type strain}, the stomagen-overexpressing line 10 obtained in Preparation Example 4, and the stomagen-silenced line 10 obtained in Preparation Example 5 were collected. Next, the surface of the first leaves was observed under a differential interference microscope {manufactured by Zeiss, trade name: Axioskop plus microscope}, to determine the number of stomata in a square area of 0.22 mm$^2$. Then, stomatal density was calculated. Here, statistical analysis was conducted using R statistical analysis software. In addition, the relative expression levels of a stomagen gene in the mature first leaves at 23 days after germination of each of the wild-type strain, the stomagen-overexpressing line 10, and the stomagen-silenced line 10 were determined. The result of examining the relationship between stomatal density and the relative expression level of a stomagen gene in Test Example 4 is shown in FIG. 11. In the figure, a circle represents the wild-type strain, a triangle represents the stomagen-silenced lines 10 and a square represents the stomagen-overexpressing lines 10. An error bar represents standard deviation.

In addition, the abaxial epidermis of the mature first leaves at 23 days after germination of each of the wild-type strain, the stomagen-overexpressing line 10 and the stomagen-silenced line 10 was observed under a differential interference microscope {manufactured by Zeiss, trade name: Axioskop plus microscope}, to determine the number of stomata and the number of epidermal cells. Moreover, the stomatal index {Number of Stomata/(Number of Stomata+Number of Epidermal Cells} was calculated. The result is shown in Table 2.

TABLE 2

|  | Stomagen expression level | Stomatal density (mm$^{-2}$) | Stomatal index (%) |
| --- | --- | --- | --- |
| Wild type | 1.0 ± 0.11 | 174.4 ± 24.5 | 32.9 ± 4.45 |
| Stomagen-silenced line | 0.07 ± 0.04 | 71.9 ± 15.1 | 17.4 ± 5.19 |
| Stomagen-overexpressing line | 30.1 ± 25.8 | 408.9 ± 91.5 | 50.9 ± 12.1 |

From the results shown in FIG. 11 and Table 2, it can be seen that there is a positive correlation between the expression level of a stomagen gene and the stomatal density or stomatal index.

Therefore, these results suggest that a stomagen gene is a positive regulator of the stomatal differentiation.

Test Example 5

RNA was extracted from a root, a leaf or a stem of *Arabidopsis thaliana* Col-0 line (stock number: CS60000) at each of 9 days (immature stage) and 23 days (mature stage) after germination according to the method described in Literature 24. In addition, RNA was extracted from each of an immature flower bud and an immature fruit of the *Arabidopsis thaliana* Col-0 line (stock number: CS60000) according to the method described in Literature 24.

Figure 12:
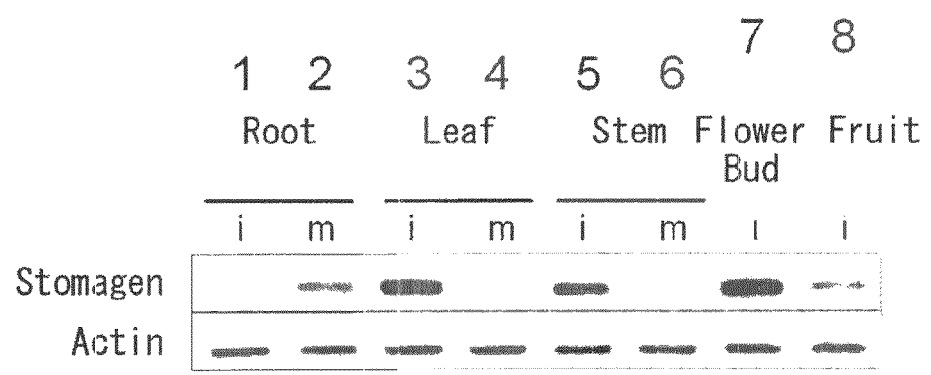
FIG. 12 is a photograph substituted for drawing of an electropherogram showing the result of examining the presence or absence of the expressions of stomagen genes in each of a root, a leaf, a stem, a flower bud and a fruit in Test Example 5.

RT-PCR was performed by the same operation as in Test Example 3 using the resulting RNA as a template. Moreover, the presence or absence of the expression of a stomagen gene in each of the root, the leaf, the stem, the flower bud and the fruit was examined by agarose gel electrophoresis. Incidentally, an actin gene was used as an internal control. The electropherogram showing the result of examining the presence or absence of the expression of stomagen genes in each of the root, the leaf, the stem, the flower bud and the fruit in Test Example 5 is shown in FIG. 12. In the figure, "i" represents immature stage and "m" represents mature stage.

From the result shown in FIG. 12, it can be seen that a stomagen gene mainly expresses in the organ such as a leaf, a stem and a flower bud at immature stage.

Test Example 6

Figure 13:
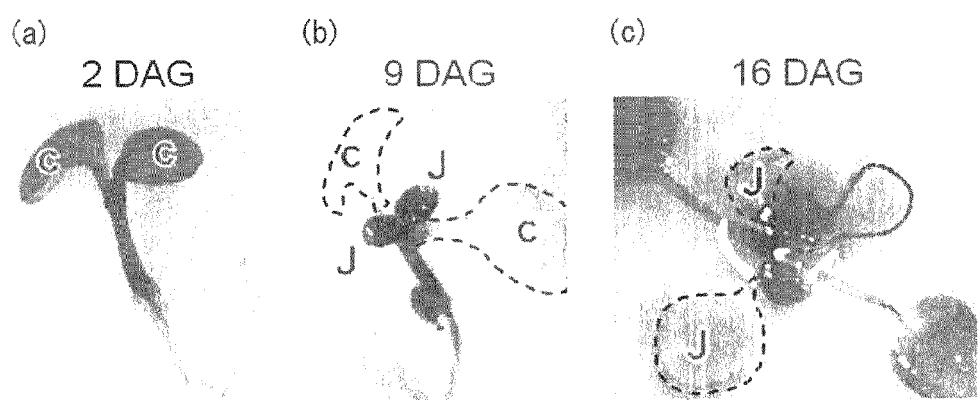
FIG. 13 (a) is a photograph substituted for drawing showing the result of analyzing an expression of a promoter of a stomagen gene in pSTOMAGEN::GUS line at 2 days after germination in Test Example 6, (b) is a photograph substituted for drawing showing the result of analyzing an expression of a promoter of a stomagen gene of a pSTOMAGEN::GUS line at 9 days after germination in Test Example 6, and (c) is a photograph substituted for drawing showing the result of analyzing an expression of a promoter of a stomagen gene in a pSTOMAGEN::GUS line at 16 days after germination in Test Example 6.

The presence or absence of the expression of GUS activity in the immature cotyledons and young leaves of pSTOMAGEN::GUS line at 2 days, 9 days or 16 days after germination prepared in Test Example 2 was examined. The result of analyzing the expression of a promoter of a stomagen gene in pSTOMAGEN::GUS line at 2 days after germination in Test Example 6 is shown in FIG. 13 (a), the result of analyzing the expression of a promoter of a stomagen gene in pSTOMAGEN::GUS line at 9 days after germination in Test Example 6 is shown in FIG. 13 (b), and the result of analyzing the expression of a promoter of a stomagen gene in pSTOMAGEN::GUS line at 16 days after germination in Test Example 6 is shown in FIG. 13 (c). In the figures, "C" represents a cotyledon and "J" represents a young leaf.

From the results shown in FIG. 13, it can be seen that, while GUS activity was confirmed in the immature cotyledons and leaves in pSTOMAGEN::GUS, GUS activity comes not to be observed once the development sufficiently proceeds. In addition, such a phenomenon is consistent with the result shown in FIG. 12. These expression patterns are consistent with the fact that stomatal development proceeds in the organs at an immature stage (Literature 2). In addition, surprisingly, GUS activity based on the promoter of a stomagen gene was detected in the mesophyll tissues but was not detected in the epidermal tissues where stomata differentiate (see FIG. 8). In addition, in situ RNA hybridization analysis gave the same result (see FIG. 9).

It can be inferred from these results that stomagen is produced in the mesophyll tissues and regulates stomatal development as a signal transmitted to the epidermis. It can be seen that an expression pattern of a stomagen gene (STOMAGEN) provides a counter example to the report that most genes involved in stomatal development are expressed specifically in the epidermal tissues (Literatures 10, 13 and 14).

Preparation Examples 9 to 11

A DNA encoding Venus with 4 glycines at its C terminus (Venus-G4), a DNA encoding a signal peptide (SP) for pumpkin 2S albumin and a DNA encoding an open reading frame of a stomagen gene without its stop codon were each prepared by PCR. Incidentally, for the preparation of the DNA encoding Venus with 4 glycines at its C terminus (Venus-G4), the primer P10_F, P-V_F, primer P-V_R and primer Venus_R shown in Table 1 were used. For the preparation of a DNA encoding a signal peptide for pumpkin 2S albumin, primer 2Ssp_F, 2Ssp<-p10m, 2Ssp->p10m and P10_R were used (see Literature 22).

A stomagen-Venus fusion gene was prepared by ligating the DNA encoding Venus-G4, the DNA encoding a signal peptide and the DNA encoding an open reading frame of a stomagen gene without its stop codon by primer extension. The resulting fusion gene was introduced into a vector {manufactured by Invitrogen, trade name: pENTR/D-TOPO}. Thereafter, the DNA was transferred from the construct into a vector pB2GW7 {provided by Gent University VIB} using the resulting construct and LR Clonase. At this stage, a vector for stomagen-Venus expression was obtained.

The resulting vector for stomagen-Venus expression was introduced into *Agrobacterium* (strain GV3101). The DNA was introduced into the *Arabidopsis thaliana* Col-0 line (stock number: CS60000) by infecting *Arabidopsis thaliana* Col-0 line with the resulting *Agrobacterium*. Thereafter, the resulting *Arabidopsis thaliana* was grown, and seeds were collected. The collected seeds were seeded on a glufosinate ammonium-containing GM medium and grown at 22° C. while maintaining a constant light intensity. At this stage, a glufosinate ammonium-resistant plant was selected. The selected plants (T1) were individually grown to obtain next-generation seeds (T2). Among the T2 seeds, those having living plants:dead plants (number ratio)=3:1 when seeded on a glufosinate ammonium-containing GM medium and grown at 22° C. while maintaining a constant light intensity were selected, to collect next-generation seeds (T3 seeds). Next, among the T3 seeds, lines in which all plants survive (homo plants) when seeded on a glufosinate ammonium-containing GM medium and grown at 22° C. while maintaining a constant light intensity was established. The resulting plants are used as stomagen-Venus-expressing lines (Preparation Example 9).

In addition, a DNA encoding STOMAGEN* (polypeptide obtained by adding a signal peptide to the N-terminus of mature stomagen) was obtained by ligating the DNA encoding a signal peptide and the DNA encoding an open reading frame of a stomagen gene without its stop codon by primer extension. Thereafter, a STOMAGEN*-expressing line (Preparation Example 10) was obtained by carrying out the same operation as described above, except that the DNA encoding STOMAGEN* was used in place of the stomagen-Venus fusion gene.

Furthermore, a DNA encoding a fusion product of the signal peptide and Venus (SP-Venus) was obtained by ligating the DNA encoding a signal peptide and the DNA encoding Venus-G4 were linked by primer extension. An SP-Venus-expressing line (Preparation Example 11) was obtained by carrying out the same operation as described above, except that the DNA encoding SP-Venus was used in place of the stomagen-Venus fusion gene.

Test Example 7

Figure 14:
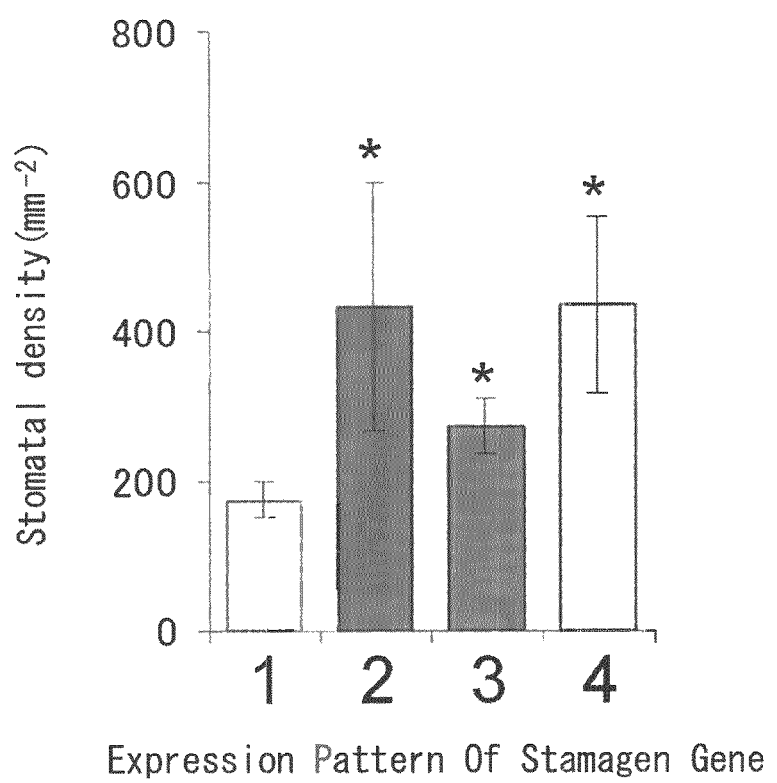
FIG. 14 is a graph showing the result of examining the relationship between an expression pattern of a stomagen gene and stomatal density in Test Example 7.

The first leaves at 23 days after germination of each of *Arabidopsis thaliana* Col-0 line (stock number: CS60000) {wild-type strain}, the stomagen-overexpressing line 10 obtained in Preparation Example 4, the STOMAGEN*-expressing line obtained in Preparation Example 10 and the stomagen-Venus-expressing line obtained in Preparation Example 9 were collected. The surface of the first leaves was observed under a differential interference microscope {manufactured by Zeiss, trade name: Axioskop plus microscope}, to determine the number of stomata in a square area of 0.22 mm². Then, stomatal density was calculated. Here, statistical analysis was conducted using R statistical analysis. In addition, two-tailed student's t-test was conducted. The result of examining the relationship between an expression pattern of a stomagen gene and stomatal density in Test Example 7 is shown in FIG. 14. In the figure, lane 1 represents the wild-type strain, lane 2 represents the stomagen-overexpressing line 10, lane 3 represents the STOMAGEN*-expressing line and lane 4 represents the stomagen-Venus-expressing line. In addition, in the figure, an error bar represents standard deviation, and an asterisk represents that the p-value is less than 0.01 as compared to the wild-type strain.

From the result shown in FIG. 14, it can be seen that the STOMAGEN*-expressing line obtained in Preparation Example 10 and the stomagen-Venus-expressing line obtained in Preparation Example 9 show the same phenotype as the stomagen-expressing line.

Test Example 8

The cotyledons of the stomagen-Venus-expressing line at 3 days after germination obtained in Preparation Example 9 were treated with desalted water or 0.8 M mannitol. The treated cotyledons were stained with a fluorescent dye {manufactured by Invitrogen, trade name: FM4-64}.

Figure 15:
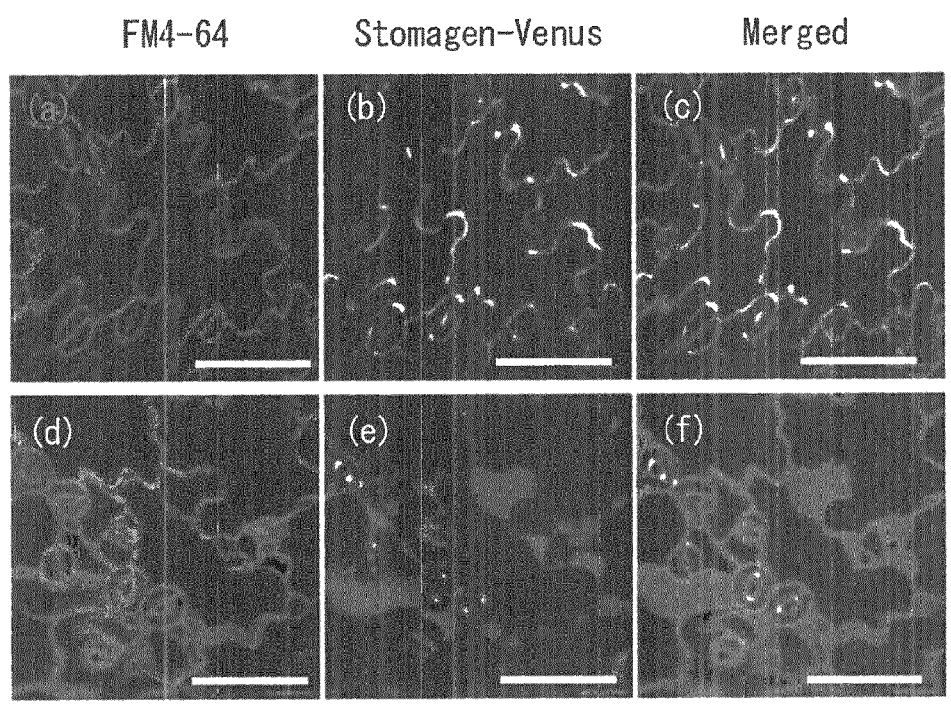
FIG. 15 shows photographs substituted for drawings of confocal microscopic images showing the result of observing abaxial epidermis of cotyledons at 3 days after germination of a stomagen-Venus-expressing line stained with FM4-64 in Test Example 8.

The abaxial epidermis of the cotyledons of the stomagen-Venus-expressing line at 3 days after germination stained with FM4-64 was observed under a confocal microscope. In this time, for the detection of fluorescence based on Venus, an excitation filter {manufactured by Zeiss, trade name: BP450-490}, a dichroic mirror {manufactured by Zeiss, trade name: FT510}, and an absorption filter {manufactured by Zeiss, trade name: BP515-565} were used. In addition, for the detection of fluorescence based on FM4-64, an excitation filter {manufactured by Zeiss, trade name: BP515-560}, a dichroic mirror {manufactured by Zeiss, trade name: FT510}, and an absorption filter {manufactured by Zeiss, trade name: BP515-565} were used. Confocal microscopic images showing the result of observing abaxial epidermis of cotyledons at 3 days after germination of a stomagen-Venus-expressing line stained with FM4-64 in Test Example 8 are shown in FIG. 15. In the figures, (*a*), (*b*) and (*c*) show the cotyledons treated with desalted water, and (*d*), (*e*) and (*f*) show the cotyledons treated with 0.8 M mannitol. In addition, in the figures, (*a*) and (*d*) show the result of detecting fluorescence based on FM4-64, (*b*) and (*e*) show the result of detecting fluorescence based on Venus, and (*c*) and (*f*) show the merged image of the result of detecting fluorescence based on FM4-64 and the result of detecting fluorescence based on Venus.

Abaxial epidermis of cotyledons at 3 days after germination was observed by carrying out the same operation as described above, except that the SP-Venus line obtained in Preparation Example 11 or Lti6b-GFP line (provided by Stanford University, Dr. Cris Somerville) was used in place of the stomagen-Venus-expressing line obtained in Preparation Example 9. Incidentally, for the detection of fluorescence based on GFP, an excitation filter {manufactured by Zeiss, trade name: BP450-490}, a dichroic mirror {manufactured by Zeiss, trade name: FT510}, and an absorption filter {manufactured by Zeiss, trade name: BP515-565} were used. Confocal microscopic images showing the result of observing abaxial epidermis of cotyledons at 3 days after germination of the SP-Venus-expressing line stained with FM4-64 in Test Example 8 are shown in FIG. 16 (A), and confocal microscopic images showing the result of observing abaxial epidermis of cotyledons at 3 days after germination of the Lti6b-GFP line stained with FM4-64 in Test Example 8 are shown in FIG. 16 (B). In FIG. 16 (A) and FIG. 16 (B), (*a*), (*b*) and (*c*) are the cotyledons treated with desalted water, and (*d*), (*e*) and (*f*) are the cotyledons treated with 0.8 M mannitol. In addition, in FIG. 16 (A), (*a*) and (*d*) show the result of detecting fluorescence based on FM4-64, (*b*) and (*e*) show the result of detecting fluorescence based on Venus, and (*c*) and (*f*) show the merged image of the result of detecting fluorescence based on FM4-64 and the result of detecting fluorescence based on Venus. In FIG. 16 (B), (*a*) and (*d*) show the result of detecting fluorescence based on FM4-64, (*b*) and (*e*) show the result of detecting fluorescence based on GFP, and (*c*) and (*f*) show the merged image of the result of detecting fluorescence based on FM4-64 and the result of detecting fluorescence based on GFP.

From the results shown in FIG. 15 and FIG. 16, it can be seen that fluorescence of Venus is observed outside the plasmolyzed cells. This result suggests that stomagen is secreted from the cells to the apoplast. Conventionally, when thinking about "mesophyll-epidermis interaction", the conventional findings entirely focus on the morphological matter whether or not there is a relationship between the positions of the airspace in the mesophyll tissues and stomata (Literatures 12 and 15). However, according to the findings described above of the present inventors, there is provided a novel and important insight that stomatal density is regulated by epidermis-mesophyll interaction.

Example 2

A product obtained by homogenizing 7 g of *Arabidopsis thaliana* Col-0 line (stock number: CS60000) {wild-type strain} or the stomagen-Venus-expressing line obtained in Preparation Example 9 was dissolved in 5 mL of a solution {composition: 50 mM tris hydrochloric acid buffer (pH 7.5), 50 mM sodium chloride, and 1% by volume CAPS solution}. Next, the resulting sample was mixed with 200 µL of anti-GFP beads in a protein isolation kit {manufactured by Milteny Biotech, trade name: µMACS GFP-tag protein isolation kit}. The resulting mixture was allowed to stand at 4° C. After the beads were adsorbed to a magnetic column, the proteins adhered to the beads were eluted with a buffer solution included in the protein isolation kit.

Western blot analysis was performed by using the resulting fraction and the anti-stomagen antibody obtained in Preparation Example 2 according to the method described in Literature 24. The anti-stomagen antibody was used in a concentration of 1/1000. As a secondary antibody, a horseradish peroxidase-conjugated anti-rabbit IgG-goat antibody {manufactured by GE Healthcare, trade name: NA934} was used in a concentration of 1/5000. The result of performing western blot analysis with the use of an anti-stomagen antibody for a fraction obtained from a stomagen-Venus-expressing line in Example 2 is shown in FIG. 17.

Figure 17:
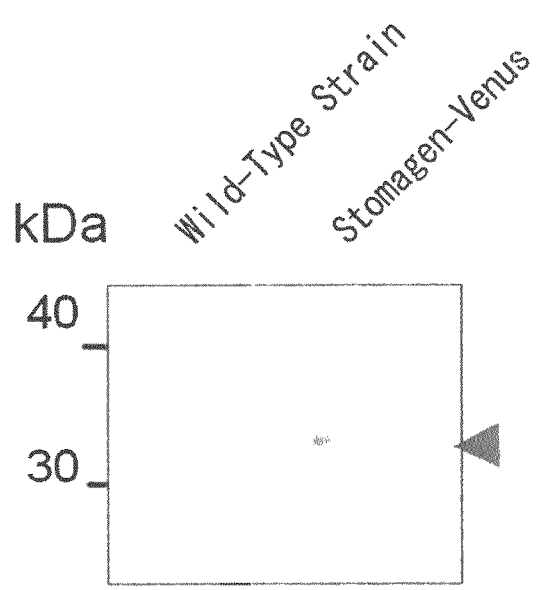
FIG. 17 is a photograph substituted for drawing showing the result of performing western blot analysis using an anti-stomagen antibody for a fraction obtained from a stomagen-Venus-expressing line in Example 2.

From the result shown in FIG. 17, it can be seen that the fraction contains a polypeptide to which an anti-stomagen antibody binds since a single band was detected.

Figure 18:
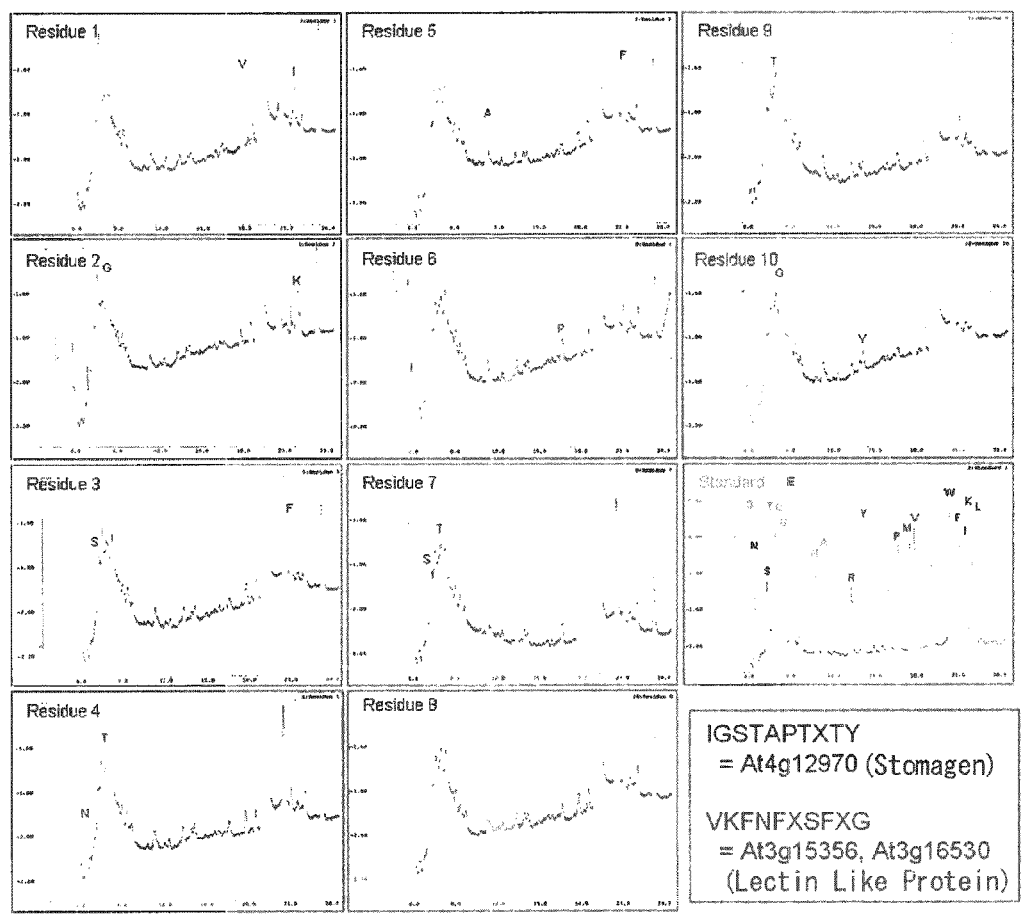
FIG. 18 shows graphs showing the result of analyzing the N-terminal amino acid sequence of stomagen-Venus in Example 2.

Next, the fraction was separated by SDS-PAGE. The resulting separated product was blotted on a PVDF membrane (Immobilon-P, manufactured by Millipore). Then, detection by CBB staining or an anti-stomagen antibody was performed. Moreover, the CBB-stained band corresponding to the band to which the anti-stomagen antibody binds was excised, and thereafter a polypeptide was extracted. The N-terminal amino acid sequence of the extracted polypeptide (stomagen) was determined by using an automatic peptide sequencer {manufactured by Life Technologies, trade name: Procise 492cLC}. The result of analyzing the N-terminal amino acid sequence of stomagen-Venus in Example 2 is shown in FIG. 18.

The stomagen gene encodes a small protein comprising 102 amino acids, the protein having an amino acid sequence which is a putative signal peptide, at N terminus (see FIG. 1). From the result shown in FIG. 18, it can be seen that the N-terminal amino acid sequence of the polypeptide produced in the stomagen-Venus-expressing line is IGSTAPTXTY (where X is undeterminable) (SEQ ID NO: 42) (a part of the amino acid residues of SEQ ID NO: 1), which is identical to the sequence starting from isoleucine 58 in the amino acid sequence presumed from the stomagen gene.

Next, the polypeptide was identified by mass spectrometry according to the method described in Literature 27. First, the fraction was separated by SDS-PAGE, followed by silver staining. The respective bands were excised separately and then subjected to the in-gel digestions with trypsin or lysyl endopeptidase {manufactured by Promega} in a buffer solution {composition: 50 mM ammonium bicarbonate (pH 8.0), and 2% by volume acetonitrile} for a day. The digestion product was subjected to matrix-assisted laser desorption/ionization time-of-flight mass spectrometry (MALDI-TOF/MS) with a mass spectrometer {manufactured by Bruker Daltonics, trade name: ultraflex TOF/TOF}. The result of analyzing the N-terminal amino acid sequence of stomagen-Venus by mass spectrometry using lysyl endopeptidase in Example 2 is shown in FIG. 19 (*a*) and the result of analyzing the N-terminal amino acid sequence of stomagen-Venus by mass spectrometry using trypsin in Example 2 is shown in FIG. 19 (*b*).

From the results shown in FIG. 19, it can be seen that the amino acid sequence of trypsin degradation product is IGSTAPTCTYNECR (residues 58-71 of SEQ ID NO: 1), and the amino acid sequence of lysyl endopeptidase degradation product is IGSTAPTCTYNECRGCRYK (residues 58-76 of SEQ ID NO: 1). This result is consistent with the analysis result of the peptide sequencer. From these results, it can be seen that stomagen is cleaved to produce a 45-amino-acid peptide having six cysteine residues in a plant.

Orthologues of stomagen in each of *Oryza sativa* (Os01g0914400), *Vitis vinifera* (AM444732), *Populus trichocarpa* (Pt02g2557) and *Selaginella moellendorffii* (Sm084711) were examined by Clustal W. The result of multiple alignment of orthologues of stomagen in each of *Oryza sativa* (Os01g0914400), *Vitis vinifera* (AM444732), *Populus trichocarpa* (Pt02g2557), and *Selaginella moellendorffii* (Sm084711) conducted by Clustal W in Example 2 is shown in FIG. 20.

In a transformant overexpressing stomagen with a signal peptide (SP-stomagen-expressing line), stomatal density increased (observed in ten independent T2 plants, see FIG. 14). This indicates that the 45-amino-acid peptide is sufficient to induce stomatal differentiation. In addition, from the result shown in FIG. 20, it can be seen that a gene encoding stomagen-like peptide was found in various plants, and interestingly, also observed in *Selaginella moellendorffii*, a primitive vascular plant. It is considered from these results that stomagen is widely distributed in a vascular plant. Therefore, it is considered that the stomagen acts in the plants including vascular plants.

Example 3

In order to obtain pure stomagen, a stomagen gene (STOMAGEN) was introduced into a tobacco-cultured BY-2 cell.

A region of HuIFNγ gene in a tomato mosaic virus vector pBICER8-ToMV-C0.3-HuIFNγ-SRz22 was replaced by a DNA encoding stomagen, to obtain a vector for expressing stomagen (hereinafter, referred to as a "stomagen-expressing vector").

A stomagen-expressing BY-2 cell was obtained by introducing the resulting stomagen-expressing vector into a BY-2 cell having an estrogen-inducible transcription factor XVE. Next, induction by β-estrogen was performed according to the method described in Literature 20. Thereafter, the culture was subjected to ultracentrifugation at 100000×g for 1 hour, to give a supernatant (culture supernatant). In addition, after homogenization of the cells, the resulting homogenate was subjected to centrifugation at 800 rpm for 3 minutes, to give a supernatant (cell extract).

Figure 21:
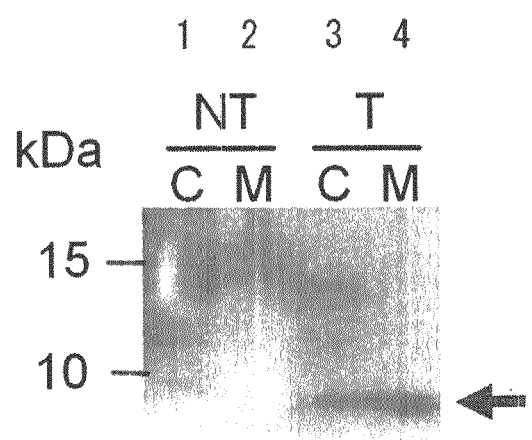
FIG. 21 is a photograph substituted for drawing showing the result of performing western blot analysis using an anti-stomagen antibody for a culture of stomagen-expressing BY-2 cells in Example 3.

Western blot analysis was performed by using the culture supernatant or the cell extract and the anti-stomagen antibody obtained in Preparation Example 2 according to the method described in Literature 24. The anti-stomagen antibody was used in a concentration of 1/1000. As a secondary antibody, a horseradish peroxidase-conjugated anti-rabbit IgG-goat antibody {manufactured by GE Healthcare, trade name: NA934} was used in a concentration of 1/5000. In addition, as a control, a supernatant of BY-2 cell culture was used. The result of performing western blot analysis using the anti-stomagen antibody for the stomagen-expressing BY-2 cell culture in Test Example 3 is shown in FIG. 21. In the figure, "C" represents the cell extract and "M" represents the culture supernatant. In addition, in the figure, "T" represents the stomagen-expressing BY-2 cell and "NT" represents the BY-2 cell.

Figure 22:
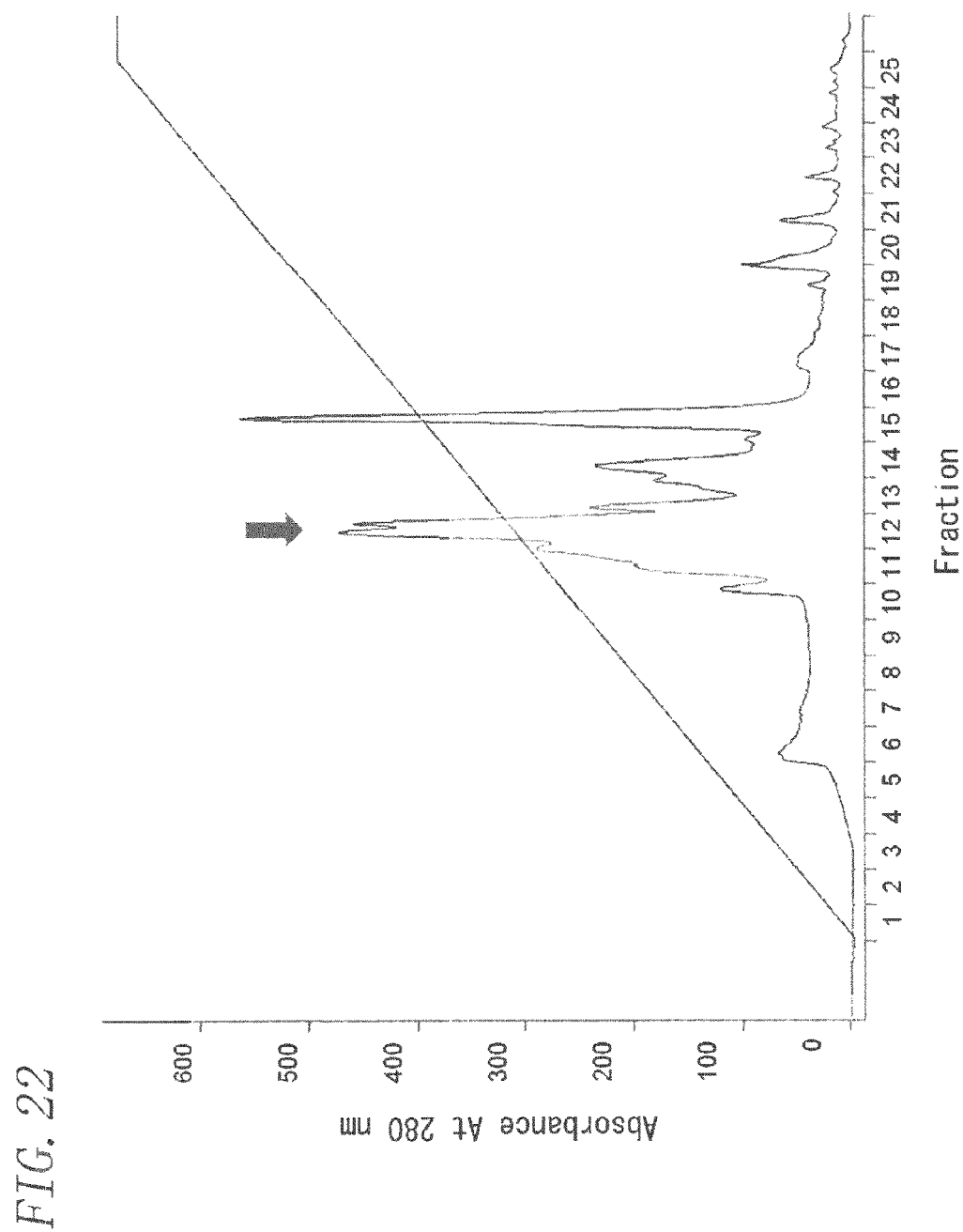
FIG. 22 is a chromatogram upon performing purification of stomagen using a reversed-phase HPLC column in Example 3.

From the result shown in FIG. 21, it can be seen that the culture supernatant contains a polypeptide to which the anti-stomagen antibody binds, i.e., stomagen. Therefore, stomagen was purified by carrying out the following operation with the use of the culture supernatant. The culture supernatant was filtered through a 0.22-μm filter {manufactured by Millex}. The resulting filtrate was filled into a reverse-phase HPLC column {manufactured by Pharmacia, trade name: mRPC C2/C18 SP4/6}. Thereafter, the column was washed with a washing solution {composition: 5% by volume methanol, 0.5% by volume trifluoroacetic acid (hereinafter, referred to as "TFA"), and balance water}. Next, elution was conducted by flowing into the column with a linear gradient using a developing solvent A {composition: 90% by volume methanol, 0.5% by volume TFA, and balance water} and a washing solution so as to have a methanol concentration gradient of 5% by volume to 90% by volume. A one milliliter of the eluate was fractionated. In each fraction, the solvent was evaporated to concentrate up to about 100 μL. A chromatogram upon performing purification of stomagen using the reversed-phase HPLC column in Example 3 is shown in FIG. 22. In addition, an electropherogram showing the result of analyzing each fraction in chromatography using the reversed-phase HPLC column by SDS-PAGE in Example 3 is shown in FIG. 23.

Figure 23:
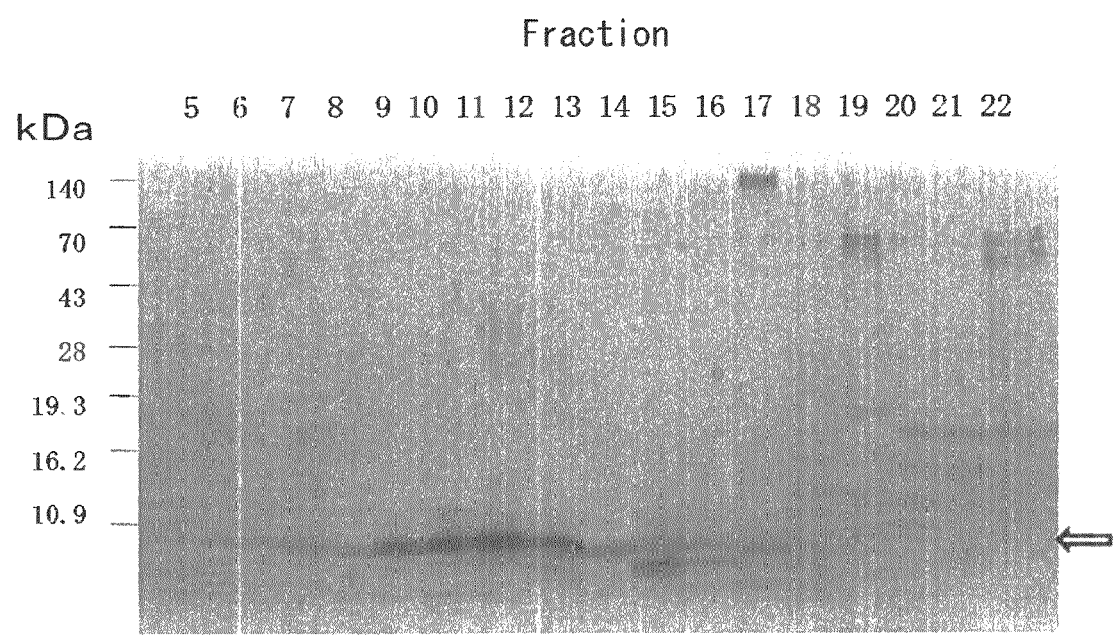
FIG. 23 is a photograph substituted for drawing of an electropherogram showing the result of analyzing each fraction in chromatography using a reversed-phase HPLC column by SDS-PAGE in Example 3.
Figure 24:
FIG. 24 is a drawing showing the result of analyzing the N-terminal amino acid sequence of stomagen contained in 10th to 13th fractions by Edman degradation in Example 3.

From the results shown in FIG. 22 and FIG. 23, it can be seen that a single band with a size of about 5 kDa is observed in some fractions. Therefore, the N-terminal amino acid sequence of stomagen contained in 10th to 13th fractions was determined by Edman degradation. The result of analyzing the N-terminal amino acid sequence of stomagen contained in 10th to 13th fractions by Edman degradation in Example 3 is shown in FIG. 24. In addition, the electropherogram of purified recombinant stomagen in Example 3 is shown in FIG. 25.

Figure 25:
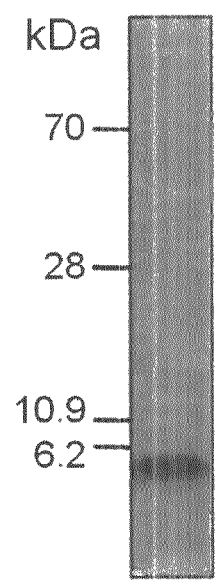
FIG. 25 is a photograph substituted for drawing of an electropherogram of a purified recombinant stomagen in Example 3.

From the results shown in FIG. 24 and FIG. 25, it can be seen that a recombinant stomagen having the same N-terminal amino acid sequence as the wild-type stomagen is obtained.

Example 4

Figure 26:
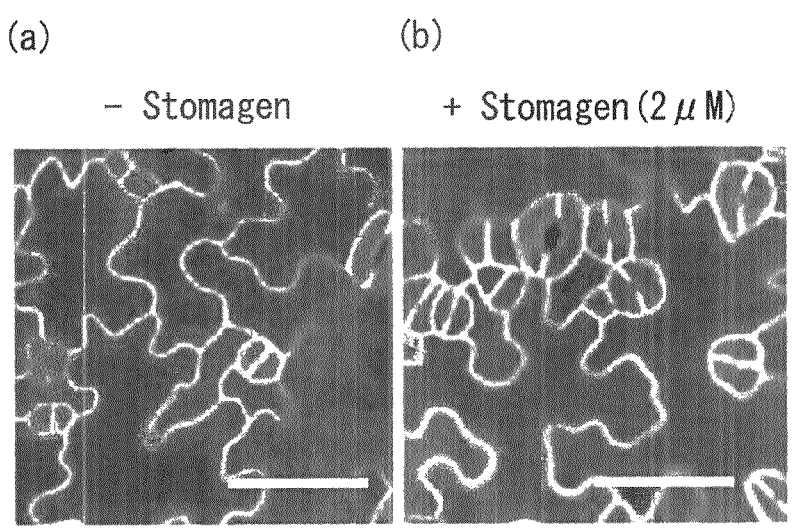
FIG. 26 (a) is a photograph substituted for drawing of a confocal microscopic image of abaxial epidermis of a cotyledon of an Lti6b-GFP-expressing line to which purified recombinant stomagen was not administered in Example 4, and (b) is a photograph substituted for drawing of a confocal microscopic image of abaxial epidermis of a cotyledon of an Lti6b-GFP-expressing line to which purified recombinant stomagen (2 μM) was administered in Example 4.

Seeds of *Arabidopsis thaliana* {Lti6b-GFP line} were maintained in a B5 sterilized medium {manufactured by NIHON PHARMACEUTICAL CO., LTD, catalogue number: 399-00621} for germination. To the Lti6b-GFP line at 2 days after germination was administered the purified recombinant stomagen obtained in Example 2, so as to have a concentration of 2 μM. Thereafter, the Lti6b-GFP line was grown for 3 days at 22° C. The abaxial epidermis of the cotyledons was observed under a confocal microscope. The same operation was carried out as described above, using as a control an Lti6b-GFP line to which stomagen was not administered. The abaxial epidermis of the cotyledons was observed. A confocal microscopic image of abaxial epidermis of the cotyledon of the Lti6b-GFP-expressing line to which the purified recombinant stomagen was not administered in Example 4 is shown in FIG. 26 (*a*) and a confocal microscopic image of abaxial epidermis of the cotyledon of the Lti6b-GFP-expressing line to which the purified recombinant stomagen (2 μM) was administered in Example 4 is shown in FIG. 26 (*b*). In the figures, a scale bar represents 50 μm.

From the results shown in FIG. 26, it can be seen that the number of stomata and the stomatal density increased in abaxial epidermis of the cotyledon of the Lti6b-GFP-expressing line to which the purified recombinant stomagen was administered {see FIG. 26 (*b*)}, as compared to abaxial epidermis of the cotyledon of the Lti6b-GFP-expressing line to which the purified recombinant stomagen was not administered {see FIG. 26 (*a*)}. Incidentally, when the effect of ethylene during the liquid culture was evaluated by using silver thiosulfate, the effect of stomagen was confirmed to have no relation to ethylene. Therefore, this result suggests that the number of stomata and/or stomatal density in a plant can be increased by administrating stomagen to the plant.

Example 5

The polypeptide (45 amino acids) comprising 58th to 102nd amino acid residues of the amino acid sequence shown in SEQ ID NO: 1 was chemically synthesized. A polypeptide solution containing the resulting polypeptide (0.5 mg/mL) was dissolved in a solution {20 mM tris hydrochloric acid buffer (pH 8.8), and 50 mM sodium chloride}. Thereafter, the resulting sample was dialyzed with a dialysis membrane {manufactured by Spectrum Laboratories, trade name: Spectra/Por3MWCO, 3500} at 4° C. for 1 day against an aqueous solution for dialysis {composition: 0.5 mM glutathione (both of oxidized and reduced forms, manufactured by Wako Pure Chemical Industries, Ltd., catalogue number: 077-03334 for oxidized form, and catalogue number: 194679 for reduced form) and 200 mM L-arginine (pH 8.0)}. The resulting dialyzed product was dialyzed three times against a solution {20 mM tris hydrochloric acid buffer (pH 8.8), and 50 mM sodium chloride} for 1.5 days, to remove glutathione. At this stage, a synthetic stomagen was obtained. The purity and the like of the resulting synthetic stomagen were confirmed by SDS-PAGE.

Example 6

The seeds of *Arabidopsis thaliana* {Lti6b-GFP line} were maintained in a B5 sterilized medium for germination. To the Lti6b-GFP line at 2 days after germination was administered the synthetic stomagen obtained in Example 5, so as to have a concentration of 300 nM. Thereafter, the Lti6b-GFP line was grown for 3 days at 22° C. Next, the cotyledon was collected. The surface was observed under a confocal microscope {manufactured by Zeiss, trade name: LSM510 META microscope}, to determine the number of stomata in a square area of 0.22 mm$^2$. Then, stomatal density was calculated. Here, statistical analysis was conducted by using R statistical analysis software. In addition, stomatal density was calculated by carrying out the same operation as described above with the use of an Lti6b-GFP line to which stomagen was not administered as a control. The result of examining the relationship between the amount of synthesized stomagen and stomatal density in Example 6 is shown in FIG. 27.

Figure 27:
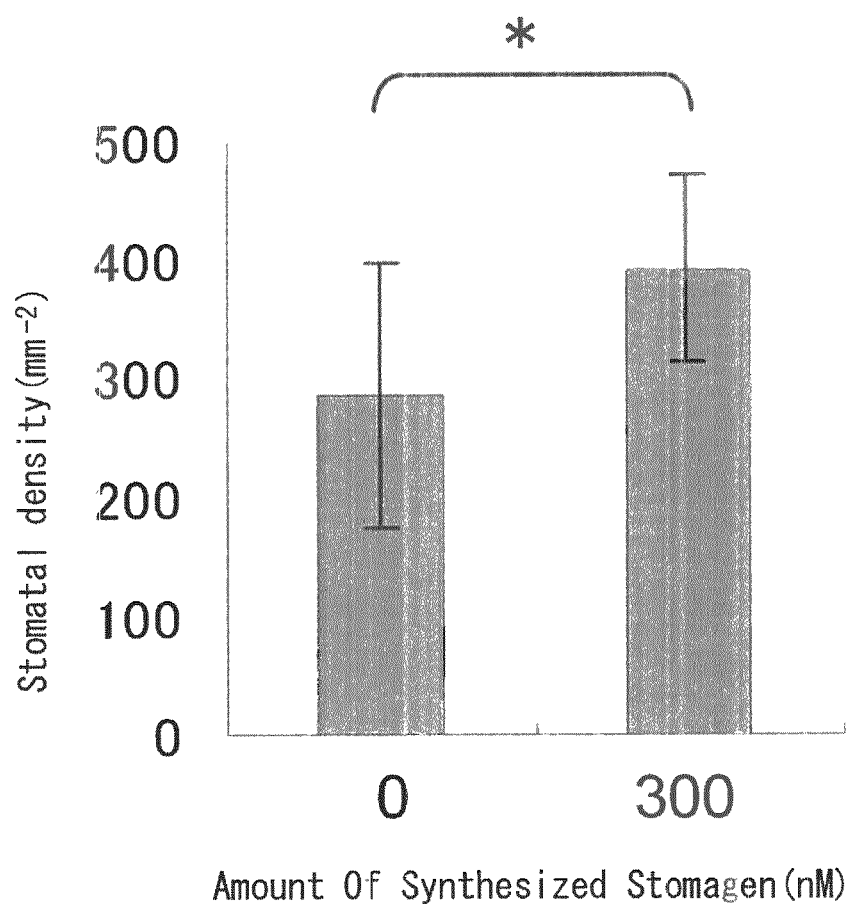
FIG. 27 is a graph showing the result of examining the relationship between the amount of synthesized stomagen and stomatal density in Example 6.

From the result shown in FIG. 27, it can be seen that stomatal density increases in abaxial epidermis of cotyledons of the Lti6b-GFP expressing line to which synthetic stomagen was administered, as compared to abaxial epidermis of cotyledons of the Lti6b-GFP-expressing line to which synthetic stomagen was not administered. Incidentally, when the effect of ethylene during the liquid culture was evaluated by using silver thiosulfate, the effect of stomagen was confirmed to have no relation to ethylene. Therefore, this result suggests that the stomatal density in a plant can be increased by administrating synthetic stomagen to the plant. From the results described above, it can be seen that both the recombinant stomagen expressed in the BY-2 cells (Example 2) and the chemically synthesized stomagen (Example 4) can concentration-dependently increase stomatal density. From the results, it was demonstrated that stomagen is a stomata-inducing factor.

Preparation Example 12

A plant having SPCH gene to which T-DNA was inserted was selected by germinating the seeds ordered from *Arabidopsis* stock center (ABRC, U.S.) (strain number: SAIL__36_B6), extracting a DNA of the germ, and performing PCR with the use of the primer spch SAIL__36_B6 LP and primer SAIL__36_B6 RP shown in Table 1. At this stage, *Arabidopsis thaliana* mutant with a deficiency of SPCH gene (spch mutant) was obtained.

Preparation Example 13

A stomagen-overexpressing spch mutant was obtained by carrying out the same operation as in Preparation Example 4, except that the spch mutant obtained in Preparation Example 12 was used in place of the *Arabidopsis thaliana* Col-0 line in Preparation Example 4.

Test Example 9

It has been considered that the stomatal lineage is triggered by a bHLH type transcriptional factor also called SPEECHLESS(SPCH) (see Literature 13 and Literature 14). Therefore, the influence of stomagen was examined by using the spch mutant obtained in Preparation Example 12 and the stomagen-overexpressing spch mutant obtained in Preparation Example 13.

The seeds of the spch mutant or the seeds of *Arabidopsis thaliana* Col-0 line (stock number: CS60000) {wild-type strain} were maintained in a B5 sterilized medium for germination. To the spch mutant or the wild-type strain at 2 days after germination was administered the purified recombinant stomagen obtained in Example 2, so as to have a concentration of 2 μM. Thereafter, the spch mutant or the wild-type strain was grown at 22° C. for 3 days. The abaxial epidermis of the cotyledon was observed under a confocal microscope {manufactured by Zeiss, trade name: LSM510 META microscope}. The abaxial epidermis of the cotyledons was observed by carrying out the same operation was carried out as described above with the use of a spch mutant line to which stomagen was not administered as a control. A confocal microscopic image of abaxial epidermis of the cotyledon of the spch mutant to which purified recombinant stomagen was not administered in Test Example 9 is shown in FIG. 28 (*a*), a confocal microscopic image of abaxial epidermis of the cotyledon of the spch mutant to which purified recombinant stomagen (2 μM) was administered in Test Example 9 is shown in FIG. 28 (*b*), and a confocal microscopic image of abaxial epidermis of the cotyledon of the wild-type strain to which purified recombinant stomagen (2 μM) was administered in Test Example 9 is shown in FIG. 28 (*c*).

In addition, the cotyledons at 23 days after germination of each of the spch mutant, the stomagen-overexpressing spch mutant or the stomagen-overexpressing line obtained in Preparation Example 4 (stomagen-overexpressing line 10) were collected. Subsequently, the cotyledons were fixed and made transparent, and then stomata were stained, by carrying out the same operation as in Test Example 1. Thereafter, the abaxial epidermis of the first leaves was observed under a differential interference microscope {manufactured by Zeiss, trade name: Axioskop plus microscope}. The differential interference image showing the result of observing abaxial epidermis of the cotyledon of the spch mutant in Test Example 9 is shown in FIG. 28 (*d*), the differential interference image showing the result of observing abaxial epidermis of the cotyledon of the stomagen-overexpressing spch mutant in Test Example 9 is shown in FIG. 28 (*e*), and the differential interference image showing the result of observing abaxial epidermis of the cotyledon of the stomagen-overexpressing line in Test Example 9 is shown in FIG. 28 (*f*). In FIG. 28, a scale bar represents 50 μm.

Figure 28:
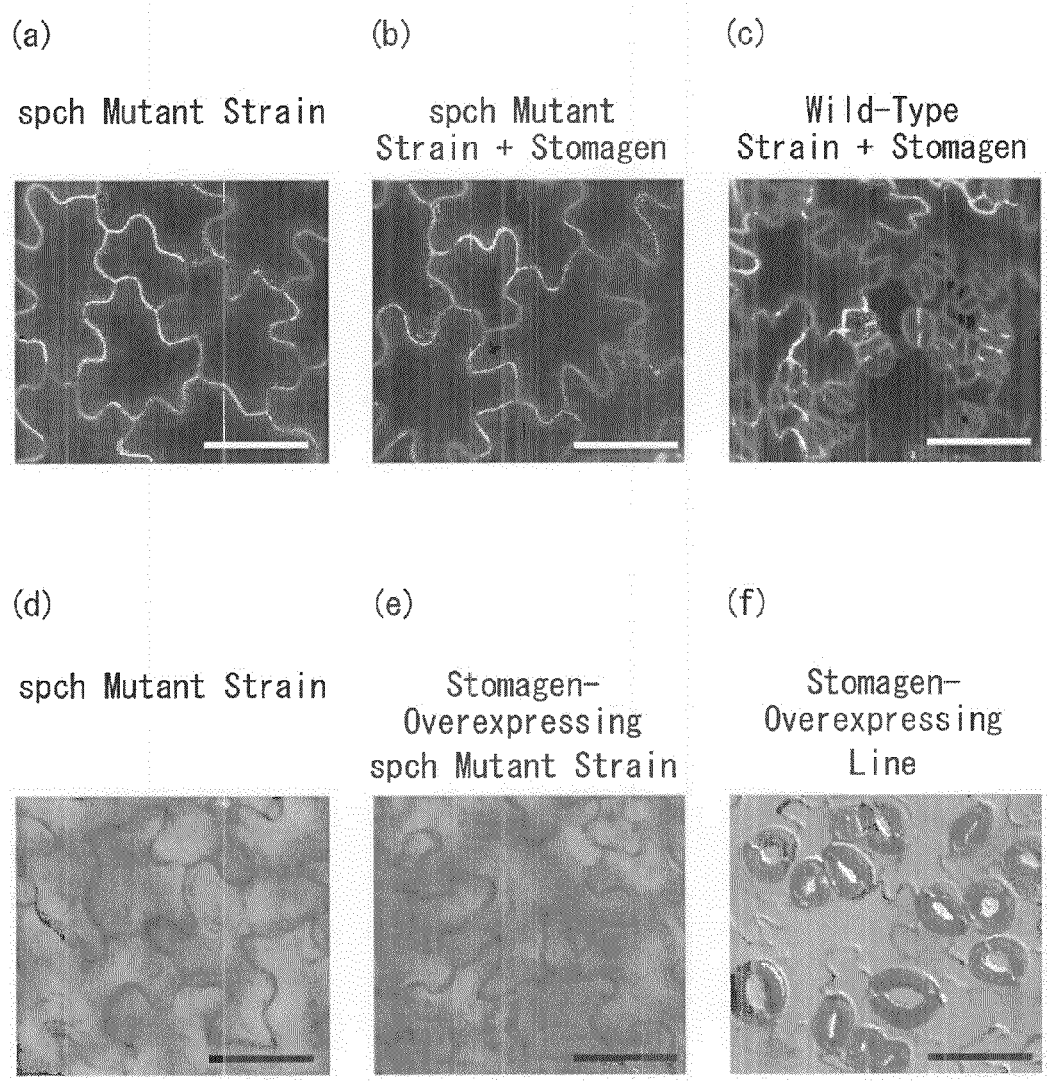
FIG. 28 (a) is a photograph substituted for drawing of a confocal microscopic image of abaxial epidermis of a cotyledon of a spch mutant to which purified recombinant stomagen was not administered in Test Example 9, (b) is a photograph substituted for drawing of a confocal microscopic image of abaxial epidermis of a cotyledon of a spch mutant to which purified recombinant stomagen (2 μM) was administered in Test Example 9, (c) is a photograph substituted for drawing of a confocal microscopic image of abaxial epidermis of a cotyledon of a wild-type strain to which purified recombinant stomagen (2 μM) was administered in Test Example 9, (d) is a photograph substituted for drawing of a differential interference image showing the result of observing abaxial epidermis of a cotyledon of a spch mutant in Test Example 9, (e) is a photograph substituted for drawing of a differential interference image showing the result of observing abaxial epidermis of a cotyledon of a stomagen-overexpressing spch mutant in Test Example 9, and (f) is a photograph substituted for drawing of a differential interference image showing the result of observing abaxial epidermis of a cotyledon of a stomagen-overexpressing line in Test Example 9.

From the results shown in FIG. 28, it can be seen that, in both the cases where stomagen is administered to the spch mutant and where stomagen is overexpressed in the spch mutant, stomata do not increase {see FIG. 28 (*b*) and FIG. 28 (*e*)}. Therefore, these results suggest that a stomagen gene increases stomata depending on SPCH gene-driven pathway.

Preparation Example 14

*Arabidopsis thaliana* mutant with a deficiency of TMM gene (tmm mutant) was obtained by carrying out the same operation as in Preparation Example 12, except that strain number: SALK_011958 was used in place of the seeds ordered from ABRC (strain number: SAIL_36_B6) and that the primer tmm SALK_011958-LP and primer SALK_011958-RP shown in Table 1 were used in place of the primer spch SAIL_36_B6 LP and primer SAIL_36_B6 RP shown in Table 1 in Preparation Example 12.

Preparation Example 15

A stomagen-overexpressing tmm mutant was obtained by carrying out the same operation as in Preparation Example 4, except that the tmm mutant obtained in Preparation Example 14 was used in place of the *Arabidopsis thaliana* Col-0 line in Preparation Example 4

Preparation Example 16

A stomagen-silenced tmm mutant was obtained by carrying out the same operation as in Preparation Example 5, except that the tmm mutant obtained in Preparation Example 14 was used in place of the *Arabidopsis thaliana* Col-0 line in Preparation Example 5.

Test Example 10

SPCH regulates the gene expressions of the receptor-like protein TMM and its putative ligand candidates EPF1 and EPF2 (Literatures 5, 13, and 14). TMM acts negatively in the leaf but positively in the stem in stomatal differentiation (Literature 16). On the other hand, EPF1 and EPF2 act negatively in both organs (Literatures 4 and 5).

Therefore, first, the interaction between stomagen and the receptor-like protein TMM was examined. The mature stems or first leaves of each of *Arabidopsis thaliana* Col-0 line (stock number: CS60000) {wild-type strain}, the stomagen-silenced line obtained in Preparation Example 5 (stomagen-silenced line 10), the stomagen-overexpressing line obtained in Preparation Example 4 (stomagen-overexpressing line 10), the tmm mutant obtained in Preparation Example 14, the stomagen-silenced tmm mutant obtained in Preparation Example 15, and the stomagen-overexpressing tmm mutant obtained in Preparation Example 16 were collected. Next, the surface of the stems or first leaves was observed under a differential interference microscope {manufactured by Zeiss, trade name: Axioskop plus microscope}, to determine the number of stomata in a square area of 0.22 mm². Then, stomatal density was calculated. Here, statistical analysis was conducted y b using R statistical analysis software. Kruskal-Wallis test was conducted. The result of examining the relationship between the types of plants and stomatal density in the stem in Test Example 10 is shown in FIG. 29 (*a*), and the relationship between the types of plants and the stomatal density in the leaf in Test Example 10 is shown in FIG. 29 (*b*). In the figures, lane 1 represents the wild-type strain, lane 2 represents the stomagen-silenced line, lane 3 represents the stomagen-overexpressing line, lane 4 represents the tmm mutant, lane 5 represents the stomagen-silenced tmm mutant, and lane 6 represents the stomagen-overexpressing tmm mutant.

In addition, by carrying out the same operation as in Test Example 1, the mature first leaves or stems of each of the wild-type strain, the stomagen-silenced line, the stomagen-overexpressing line, the tmm mutant, the stomagen-silenced tmm mutant, and the stomagen-overexpressing tmm mutant were fixed and made transparent, and then stomata were stained. Thereafter, the abaxial epidermis of the first leaves or stems were observed under a differential interference microscope {manufactured by Zeiss, trade name: Axioskop plus microscope}. Differential interference images showing the result of observing abaxial epidermis of first leaves of each of the wild-type strain, the stomagen-silenced line, the stomagen-overexpressing line, the tmm mutant, the stomagen-silenced tmm mutant and the stomagen-overexpressing tmm mutant in Test Example 10 are shown in FIG. 30 (A) and differential interference images showing the result of observing the stems of each of the wild-type strain, the stomagen-silenced line, the stomagen-overexpressing line, the tmm mutant, the stomagen-silenced tmm mutant and the stomagen-overexpressing tmm mutant in Test Example 10 are shown in FIG. 30 (B). In the figures, (*a*) represents the wild-type strain, (*b*) is shown in the stomagen-silenced line, (*c*) is shown in the stomagen-overexpressing line, (*d*) is shown in the tmm mutant, (*e*) is shown in the stomagen-silenced tmm mutant and (*f*) is shown in the stomagen-overexpressing tmm mutant. In the figures, a scale bar represents 100 μm.

From the results shown in FIG. 29 and FIG. 30, it can be seen that, surprisingly, even if overexpression of a stomagen gene is performed so as to have 44.8±16.7-fold expression level of a stomagen gene in a tmm mutant (10 independent lines of T2 plants) of the expression level in the wild-type strain, the number of stomata cannot be increased in either the leaf or the stem. It can be seen that, even if performing silencing the expression of a stomagen gene in the tmm mutant (10 independent lines of T2 plants), no effect is found (observed in 10 independent lines of T2 plants, see FIG. 29 and FIG. 30). These results indicate that stomagen requires TMM for positively regulating stomatal development. EPF1 and EPF2 have been thought to negatively regulate stomatal differentiation by binding to TMM as ligands. The results shown in FIG. 29 and FIG. 30 suggest that stomagen possibly competes with EPF1 or EPF2 for binding to TMM.

Preparation Example 17

*Arabidopsis thaliana* mutant with a deficiency of EPF1 gene (epf1 mutant) was obtained by carrying out the same operation as in Preparation Example 12, except that strain number: SALK__137549 was used in place of the seeds ordered from ABRC (strain number: SAIL__36_B6) and that the primer epf1SALK__137549-LP and primer SALK__137549-RP shown in Table 1 were used in place of the primer spch SAIL__36_B6 LP and primer SAIL__36_B6 RP shown in Table 1.

Preparation Example 18

A stomagen-silenced epf1 mutant was obtained by carrying out the same operation as in Preparation Example 5, except that the epf1 mutant obtained in Preparation Example 17 was used in place of the *Arabidopsis thaliana* Col-0 line in Preparation Example 5.

Preparation Example 19

*Arabidopsis thaliana* mutant with a deficiency of EPF2 gene (epf2 mutant) was obtained by carrying out the same operation as in Preparation Example 12, except that strain number: SALK__047918 was used in place of the seeds ordered from ABRC (strain number: SAIL__36_B6) and that the primer epf2SALK__047918-LP and primer SALK__047918-RP shown in Table 1 were used in place of the primer spch SAIL__36_B6 LP and primer SAIL__36_B6 RP shown in Table 1 in Preparation Example 12.

Preparation Example 20

A stomagen-silenced epf2 mutant was obtained by carrying out the same operation as in Preparation Example 5, except that the epf2 mutant obtained in Preparation Example 20 was in place of the *Arabidopsis thaliana* Col-0 line in Preparation Example 5.

Preparation Example 21

The epf1 mutant obtained in Preparation Example 17 and the epf2 mutant obtained in Preparation Example 19 were crossbred, and then plants of F2 generation progeny were germinated. Thereafter, a DNA was extracted. Plant in which T-DNA was inserted into both EPF1 gene and EPF2 gene was selected by using the primer epf1SALK__137549-LP and primer SALK__137549-RP and the primer epf2SALK__047918-LP and primer SALK__047918-RP shown in Table 1. At this stage, *Arabidopsis thaliana* double mutant with a deficiency of EPF1 gene and EPF2 gene (epf1-epf2 double mutant) was obtained.

Preparation Example 22

A stomagen-silenced epf1-epf2 double mutant was obtained by carrying out the same operation as in Preparation Example 5, except that the epf1-epf2 double mutant obtained in Preparation Example 21 used in place of the *Arabidopsis thaliana* Col-0 line in Preparation Example 5.

Test Example 11

In order to examine the possibility of "competitive binding" of stomagen with EPF1 or EPF2, the expression of a stomagen gene on the epf1 mutant or epf2 mutant was silenced, to analyze two indices: "stomatal density" and "non-stomatal cell density (density of cells other than stomata)".

Figure 31:
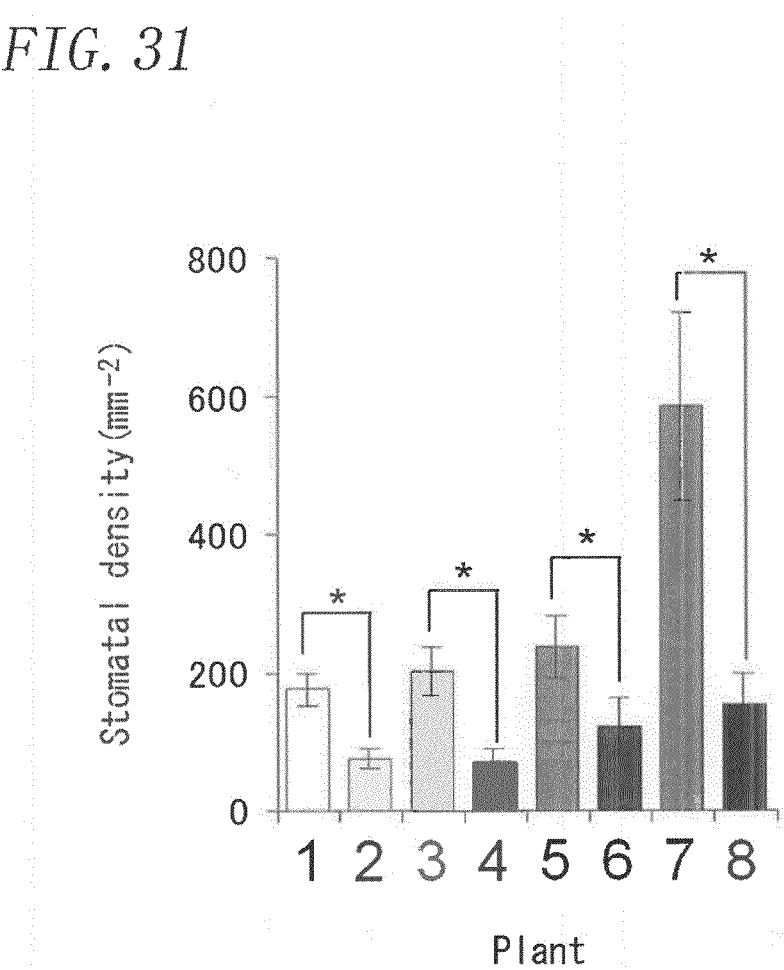
FIG. 31 is a graph showing the result of examining the relationship between the types of plants and stomatal density in Test Example 11.
Figure 32:
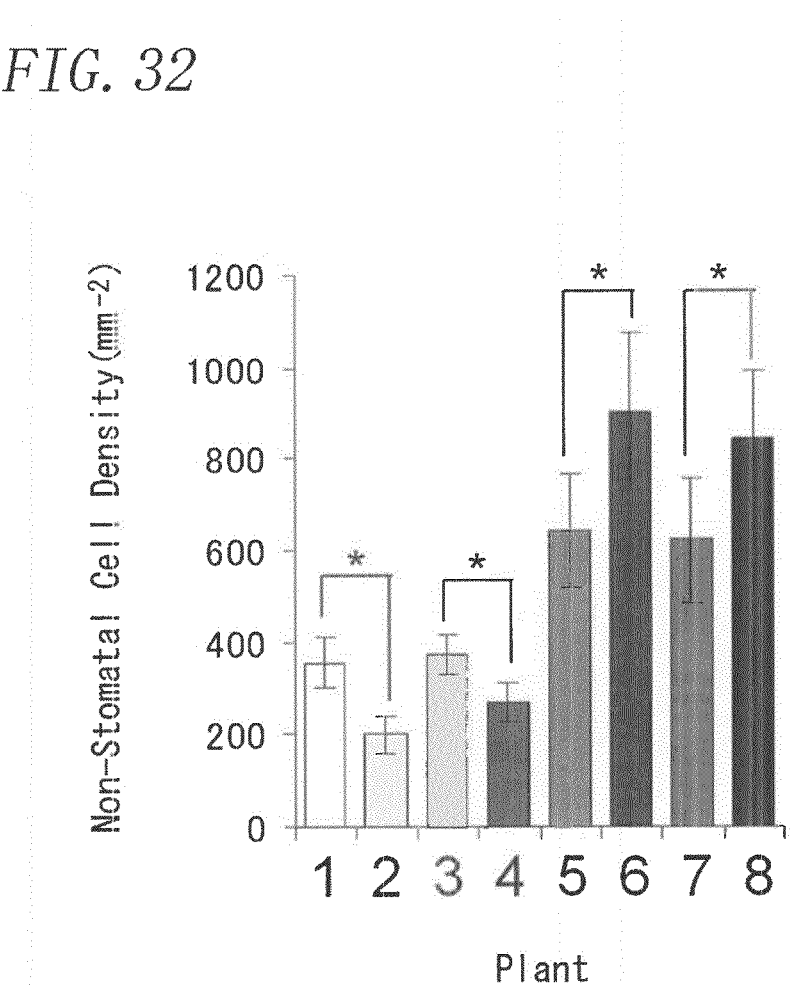
FIG. 32 is a graph showing the result of examining the relationship between the types of plants and non-stomatal cell density in Test Example 11.

The mature first leaves of each of *Arabidopsis thaliana* Col-0 line (stock number: CS60000) {wild-type strain}, the stomagen-silenced line obtained in Preparation Example 5 (stomagen-silenced line 10), the epf1 mutant obtained in Preparation Example 17, the stomagen-silenced epf1 mutant obtained in Preparation Example 18, the epf2 mutant obtained in Preparation Example 19, the stomagen-silenced epf2 mutant obtained in Preparation Example 20, the epf1-epf2 double mutant obtained in Preparation Example 21 and the stomagen-silenced epf1-epf2 double mutant obtained in Preparation Example 22 were collected. Next, the surface of the first leaves was observed under a differential interference microscope {manufactured by Zeiss, trade name: Axioskop plus microscope}, to determine the number of stomata in a square area of 0.22 mm$^2$. Then, stomatal density and non-stomatal cell density were calculated. Here, statistical analysis was conducted by using R statistical analysis software. In addition, two-tailed student's t-test was conducted. The result of examining the relationship between the types of plants and stomatal density in Test Example 11 is shown in FIG. 31. In addition, the result of examining the relationship between the types of plants and non-stomatal cell density in Test Example 11 is shown in FIG. 32. In the figure, lane 1 represents the wild-type strain, lane 2 represents the stomagen-silenced line, lane 3 represents the epf1 mutant, lane 4 represents the stomagen-silenced epf1 mutant, lane 5 represents the epf2 mutant, lane 6 represents the stomagen-silenced epf2 mutant, lane 7 represents the epf1-epf2 double mutant and lane 8 represents the stomagen-silenced epf1-epf2 double mutant. An asterisk represents that the p-value is less than 0.01.

Figure 33:
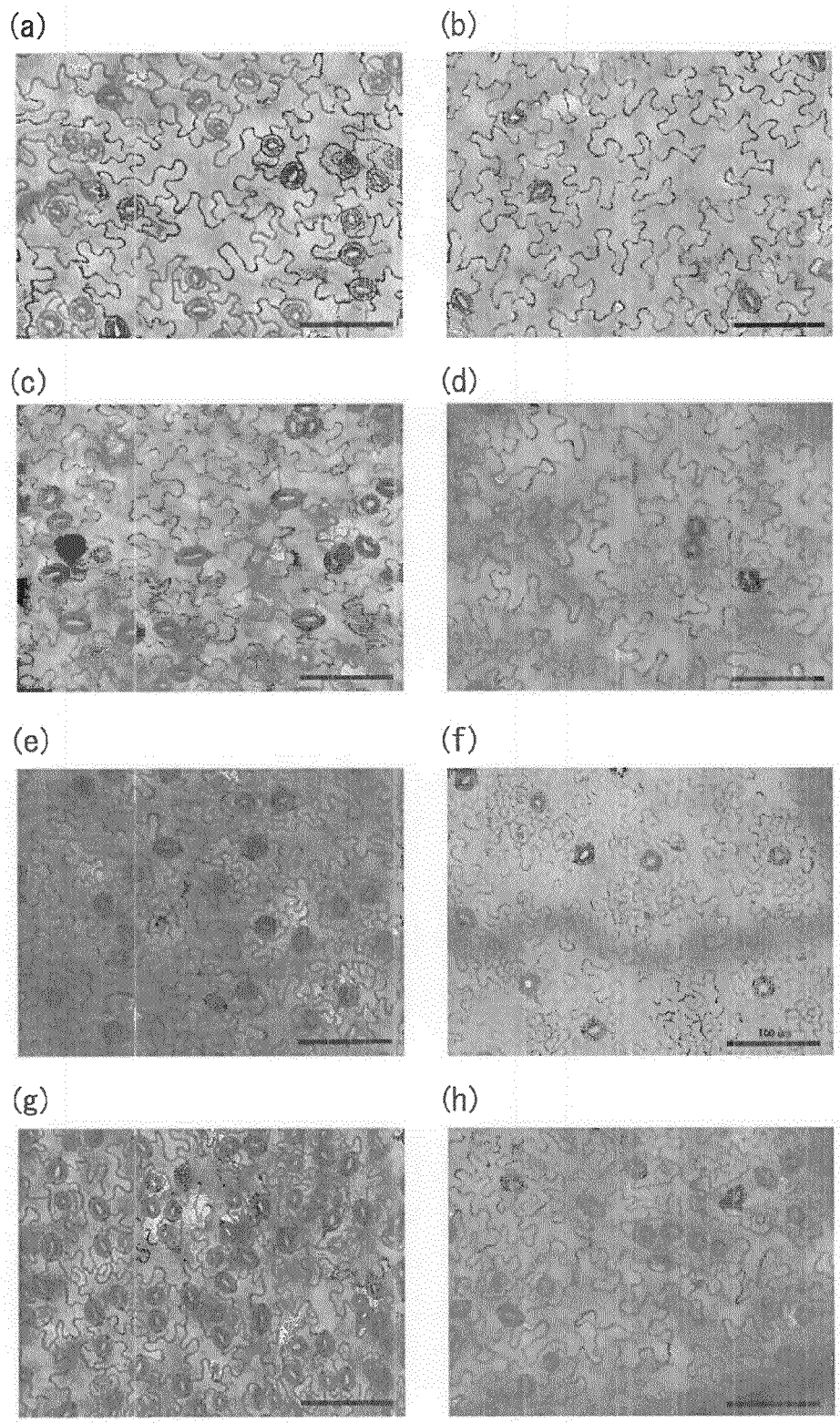
FIG. 33 shows photographs substituted for drawings of differential interference images showing the result of observing abaxial epidermis of mature first leaves of plants in Test Example 11.

In addition, the mature first leaves of each of the wild-type strain, the stomagen-silenced line, the epf1 mutant, the stomagen-silenced epf1 mutant, the epf2 mutant, the stomagen-silenced epf2 mutant, the epf1-epf2 double mutant, and the stomagen-silenced epf1-epf2 double mutant were collected. Then, the first leaves were fixed and made transparent, and then stomata were stained by carrying out the same operation as in Test Example 1. Thereafter, the stems were observed under a differential interference microscope {manufactured by Zeiss, trade name: Axioskop plus microscope}. Differential interference images showing the result of observing abaxial epidermis of first leaves of plants in Test Example 11 are shown in FIG. 33. In the figures, (*a*) shows a photograph substituted for drawing of a differential interference image showing the result of observing abaxial epidermis of the first leaf of the wild-type strain in Test Example 11, (*b*) shows a photograph substituted for drawing of a differential interference image showing the result of observing abaxial epidermis of the first leaf of the stomagen-silenced line in Test Example 11, (*c*) shows a photograph substituted for drawing of a differential interference image showing the result of observing abaxial epidermis of the first leaf of the epf1 mutant in Test Example 11, (*d*) shows a photograph substituted for drawing of a differential interference image showing the result of observing abaxial epidermis of the first leaf of the stomagen-silenced epf1 mutant in Test Example 11, (*e*) shows a photograph substituted for drawing of a differential interference image showing the result of observing abaxial epidermis of the first leaf of the epf2 mutant in Test Example 11, (*f*) shows a photograph substituted for drawing of a differential interference image showing the result of observing abaxial epidermis of the first leaf of the stomagen-silenced epf2 mutant in Test Example 11, (*g*) shows a photograph substituted for drawing of a differential interference image showing the result of observing abaxial epidermis of the first leaf of the epf1-epf2 double mutant in Test Example 11, and (h) shows a photograph substituted for drawing of a differential interference image showing the result of observing abaxial epidermis of the first leaf of the stomagen-silenced epf1-epf2 double mutant in Test Example 11. In the figures, a scale bar represents 100 µm.

From the results shown in FIG. 31 and FIG. 33, it can be seen that stomatal density of each of the epf1 mutant and epf2 mutant is higher than stomatal density of the wild-type strain, but is reduced when the stomagen gene expression is silenced in each of the epf1 mutant and epf2 mutant. These results suggest that stomagen regulates the stomatal density independently from EPF1 and EPF2.

On the other hand, a different result was obtained when "non-stomatal cell density" was examined (see FIG. 32). EPF2 is a negative regulator of the production of stomatal lineage cells. From the results shown in FIG. 32, it can be seen that non-stomatal cell density of the epf2 mutant is higher than non-stomatal cell density of the wild-type strain. In addition, it can be seen that, when the stomagen gene expression is silenced in the wild-type strain, non-stomatal cell density is reduced (observed in 14 independent lines of T2 plants). On the other hand, when the stomagen gene expression was silenced in the epf2 mutant, non-stomatal cell density was not reduced (observed in 11 independent lines of T2 plants). From these results, it is considered that stomagen regulates the production of stomatal lineage cell in an EPF2-dependent manner. From the above, it seems that STOMAGEN has two functions: it regulates the production of stomatal lineage cells EPF2-dependently, and the differentiation of stomatal lineage cells to stomata independent of EPF1 and EPF2.

From the above results, it is considered that three signaling factors, i.e., stomagen, EPF1 and EPF2, regulate stomatal differentiation through the common receptor TMM. In addition to these signaling factors, SDD1 gene is known to act in the upstream of TMM gene (Literature 9). SDD1 has been thought to negatively regulate stomatal differentiation by cleaving a precursor of the negative regulator (Literatures 9 and 18). However, SDD1 is shown to be genetically independent of EPF1 and EPF2 (Literatures 4 to 6). Alternatively, there is also a hypothesis that SDD1 exerts its negative effect on stomatal differentiation by degrading stomagen, a positive regulator.

In addition, these results suggest that stomatal differentiation is regulated by a signal having two opposing characteristics: stomagen which is a stimulatory signal, and EPF1 and EPF2 which are inhibitory signals. Such a bi-directional signaling regulatory system would be important for regulating stomatal density more precisely. It was also shown that mesophyll cell-derived stomagen regulates the differentiation of stomatal lineage cells into stomata in the epidermal cells. This inter-tissue interaction would provide a conceptual advancement of stomatal differentiation. More specifically, a new idea such that "stomatal density is optimized by photosynthetic tissues (mesophyll) for efficient uptake of carbon dioxide" is provided. In addition, stomagen is also important in applications. It is suggested that the number of stomata and/or stomatal density can be increased by genetically engineering stomagen or directly administering stomagen to a plant including a developing crop, a tree and the like, thereby increasing the amount of carbon dioxide absorption.

Test Example 12

The stomagen-silenced line obtained in Preparation Example 5 (stomagen-silenced line 10), *Arabidopsis thaliana* Col-0 line (stock number: CS60000) {wild-type strain} or the stomagen-overexpressing line obtained in Preparation Example 4 (stomagen-overexpressing line 10) was grown under short-day conditions for 9 weeks.

Figure 34:
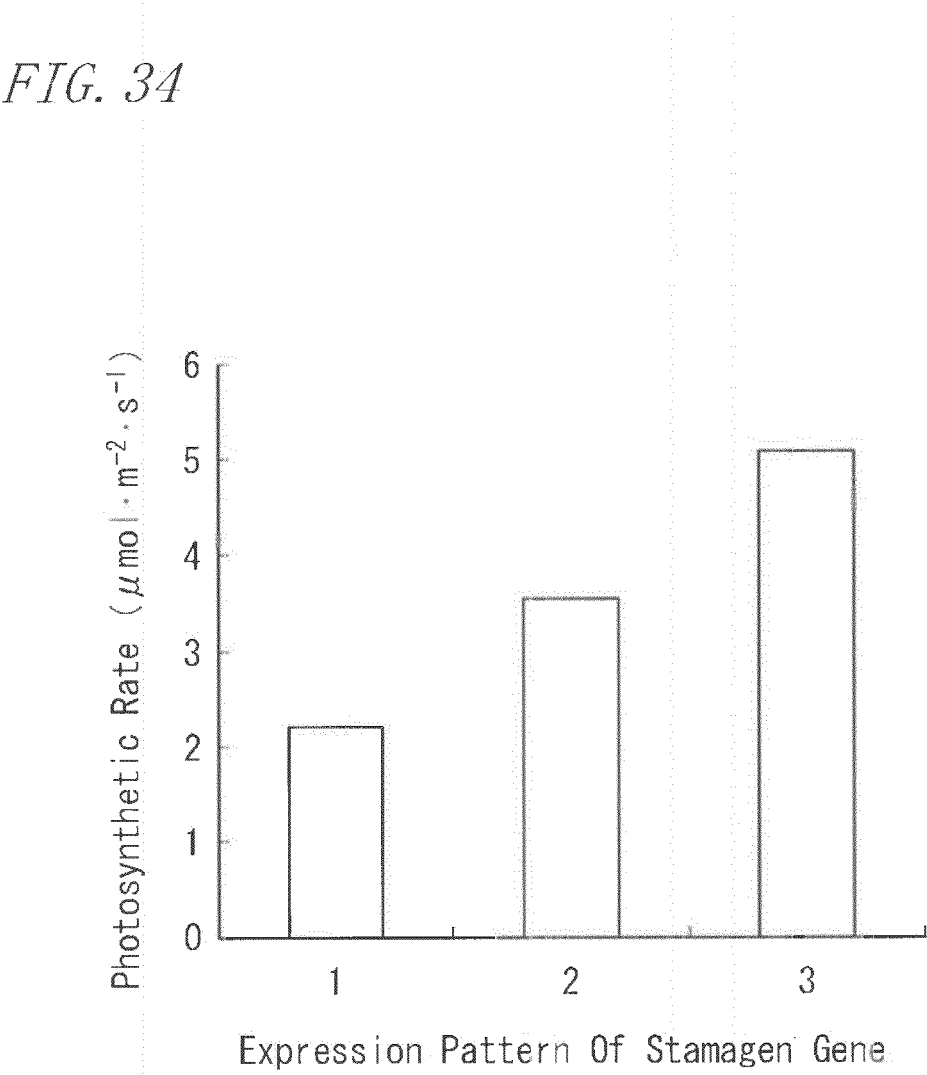
FIG. 34 is a graph showing the result of examining the relationship between an expression pattern of a stomagen gene and a photosynthetic rate in Test Example 12.
Figure 35:
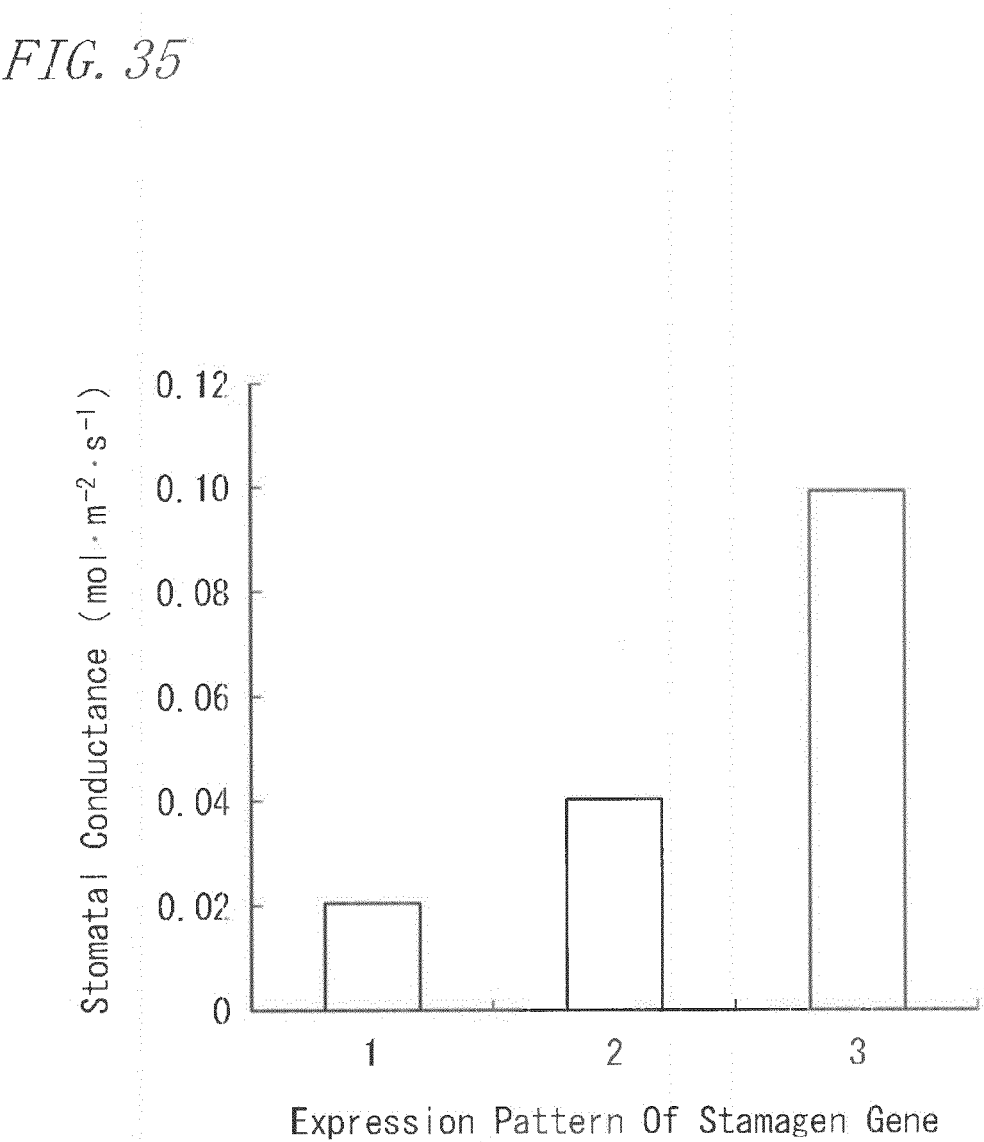
FIG. 35 is a graph showing the result of examining the relationship between an expression pattern of a stomagen gene and stomatal conductance in Test Example 12.

A photosynthesis measuring system {manufactured by LI-Cor, trade name: LI-6400} was calibrated by using atmospheric $CO_2$. Next, the light intensity of a chamber of the photosynthesis measuring system was set. Then, the leaf of the wild-type strain, the stomagen-silenced line or the stomagen-overexpressing line was sandwiched and maintained until the measured value of the photosynthesis measuring system was stabilized. Thereafter, for the stomagen-silenced line, the wild-type strain or the stomagen-overexpressing line, a photosynthetic rate and a stomatal conductance as an index of gas exchangeability were determined. The result of examining the relationship between an expression pattern of a stomagen gene and photosynthetic rate in Test Example 12 is shown in FIG. 34. In addition, the result of examining the relationship between an expression pattern of a stomagen gene and stomatal conductance in Test Example 12 is shown in FIG. 35. In the figure, lane 1 represents the stomagen-silenced line, lane 2 represents the wild-type strain and lane 3 represents the stomagen-overexpressing line.

From the results shown in FIG. 34 and FIG. 35, it can be seen that the photosynthetic rate is highest and the gas exchangeability is highest in the stomagen-overexpressing line. On the other hand, from the results shown in FIG. 34 and FIG. 35, it can be seen that the photosynthetic rate is lowest and the gas exchangeability is lowest in the stomagen-silenced line. These results suggest that, the more the expression level of a stomagen gene in a plant, the higher the photosynthetic rate and the higher the gas exchangeability.

Example 7

A cDNA encoding stomagen was introduced into pB2GW7, to give a vector for expressing stomagen. A stomagen-overexpressing soybean was prepared using the resulting vector for expressing stomagen, according to the method described in Literature 28, under Dr. Tetsuya Yamada of Hokkaido University.

Test Example 13

Figure 36:
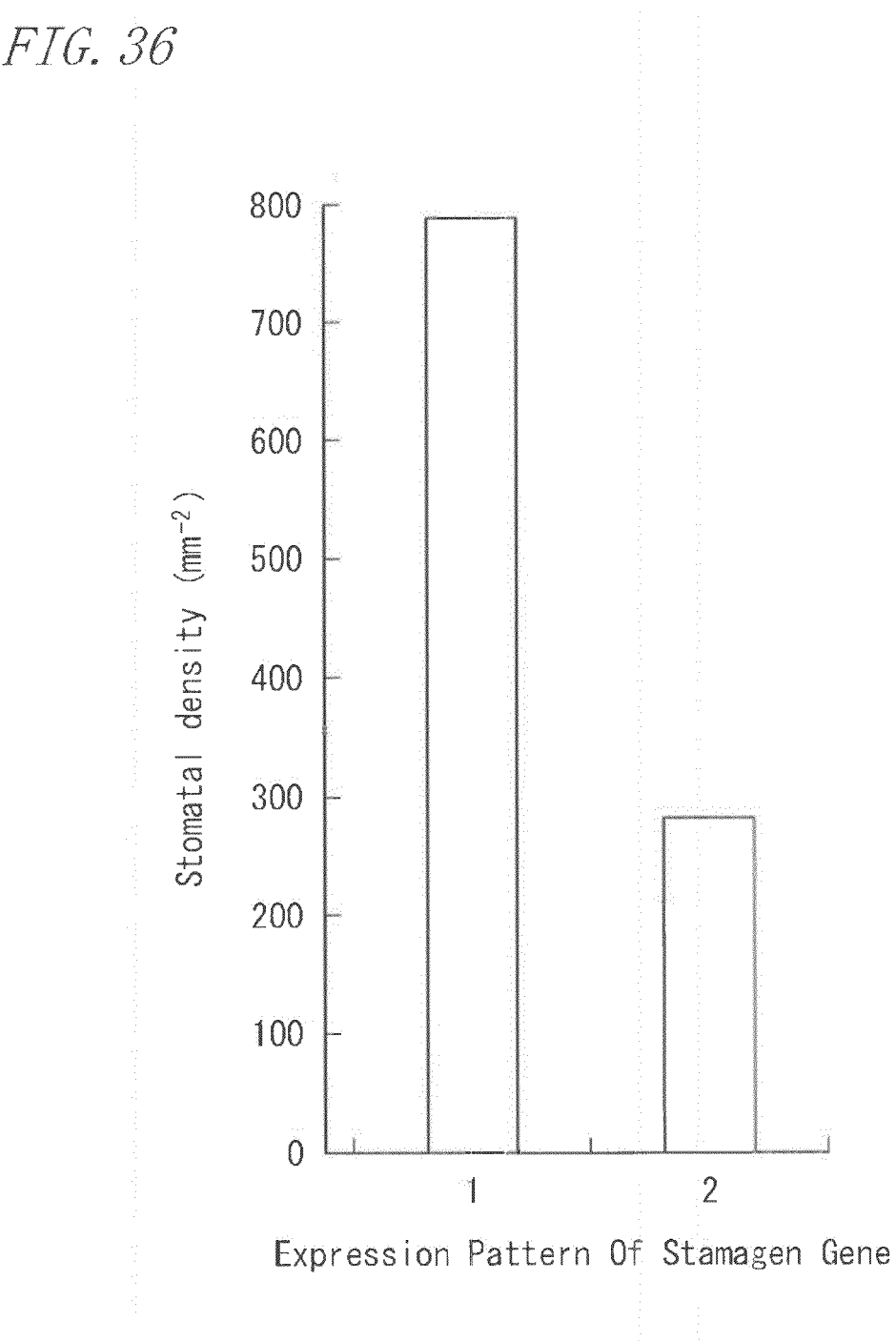
FIG. 36 is a graph showing the result of examining the relationship between the types of plants and stomatal density in Test Example 13.

The leaves of each of the stomagen-overexpressing soybean obtained in Example 7 and a soybean (Kariyutaka) {wild-type strain} were collected. Next, the surface of the leaves was observed under a differential interference microscope {manufactured by Zeiss, trade name: Axioskop plus microscope}, to determine the number of stomata in a square area of $0.22 \text{ mm}^2$. Then, stomatal density was calculated. Here, statistical analysis was conducted using R statistical analysis software. The result of examining the relationship between the types of plants and stomatal density in Test Example 13 is shown in FIG. 36. In the figure, lane 1 represents the stomagen-overexpressing soybean and lane 2 represents the wild-type strain.

Figure 37:
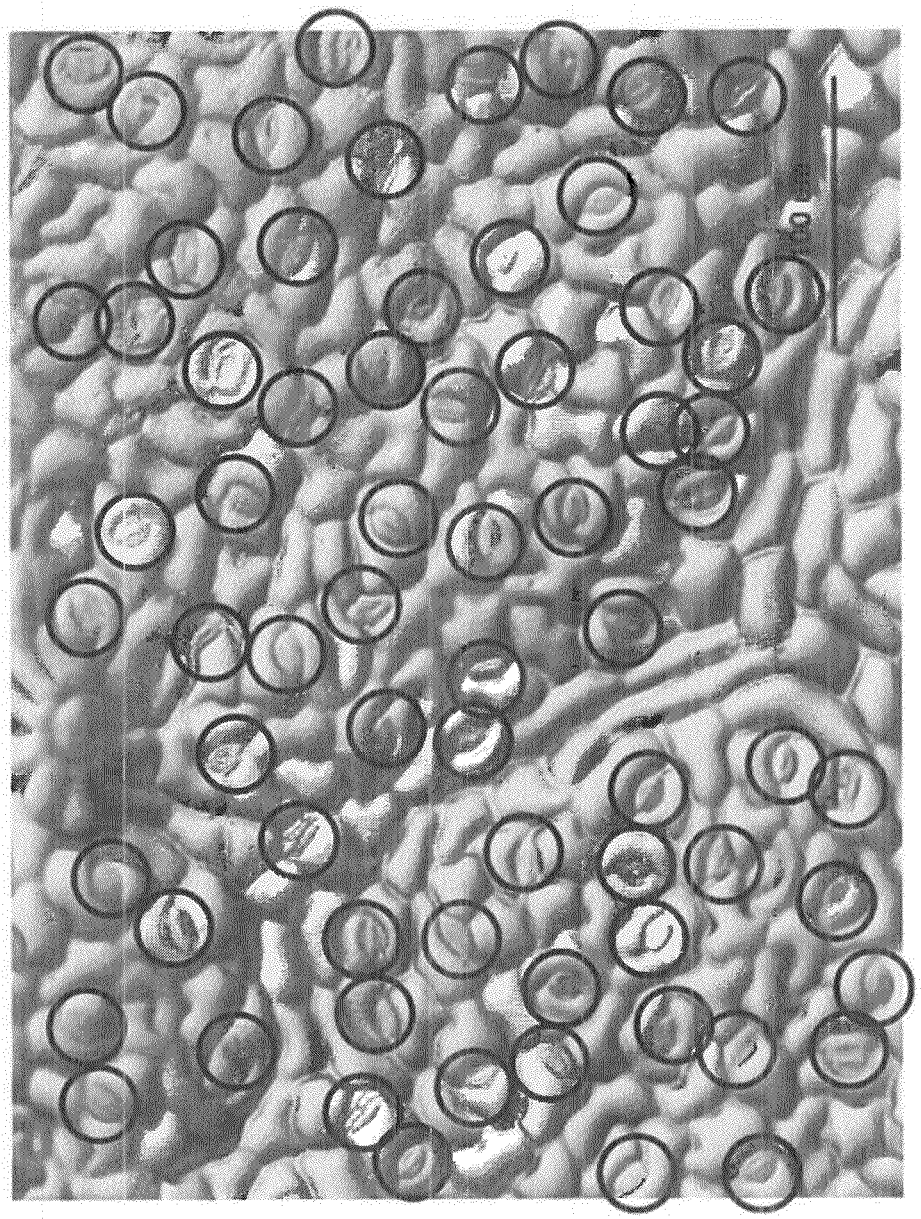
FIG. 37 is a photograph substituted for drawing of a differential interference image showing the result of observing a leaf of a stomagen-overexpressing soybean in Test Example 13.
Figure 38:
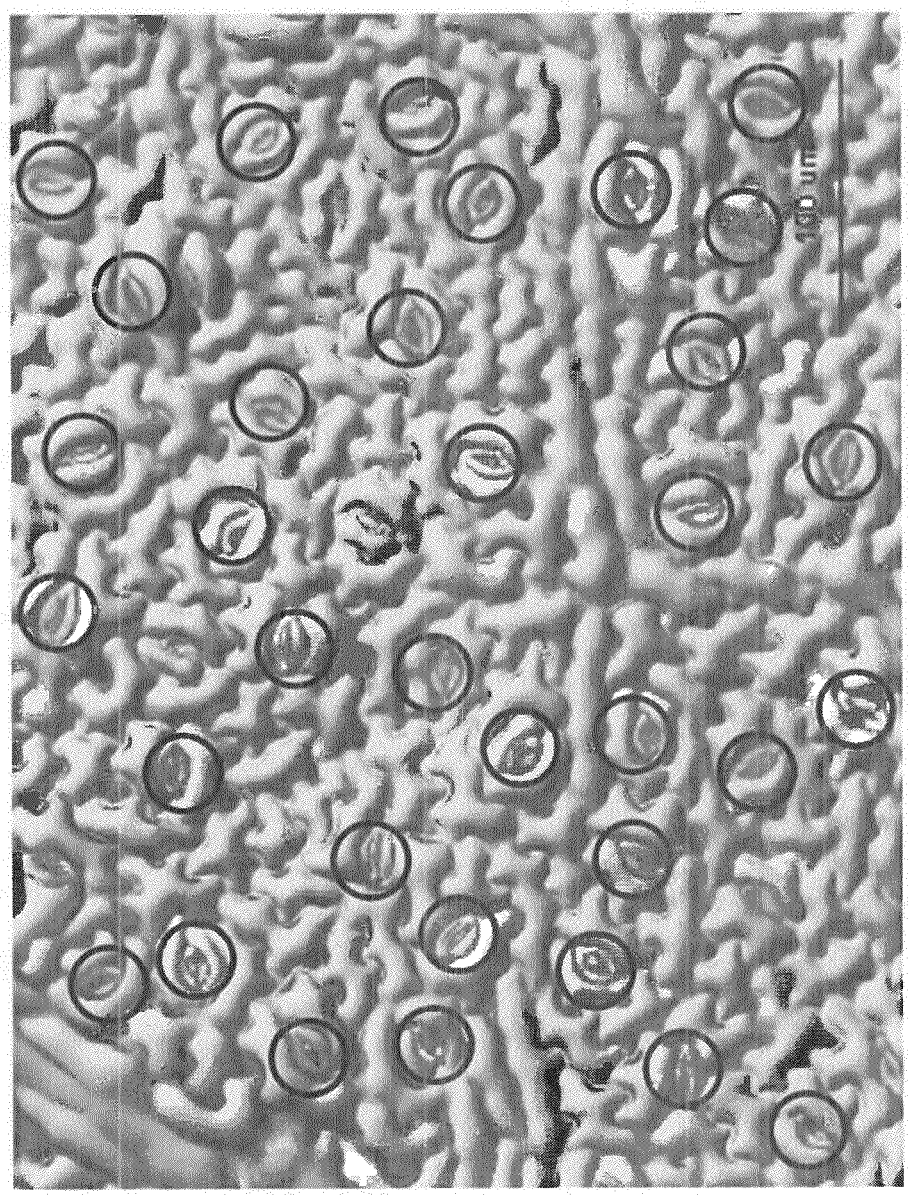
FIG. 38 is a photograph substituted for drawing of a differential interference image showing the result of observing leaf of a soybean (Kariyutaka) {wild-type strain} in Test Example 13.

In addition, the leaves of each of the stomagen-overexpressing soybean and soybean (Kariyutaka) {wild-type strain} were collected. Then, the leaves were fixed and made transparent, and then stomata were stained by carrying out the same operation as in Test Example 1. Thereafter, the leaves were observed under a differential interference microscope {manufactured by Zeiss, trade name: Axioskop plus microscope}. A differential interference image showing the result of observing the leaf of the stomagen-overexpressing soybean in Test Example 13 is shown in FIG. 37. In addition, a differential interference image showing the result of observing the leaf of the soybean (Kariyutaka) {wild-type strain} in Test Example 13 is shown in FIG. 38. In the figure, framed parts show stomata. In addition, in the figure, a scale bar represents 100 μm.

From the results shown in FIG. 36, FIG. 37 and FIG. 38, it can be seen that, when stomagen is overexpressed in soybean, the stomatal density increases as compared to the soybean (Kariyutaka) {wild-type strain} (see FIG. 38). Therefore, from the results, it can be seen that the number of stomata and/or stomata density in soybean can be increased by overexpressing stomagen.

Test Example 14

The seeds of rice {strain "Nipponbare"} were seeded to a container {50-mL volume, manufactured by greiner} with 5 mL of desalted water, and thereafter 200 μL of 80 μM stomagen (the synthetic stomagen obtained in Example 5) was added thereto. Then, the seeds were maintained at 22° C. for 8 days. Thereafter, the resulting plant was grown at 22° C. in a B5 sterilized medium. The second leaves of rice at 32 days after seeding were collected. Then, the second leaves were fixed and made transparent, and then stomata were stained by carrying out the same operation as in Test Example 1. Thereafter, the abaxial epidermis of the second leaves was observed under a differential interference microscope {manufactured by Zeiss, trade name: Axioskop plus microscope}. The abaxial epidermis of the second leaves of the rice at 32 days after seeding was observed by carrying out the same procedure as in the above with the use of a rice to which stomagen was not administered as a control. A differential interference image of abaxial epidermis of the second leaf of the rice to which synthesized stomagen was administered in Test Example 14 is shown in FIG. 39 (*a*) and a differential interference image of abaxial epidermis of the second leaf of the rice to which synthesized stomagen was not administered in Test Example 14 is shown in FIG. 39 (*b*). In the figures, a framed part represents a stoma. In the figures, a scale bar represents 50 μm.

From the results shown in FIG. 39, it can be seen that the number of stomata and stomatal density increase in abaxial epidermis of the second leaf of the rice to which synthetic stomagen is administered {see FIG. 39 (*a*)}, as compared to abaxial epidermis of the second leaf of the rice to which synthetic stomagen is not administered {see FIG. 39 (*b*)}. Therefore, from this result, it can be seen that the number of stomata and stomatal density in rice can be increased by administering stomagen to rice.

Example 8

Figure 40:
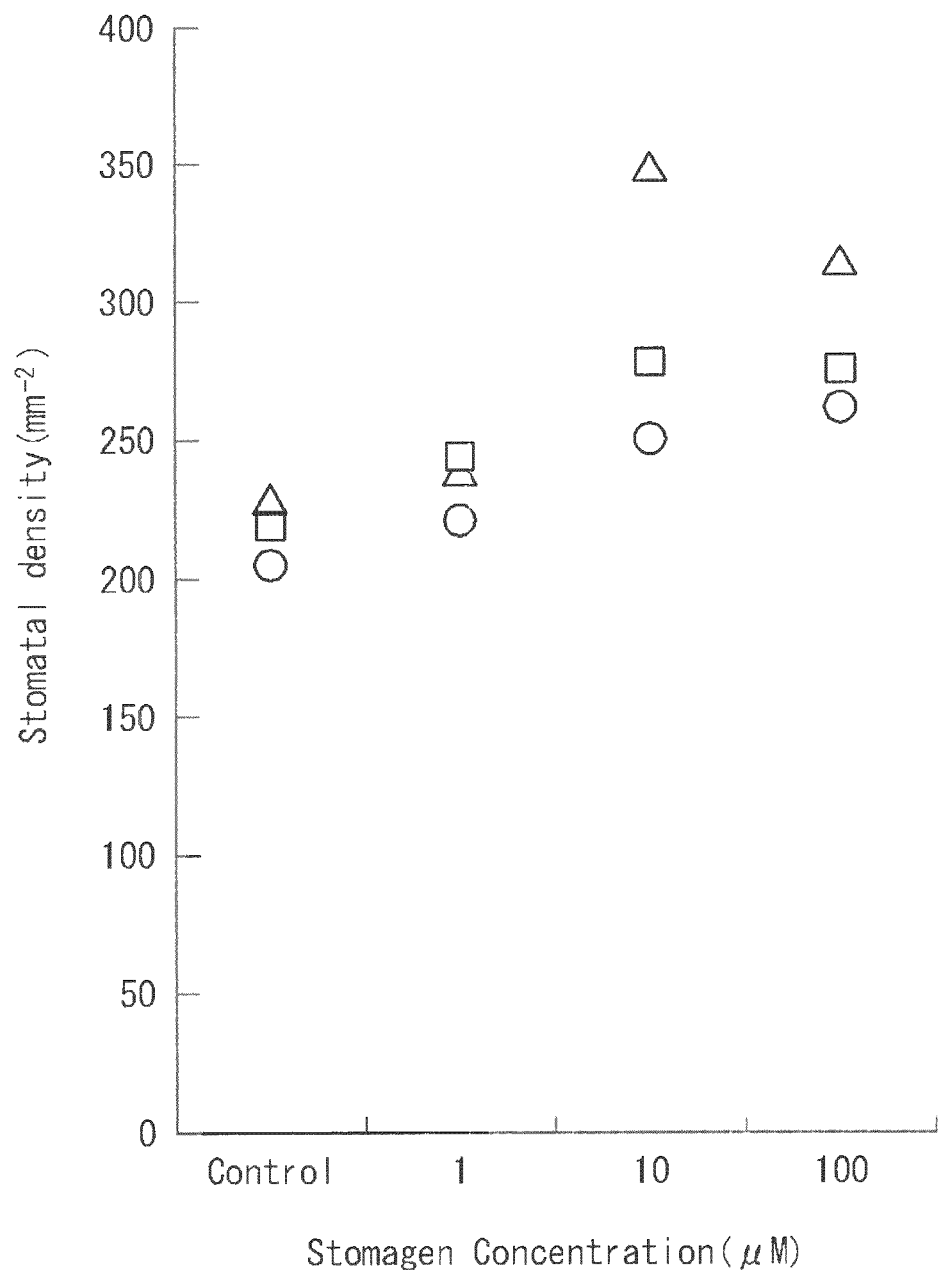
FIG. 40 is a graph showing the result of examining the relationship between stomagen concentration and stomatal density in Example 8.

The seeds of soybean (Kariyutaka) were seeded to a pot containing potting compost, germinated and then grown until the second leaf stage. Then, the synthetic stomagen obtained in Example 5 was added to the shoot apex, so as to have a concentration of 1 μM, 10 μM or 100 μM. Thereafter, the resulting plant was grown for a week and observed under a differential interference microscope {manufactured by Zeiss, trade name: Axioskop plus microscope}, to determine the number of stomata in a square area of 0.22 mm$^2$. Then, stomatal density was calculated. Here, statistical analysis was conducted using R statistical analysis software. In addition, stomatal density was calculated by carrying out the same procedure as in the above, except that an inactive polypeptide (polypeptide in which six cysteine residues in an amino acid sequence of stomagen were substituted with serines) was added in place of the synthetic stomagen obtained in Example 5, so as to have a concentration of 100 μM. The result of examining the relationship between stomagen concentration and stomatal density in Example 8 is shown in FIG. 40. In the figure, an open triangle, an open square and an open circle each show a different plant.

From the result shown in FIG. 40, it can be seen that the stomagen concentration and the stomatal density have positive correlation.

Test Example 15

Air containing carbon dioxide labeled with $^{11}$C ($^{11}CO_2$) was provided to *Arabidopsis thaliana* Col-0 line (stock number: CS60000) {wild-type strain} or the stomagen-silenced line obtained in Preparation Example 5 (stomagen-silenced line 10). Therefore, $^{11}CO_2$ taken in the wild-type strain or stomagen-silenced line was determined by using a positron imaging system {manufactured by Hamamatsu Photonics K. K., trade name: PETIS}. The result of determining $^{11}CO_2$ taken in the wild-type strain or stomagen-silenced line in Test Example 15 is shown in FIG. 41. In the figures, (*a*) shows a general photograph and (*b*) shows a positron image.

From the result shown in FIG. 41, it can be seen that the amount of carbon dioxide fixation in the wild-type strain normally expressing stomagen is remarkably high as compared to the amount of carbon dioxide fixation in the stomagen-silenced line. These results suggest that carbon dioxide fixation ability is increased by stomagen expression in a plant. Therefore, it is suggested that according to stomagen, an increase in the yield as a plant can be attempted.

Test Example 16

The chemically synthesized stomagen obtained in Example 5 was incubated at 60° C. for 5 minutes (sample number 3) or at 90° C. for 5 minutes (sample number 4). In addition, the chemically synthesized stomagen obtained in Example 5 was lyophilized (sample number 5).

The seeds of *Arabidopsis thaliana* Col-0 line (stock number: CS60000) were maintained and germinated in a B5 sterilized medium. To the *Arabidopsis thaliana* Col-0 line (stock number: CS60000) at 2 days after germination was administered the untreated stomagen (sample number 2), the stomagen incubated at 60° C. for 5 minutes (sample number 3), the stomagen incubated at 90° C. for 5 minutes (sample number 4), or the lyophilized stomagen (sample number 5), so as to have a concentration of 3 μM.

Thereafter, the *Arabidopsis thaliana* Col-0 line (stock number: CS60000) was grown at 22° C. for 3 days. Next, the cotyledon was collected, and the surface of the cotyledon was observed under a confocal microscope {manufactured by Zeiss, trade name: LSM510 META microscope}, to determine the number of stomata in a square area of 0.22 mm$^2$. Then, stomatal density was calculated. Here, statistical analysis was conducted using R statistical analysis software. Stomatal density was calculated by carrying out the same operation as described above with the use of *Arabidopsis thaliana* Col-0 line (stock number: CS60000) to which stomagen was not administered as a control (sample number 1). The result of examining the relationship between the types of samples and stomatal density in Test Example 16 is shown in FIG. 42.

Figure 42:
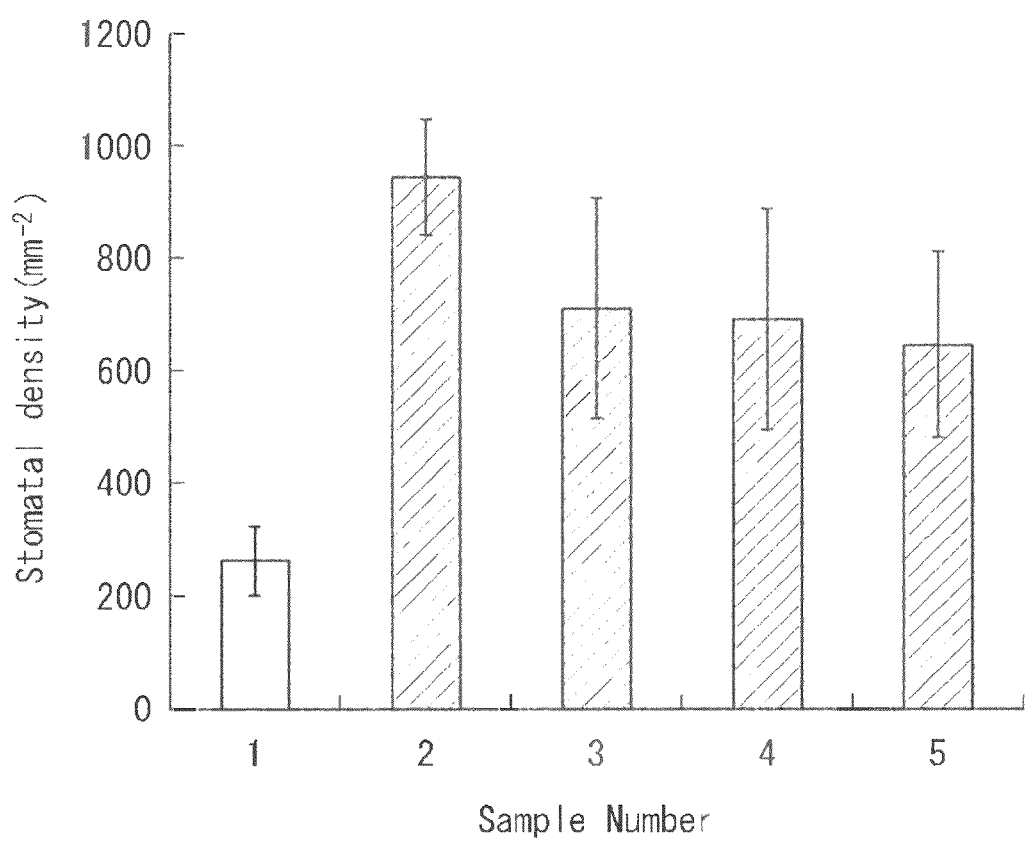
FIG. 42 is a graph showing the result of examining the relationship between the types of samples and stomatal density in Test Example 16.

From the result shown in FIG. 42, it can be seen that stomagen is stable to heat and drying.

These results suggest that the number of stomata and/or stomatal density in a plant can be increased by overexpression of stomagen in a plant or administration of stomagen to a plant, and an increase in the yield as a plant can be attempted.

List of References
1. Hetherington, A. M. & Woodward, F. I. The role of stomata in sensing and driving environmental change. Nature 424, 901-908 (2003).
2. Nadeau, J. A. & Sack, F. D. Stomatal development in *Arabidopsis*. In The *Arabidopsis* Book (eds Someville, C. & Meyerowitz, E) doi:10.1199/tab.0066 (American Society of Plant Biologists, 2002).
3. Nadeau, J. A. & Sack, F. D. Control of stomatal distribution on the *Arabidopsis* leaf surface. Science 296, 1697-1700 (2002).
4. Hara, K., Kajita, R., Torii, K. U., Bergmann, D. C. & Kakimoto, T. The secretory peptide gene EPF1 enforces the stomatal one-cell-spacing rules. Genes Dev. 21, 1720-1725 (2007).
5. Hunt, L. & Gray, J. E. The signaling peptide EPF2 controls asymmetric cell divisions during stomatal development. Curr. Biol. 19, 864-869 (2009).
6. Hara, K. et al. Epidermal cell density is autoregulated via a secretory peptide, EPIDERMAL PATTERNING FACTOR 2 in *Arabidopsis* leaves. Plant Cell Physiol. 50, 1019-1031 (2009).
7. Bergmann, D. C. Integrating signals in stomatal development. Curr. Opin. Plant Biol. 7, 26-32 (2004).
8. Shpak, E. D., McAbee, J. M., Pillitteri, L. J. & Torii, K. U. Stomatal patterning and differentiation by synergistic interactions of receptor kinases. Science 309, 290-293 (2005).
9. Berger, D.&Altmann, T. A subtilisin-like serine protease involved in the regulation of stomatal density and distribution in *Arabidopsis thaliana*. Genes Dev. 14, 1119-1131 (2000).
10. Nadeau, J. A. Stomatal development: new signals and fate determinants. Curr. Opin. Plant Biol. 12, 29-35 (2009).
11. Obayashi, T., Hayashi, S., Saeki, M., Ohta, H. & Kinoshita, K. ATTED-II provides coexpressed gene networks for *Arabidopsis*. Nucleic Acids Res. 37, D987-D991 (2009).
12. Sachs, T. The development of spacing patterns in the leaf epidermis. In Clonal Basis of Development 161-182 (Academic Press, 1987).
13. MacAlister, C. A., Ohashi-Ito, K. & Bergmann, D. C. Transcription factor control of asymmetric cell divisions that establish the stomatal lineage. Nature 445, 537-540 (2007).
14. Pillitteri, L. J., Sloan, D. B., Bogenschutz, N. L. & Torii, K. U. Termination of asymmetric cell division and differentiation of stomata. Nature 445, 501-505 (2007).
15. Serna, L., Torres-Contreras, J. & Fenoll, C. Specification of stomatal fate in *Arabidopsis*: evidences for cellular interactions. New Phytol. 153, 399-404 (2002).
16. Geisler, M., Yang, M. & Sack, F. D. Divergent regulation of stomatal initiation and patterning in organ and suborgan regions of the *Arabidopsis* mutants too many mouths and four lips. Planta 205, 522-530 (1998).
17. Geisler, M., Nadeau, J. & Sack, F. D. Oriented asymmetric divisions that generate the stomatal spacing pattern in *Arabidopsis* are disrupted by the too many mouths mutation. Plant Cell 12, 2075-2086 (2000).
18. von Grolla, U., Bergera, D. & Altmann, T. The subtilisin-like serine protease SDD1 mediates cell-to-cell signaling during *Arabidopsis* stomatal development. Plant Cell. 14, 1527-1539 (2002).
19. Schwab, R., Ossowski, S., Riester, M., Warthmann, N. & Weigel, D. Highly specific gene silencing by artificial microRNAs in *Arabidopsis*. Plant Cell 18, 1121-1133 (2006).
20. Dohi, K., Tamai, A. & Mori, M. Insertion in the coding region of the movement protein improves stability of the plasmid encoding a tomato mosaic virus-based expression vector. Arch. Viral. 153, 1667-1675 (2008).
21. Kono, A. et al. The *Arabidopsis* D-type cyclin CYCD4 controls cell division in the stomatal lineage of the hypocotyl epidermis. Plant Cell 19, 1265-1277 (2007).
22. Hara-Nishimura, I., Takeuchi, Y., Inoue, K. & Nishimura, M. Vesicle transport and processing of the precursor to 2S albumin in pumpkin. Plant J. 4, 793-800 (1993).
23. Shimada, T. et al. AtVPS29, a putative component of a retromer complex, is required for the efficient sorting of seed storage proteins. Plant Cell Physiol. 47, 1187-1194 (2006).
24. Kunieda, T. et al. NAC family proteins NARS1/NAC2 and NARS2/NAM in the outer integument regulate embryogenesis in *Arabidopsis*. Plant Cell 20, 2631-2642 (2008).
25. Livak, K. J. & Schmittgen, T. D. Analysis of relative gene expression data using real-time quantitative PCR and the 22DDC (T) method. Methods 25, 402-408 (2001).
26. Kinoshita, T. et al. Vacuolar processing enzyme is up-regulated in the lytic vacuoles of vegetative tissues during senescence and under various stressed conditions. Plant J. 19, 43-53 (1999).
27. Jensen, O. N., Podtelejnikov, A. & Mann, M. Delayed extraction improves specificity in database searches by matrix-assisted laser desorption/ionization peptide maps. Rapid Commun. Mass Spectrom. 10, 1371-1378 (1996).
28. Hiroshi Sato, et al., Production of transgenic plants and their early seed set in Japanese soybean variety, Kariyutaka. Plant Biotechnology 24:533-536 (2007).

{Sequence Listing Free Text}
SEQ ID NO.: 7 is a sequence of P10_prom_F.
SEQ ID NO.: 8 is a sequence of P10_prom_R.
SEQ ID NO.: 9 is a sequence of P10_F.
SEQ ID NO.: 10 is a sequence of P10_R.
SEQ ID NO.: 11 is a sequence of EPF1_F.
SEQ ID NO.: 12 is a sequence of EPF1_R.
SEQ ID NO.: 13 is a sequence of GFP-CfusF Bst.
SEQ ID NO.: 14 is a sequence of GFP-CfusR Bst.
SEQ ID NO.: 15 is a sequence of P-V_F.
SEQ ID NO.: 16 is a sequence of P-V_R.
SEQ ID NO.: 17 is a sequence of Venus_R.
SEQ ID NO.: 18 is a sequence of 2Ssp_F.
SEQ ID NO.: 19 is a sequence of 2Ssp<--p10m.
SEQ ID NO.: 20 is a sequence of 2Ssp-->p10m.
SEQ ID NO.: 21 is a sequence of P10m_F.
SEQ ID NO.: 22 is a sequence of CACC_amiA.
SEQ ID NO.: 23 is a sequence of P10ami1_I miR-s.
SEQ ID NO.: 24 is a sequence of P10ami1_II miR-a.
SEQ ID NO.: 25 is a sequence of P10ami1_III miR*s.
SEQ ID NO.: 26 is a sequence of P10ami1_IV miR*a.
SEQ ID NO.: 27 is a sequence of P10ami2_ImiR-s.
SEQ ID NO.: 28 is a sequence of P10ami2_IImiR-a.
SEQ ID NO.: 29 is a sequence of P10ami2_IIImiR*s.
SEQ ID NO.: 30 is a sequence of P10ami2_IVmiR*a.
SEQ ID NO.: 31 is a sequence of amiB.
SEQ ID NO.: 32 is a sequence of P10_RNAi_F.
SEQ ID NO.: 33 is a sequence of P10_RNAi_R.
SEQ ID NO.: 34 is a sequence of tmm SALK_011958-LP.
SEQ ID NO.: 35 is a sequence of SALK_011958-RP.
SEQ ID NO.: 36 is a sequence of epf1SALK_137549-LP.
SEQ ID NO.: 37 is a sequence of SALK_137549-RP.

SEQ ID NO.: 38 is a sequence of epf2SALK_047918-LP.
SEQ ID NO.: 39 is a sequence of SALK_047918-RP.
SEQ ID NO.: 40 is a sequence of spch SAIL_36_B6 LP.
SEQ ID NO.: 41 is a sequence of SAIL_36_B6_RP.

The invention claimed is:

1. A method for increasing a number, a density, or a number and a density, of stomata in a plant, the method comprising administering a polypeptide to a plant, wherein the polypeptide consists essentially of (A) SEQ ID NO:6, or (B) an amino acid sequence that is 95% identical to SEQ ID NO:6.

2. The method of claim 1, wherein the plant is a vascular plant.

3. A method for increasing the yield of a plant, the method comprising administering a polypeptide to a plant, wherein the polypeptide consists essentially of (A) SEQ ID NO:6, or (B) an amino acid sequence that is 95% identical to SEQ ID NO:6.

4. A method for increasing a number, a density, or a number and a density, of stomata in a plant, the method comprising overexpressing a polypeptide in a plant, wherein the polypeptide consists essentially of (A) SEQ ID NO:6, or (B) an amino acid sequence that is 95% identical to SEQ ID NO:6.

5. A method for increasing the yield of a plant, the method comprising overexpressing a polypeptide in a plant, wherein the polypeptide consists essentially of (A) SEQ ID NO:6, or (B) an amino acid sequence that is 95% identical to SEQ ID NO:6.

6. The method of claim 1, comprising administering the polypeptide that consists essentially of SEQ ID NO:6.

7. The method of claim 3, comprising administering the polypeptide that consists essentially of SEQ ID NO:6.

8. The method of claim 4, comprising overexpressing a polypeptide that consists essentially of SEQ ID NO:6.

9. The method of claim 5, comprising overexpressing a polypeptide that consists essentially of SEQ ID NO:6.

10. The method of claim 3, wherein the plant is a vascular plant.

11. The method of claim 4, wherein the plant is a vascular plant.

12. The method of claim 5, wherein the plant is a vascular plant.

* * * * *

```
                              SEQUENCE LISTING

<160> NUMBER OF SEQ ID NOS: 43

<210> SEQ ID NO 1
<211> LENGTH: 102
<212> TYPE: PRT
<213> ORGANISM: Arabidopsis thaliana

<400> SEQUENCE: 1

Met Lys His Glu Met Met Asn Ile Lys Pro Arg Cys Ile Thr Ile Phe
1               5                   10                  15

Phe Leu Leu Phe Ala Leu Leu Leu Gly Asn Tyr Val Val Gln Ala Ser
                20                  25                  30

Arg Pro Arg Ser Ile Glu Asn Thr Val Ser Leu Leu Pro Gln Val His
            35                  40                  45

Leu Leu Asn Ser Arg Arg Arg His Met Ile Gly Ser Thr Ala Pro Thr
        50                  55                  60

Cys Thr Tyr Asn Glu Cys Arg Gly Cys Arg Tyr Lys Cys Arg Ala Glu
65                  70                  75                  80

Gln Val Pro Val Glu Gly Asn Asp Pro Ile Asn Ser Ala Tyr His Tyr
                85                  90                  95

Arg Cys Val Cys His Arg
            100

<210> SEQ ID NO 2
<211> LENGTH: 123
<212> TYPE: PRT
<213> ORGANISM: Oryza sativa

<400> SEQUENCE: 2

Met Ala Asn Ala Cys Pro Thr Ser Thr Thr Ser Ser Leu Pro Leu Phe
1               5                   10                  15

Phe Leu Phe Cys Phe Leu Leu Phe Ser His Ala Arg Cys Asn Gln Gly
                20                  25                  30

His His Gly Ser Ile Ser Gly Thr Asp Tyr Gly Glu Gln Tyr Pro His
            35                  40                  45

Gln Thr Leu Pro Glu Glu His Ile His Leu Gln Glu Asn Ile Lys Val
        50                  55                  60

Leu Asn Lys Glu Arg Leu Pro Lys Tyr Ala Arg Arg Met Leu Ile Gly
65                  70                  75                  80

Ser Thr Ala Pro Ile Cys Thr Tyr Asn Glu Cys Arg Gly Cys Arg Phe
                85                  90                  95

Lys Cys Thr Ala Glu Gln Val Pro Val Asp Ala Asn Asp Pro Met Asn
            100                 105                 110

Ser Ala Tyr His Tyr Lys Cys Val Cys His Arg
        115                 120

<210> SEQ ID NO 3
<211> LENGTH: 104
<212> TYPE: PRT
<213> ORGANISM: Vitis vinifera

<400> SEQUENCE: 3

Met Leu Ile Ser Lys Gln Pro Asn Leu Phe Leu Val Leu Leu Phe Thr
1               5                   10                  15

Leu Leu Phe Ala Ala Tyr Phe Thr Gln Gly Ser Lys Ser Gln Val Val
                20                  25                  30
```

Pro Pro Tyr His Gln Arg Glu Ile Val His Leu Gln Ser Ser Gly Glu
            35                  40                  45

Gln Trp Met Asn Arg Asn Ser Arg Arg Leu Met Ile Gly Ser Thr Arg
 50                  55                  60

Pro Thr Cys Thr Tyr Asn Glu Cys Arg Gly Cys Lys Tyr Lys Cys Arg
 65                  70                  75                  80

Ala Glu Gln Val Pro Val Glu Gly Asn Asp Pro Ile Asn Ser Ala Tyr
                85                  90                  95

His Tyr Arg Cys Val Cys His Arg
            100

<210> SEQ ID NO 4
<211> LENGTH: 107
<212> TYPE: PRT
<213> ORGANISM: Populus trichocarpa

<400> SEQUENCE: 4

Met Ala Asn Thr Arg Leu Cys Tyr Leu Leu Ser Leu Leu Phe Thr Phe
 1               5                  10                  15

Ile Leu Ala Ala Phe Val Ile Gln Gly Ser Arg Asn Gln Glu Leu Leu
            20                  25                  30

Pro Tyr His Gln Ser Ile Ser Thr Pro Ser Gln Glu Asp Ser Gln Ala
            35                  40                  45

Leu Gly Gly Asn Glu Glu Gln Met Ser Ser Lys Arg Leu Met Ile Gly
 50                  55                  60

Ser Thr Ala Pro Thr Cys Thr Tyr Asn Glu Cys Arg Gly Cys Lys Tyr
 65                  70                  75                  80

Lys Cys Arg Ala Glu Gln Val Pro Val Glu Gly Asn Asp Pro Ile His
                85                  90                  95

Ser Ala Tyr His Tyr Lys Cys Ile Cys His Arg
            100                 105

<210> SEQ ID NO 5
<211> LENGTH: 61
<212> TYPE: PRT
<213> ORGANISM: Selaginella moellendorfii

<400> SEQUENCE: 5

Met Ile Asn Glu Trp Gln Tyr Pro Ser Asp Arg Ala Met Val Gly
 1               5                  10                  15

Ser Thr Ala Pro Ser Cys Thr Tyr Asn Glu Cys Arg Asp Cys Lys Thr
            20                  25                  30

Glu Cys Arg Ala Glu Gln Val Pro Leu Asn Gly Arg Asn Pro Lys Glu
            35                  40                  45

Ser Ala Tyr Arg Tyr Leu Cys Val Cys Arg Lys Arg His
 50                  55                  60

<210> SEQ ID NO 6
<211> LENGTH: 45
<212> TYPE: PRT
<213> ORGANISM: Arabidopsis thaliana

<400> SEQUENCE: 6

Ile Gly Ser Thr Ala Pro Thr Cys Thr Tyr Asn Glu Cys Arg Gly Cys
 1               5                  10                  15

Arg Tyr Lys Cys Arg Ala Glu Gln Val Pro Val Glu Gly Asn Asp Pro
            20                  25                  30

Ile Asn Ser Ala Tyr His Tyr Arg Cys Val Cys His Arg
         35                  40                  45

<210> SEQ ID NO 7
<211> LENGTH: 27
<212> TYPE: DNA
<213> ORGANISM: Artificial Sequence
<220> FEATURE:
<223> OTHER INFORMATION: A sequence of P10_prom_F

<400> SEQUENCE: 7
cacctagaaa agatttgctt cctaaac                                27

<210> SEQ ID NO 8
<211> LENGTH: 25
<212> TYPE: DNA
<213> ORGANISM: Artificial Sequence
<220> FEATURE:
<223> OTHER INFORMATION: A sequence of P10_prom_R

<400> SEQUENCE: 8
tctctacttc ttcttcttct tgctc                                  25

<210> SEQ ID NO 9
<211> LENGTH: 30
<212> TYPE: DNA
<213> ORGANISM: Artificial Sequence
<220> FEATURE:
<223> OTHER INFORMATION: A sequence of P10_F

<400> SEQUENCE: 9
caccgaatga agcatgaaat gatgaacatc                             30

<210> SEQ ID NO 10
<211> LENGTH: 29
<212> TYPE: DNA
<213> ORGANISM: Artificial Sequence
<220> FEATURE:
<223> OTHER INFORMATION: A sequence of P10_R

<400> SEQUENCE: 10
acaactatta tctatgacaa acacatcta                              29

<210> SEQ ID NO 11
<211> LENGTH: 30
<212> TYPE: DNA
<213> ORGANISM: Artificial Sequence
<220> FEATURE:
<223> OTHER INFORMATION: A sequence of EPF1_F

<400> SEQUENCE: 11
caccatgaag tctcttcttc tccttgcctt                             30

<210> SEQ ID NO 12
<211> LENGTH: 27
<212> TYPE: DNA
<213> ORGANISM: Artificial Sequence
<220> FEATURE:
<223> OTHER INFORMATION: A sequence of EPF1_R

<400> SEQUENCE: 12
tcaagggaca gggtaggact tattgtt                                27

<210> SEQ ID NO 13
<211> LENGTH: 56
<212> TYPE: DNA

```
<213> ORGANISM: Artificial Sequence
<220> FEATURE:
<223> OTHER INFORMATION: A sequence of GFP-CfusF Bst

<400> SEQUENCE: 13
ataggtcacc tggtggtggt ggtattgaag gtagaagtaa aggagaagaa ctttc        56

<210> SEQ ID NO 14
<211> LENGTH: 57
<212> TYPE: DNA
<213> ORGANISM: Artificial Sequence
<220> FEATURE:
<223> OTHER INFORMATION: A sequence of GFP-CfusR Bst

<400> SEQUENCE: 14
tatggttacc ttaatggtga tggtgatggt gatggtgttt gtatagttca tccatgc      57

<210> SEQ ID NO 15
<211> LENGTH: 30
<212> TYPE: DNA
<213> ORGANISM: Artificial Sequence
<220> FEATURE:
<223> OTHER INFORMATION: A sequence of P-V_F

<400> SEQUENCE: 15
tgtgtttgtc atagaatggt gagcaagggc                                    30

<210> SEQ ID NO 16
<211> LENGTH: 30
<212> TYPE: DNA
<213> ORGANISM: Artificial Sequence
<220> FEATURE:
<223> OTHER INFORMATION: A sequence of P-V_R

<400> SEQUENCE: 16
gcccttgctc accattctat gacaaacaca                                    30

<210> SEQ ID NO 17
<211> LENGTH: 24
<212> TYPE: DNA
<213> ORGANISM: Artificial Sequence
<220> FEATURE:
<223> OTHER INFORMATION: A sequence of Venus_R

<400> SEQUENCE: 17
ttaccccccc ccccttgta cagc                                           24

<210> SEQ ID NO 18
<211> LENGTH: 35
<212> TYPE: DNA
<213> ORGANISM: Artificial Sequence
<220> FEATURE:
<223> OTHER INFORMATION: A sequence of 2Ssp_F

<400> SEQUENCE: 18
caccatggcc agactcacaa gcatcattgc cctct                              35

<210> SEQ ID NO 19
<211> LENGTH: 30
<212> TYPE: DNA
<213> ORGANISM: Artificial Sequence
<220> FEATURE:
<223> OTHER INFORMATION: A sequence of 2Ssp<--p10m

<400> SEQUENCE: 19
atcatatggg tgcggtaggc gtacgcatct                                    30
```

<210> SEQ ID NO 20
<211> LENGTH: 30
<212> TYPE: DNA
<213> ORGANISM: Artificial Sequence
<220> FEATURE:
<223> OTHER INFORMATION: A sequence of 2Ssp-->p10m

<400> SEQUENCE: 20
accgcaccca tatgataggg tcgacagcac            30

<210> SEQ ID NO 21
<211> LENGTH: 30
<212> TYPE: DNA
<213> ORGANISM: Artificial Sequence
<220> FEATURE:
<223> OTHER INFORMATION: A sequence of P10m_F

<400> SEQUENCE: 21
cacccatatg atagggtcga cagcaccaac            30

<210> SEQ ID NO 22
<211> LENGTH: 29
<212> TYPE: DNA
<213> ORGANISM: Artificial Sequence
<220> FEATURE:
<223> OTHER INFORMATION: A sequence of CACC_amiA

<400> SEQUENCE: 22
caccctgcaa ggcgattaag ttgggtaac             29

<210> SEQ ID NO 23
<211> LENGTH: 40
<212> TYPE: DNA
<213> ORGANISM: Artificial Sequence
<220> FEATURE:
<223> OTHER INFORMATION: A sequence of P10ami1_I miR-s

<400> SEQUENCE: 23
gatacatcta taatgataag cgctctctct tttgtattcc     40

<210> SEQ ID NO 24
<211> LENGTH: 40
<212> TYPE: DNA
<213> ORGANISM: Artificial Sequence
<220> FEATURE:
<223> OTHER INFORMATION: A sequence of P10ami1_II miR-a

<400> SEQUENCE: 24
gagcgcttat cattatagat gtatcaaaga gaatcaatga     40

<210> SEQ ID NO 25
<211> LENGTH: 40
<212> TYPE: DNA
<213> ORGANISM: Artificial Sequence
<220> FEATURE:
<223> OTHER INFORMATION: A sequence of P10ami1_III miR*s

<400> SEQUENCE: 25
gagcacttat cattaaagat gtttcacagg tcgtgatatg     40

<210> SEQ ID NO 26
<211> LENGTH: 40
<212> TYPE: DNA
<213> ORGANISM: Artificial Sequence
<220> FEATURE:

```
<223> OTHER INFORMATION: A sequence of P10ami1_IV miR*a

<400> SEQUENCE: 26
gaaacatctt taatgataag tgctctacat atatattcct                40

<210> SEQ ID NO 27
<211> LENGTH: 40
<212> TYPE: DNA
<213> ORGANISM: Artificial Sequence
<220> FEATURE:
<223> OTHER INFORMATION: A sequence of P10ami2_ImiR-s

<400> SEQUENCE: 27
gatacatcta taatgataag cgctctctct tttgtattcc                40

<210> SEQ ID NO 28
<211> LENGTH: 40
<212> TYPE: DNA
<213> ORGANISM: Artificial Sequence
<220> FEATURE:
<223> OTHER INFORMATION: A sequence of P10ami2_IImiR-a

<400> SEQUENCE: 28
gagcgcttat cattatagat gtatcaaaga gaatcaatga                40

<210> SEQ ID NO 29
<211> LENGTH: 40
<212> TYPE: DNA
<213> ORGANISM: Artificial Sequence
<220> FEATURE:
<223> OTHER INFORMATION: A sequence of P10ami2_IIImiR*s

<400> SEQUENCE: 29
gagcacttat cattaaagat gtttcacagg tcgtgatatg                40

<210> SEQ ID NO 30
<211> LENGTH: 40
<212> TYPE: DNA
<213> ORGANISM: Artificial Sequence
<220> FEATURE:
<223> OTHER INFORMATION: A sequence of P10ami2_IVmiR*a

<400> SEQUENCE: 30
gaaacatctt taatgataag tgctctacat atatattcct                40

<210> SEQ ID NO 31
<211> LENGTH: 28
<212> TYPE: DNA
<213> ORGANISM: Artificial Sequence
<220> FEATURE:
<223> OTHER INFORMATION: A sequence of amiB

<400> SEQUENCE: 31
gcggataaca atttcacaca ggaaacag                             28

<210> SEQ ID NO 32
<211> LENGTH: 24
<212> TYPE: DNA
<213> ORGANISM: Artificial Sequence
<220> FEATURE:
<223> OTHER INFORMATION: A sequence of P10_RNAi_F

<400> SEQUENCE: 32
caccgatagg gtcgacagca ccaa                                 24
```

```
<210> SEQ ID NO 33
<211> LENGTH: 27
<212> TYPE: DNA
<213> ORGANISM: Artificial Sequence
<220> FEATURE:
<223> OTHER INFORMATION: A sequence of P10_RNAi_R

<400> SEQUENCE: 33
tcatatctat gacaaacaca tctataa                                              27

<210> SEQ ID NO 34
<211> LENGTH: 27
<212> TYPE: DNA
<213> ORGANISM: Artificial Sequence
<220> FEATURE:
<223> OTHER INFORMATION: A sequence of tmm SALK_011958-LP

<400> SEQUENCE: 34
atggcacgat atgaattctt ccgccaa                                              27

<210> SEQ ID NO 35
<211> LENGTH: 30
<212> TYPE: DNA
<213> ORGANISM: Artificial Sequence
<220> FEATURE:
<223> OTHER INFORMATION: A sequence of SALK_011958-RP

<400> SEQUENCE: 35
actagatatt agcataaaaa tgaaattagg                                           30

<210> SEQ ID NO 36
<211> LENGTH: 26
<212> TYPE: DNA
<213> ORGANISM: Artificial Sequence
<220> FEATURE:
<223> OTHER INFORMATION: A sequence of epf1SALK_137549-LP

<400> SEQUENCE: 36
tttttcatta ttcgcttaaa gtgtag                                               26

<210> SEQ ID NO 37
<211> LENGTH: 21
<212> TYPE: DNA
<213> ORGANISM: Artificial Sequence
<220> FEATURE:
<223> OTHER INFORMATION: A sequence of SALK_137549-RP

<400> SEQUENCE: 37
agcaaaagga aaacaaaacg g                                                    21

<210> SEQ ID NO 38
<211> LENGTH: 21
<212> TYPE: DNA
<213> ORGANISM: Artificial Sequence
<220> FEATURE:
<223> OTHER INFORMATION: A sequence of epf2SALK_047918-LP

<400> SEQUENCE: 38
taaaacctct gcctcaacca g                                                    21

<210> SEQ ID NO 39
<211> LENGTH: 21
<212> TYPE: DNA
<213> ORGANISM: Artificial Sequence
<220> FEATURE:
<223> OTHER INFORMATION: A sequence of SALK_047918-RP
```

```
<400> SEQUENCE: 39
ttaccggtat gatggagatg g                                              21

<210> SEQ ID NO 40
<211> LENGTH: 21
<212> TYPE: DNA
<213> ORGANISM: Artificial Sequence
<220> FEATURE:
<223> OTHER INFORMATION: A sequence of spch SAIL_36_B6 LP

<400> SEQUENCE: 40
gaaaaaccta gatcctcccc c                                              21

<210> SEQ ID NO 41
<211> LENGTH: 21
<212> TYPE: DNA
<213> ORGANISM: Artificial Sequence
<220> FEATURE:
<223> OTHER INFORMATION: A sequence of SAIL_36_B6_RP

<400> SEQUENCE: 41
tcctatgatc gatgcttggt c                                              21

<210> SEQ ID NO 42
<211> LENGTH: 10
<212> TYPE: PRT
<213> ORGANISM: Artificial Sequence
<220> FEATURE:
<223> OTHER INFORMATION: N-terminal amino acid sequence of the
      polypeptide produced in the stomagen-Venus-expressing line
<220> FEATURE:
<221> NAME/KEY: MOD_RES
<222> LOCATION: (8)..(8)
<223> OTHER INFORMATION: Unknown residue

<400> SEQUENCE: 42

Ile Gly Ser Thr Ala Pro Thr Xaa Thr Tyr
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Sequence from Lectin like protein
<220> FEATURE:
<221> NAME/KEY: MOD_RES
<222> LOCATION: (6)..(6)
<223> OTHER INFORMATION: Unknown residue
<220> FEATURE:
<221> NAME/KEY: MOD_RES
<222> LOCATION: (9)..(9)
<223> OTHER INFORMATION: Unknown residue

<400> SEQUENCE: 43

Val Lys Phe Asn Phe Xaa Ser Phe Xaa Gly
1               5                   10
```